United States Patent
Rinehart et al.

(10) Patent No.: US 11,718,849 B2
(45) Date of Patent: Aug. 8, 2023

(54) PHOSPHOPEPTIDE-ENCODING OLIGONUCLEOTIDE LIBRARIES AND METHODS FOR DETECTING PHOSPHORYLATION-DEPENDENT MOLECULAR INTERACTIONS

(71) Applicants: Yale University, New Haven, CT (US); Agilent Technologies, Inc., Santa Clara, CA (US)

(72) Inventors: Jesse Rinehart, Guilford, CT (US); Karl Barber, New Haven, CT (US); Farren Isaacs, Stamford, CT (US); Jeffrey R Sampson, San Jose, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 123 days.

(21) Appl. No.: 16/278,610

(22) Filed: Feb. 18, 2019

(65) Prior Publication Data
US 2019/0256843 A1  Aug. 22, 2019

Related U.S. Application Data

(60) Provisional application No. 62/639,279, filed on Mar. 6, 2018, provisional application No. 62/632,144, filed on Feb. 19, 2018.

(51) Int. Cl.
*C12N 15/10* (2006.01)

(52) U.S. Cl.
CPC ..... *C12N 15/1082* (2013.01); *C12N 15/1093* (2013.01)

(58) Field of Classification Search
CPC ..................................................... C12N 15/10
See application file for complete search history.

(56) References Cited

U.S. PATENT DOCUMENTS

| | | | |
|---|---|---|---|
| 2002/0106699 A1 | 8/2002 | Manfredi et al. | |
| 2002/0146774 A1 | 10/2002 | Souchelnytskyi et al. | |
| 2006/0148032 A1* | 7/2006 | Olayioye | A61P 35/00 435/69.1 |
| 2012/0329678 A1* | 12/2012 | Chen | C12N 15/10 506/16 |
| 2014/0273226 A1 | 9/2014 | Wu | |
| 2014/0273233 A1 | 9/2014 | Chen et al. | |
| 2016/0124000 A1 | 5/2016 | Stagljar et al. | |
| 2016/0355802 A1* | 12/2016 | Isaacs | C12Y 601/01 |

FOREIGN PATENT DOCUMENTS

| | | |
|---|---|---|
| WO | 2013176772 A1 | 11/2013 |
| WO | 2014144592 A2 | 9/2014 |
| WO | 2014144761 A2 | 9/2014 |

OTHER PUBLICATIONS

GE Healthcare, DYEnamic ET Terminator Cycle Sequencing Kit, Product Booklet, GE Healthcare, 2006, 1-20. (Year: 2006).*
Woodroof, H., Thesis, Biochemical Characterization of the Parkinson's Disease-Associated Kinase PINK1 Insigts From the Insect World, University of Dundee, 2014, 1-230. (Year: 2014).*
Agilent, BL21-CodonPlus Competent Cells, Instruction Manual, Agilent Technologies, 2015, 1-16. (Year: 2015).*
Pirman et al., A Flexible Codon in Genomically Recorded *Escherichia coli* Permits Programmable Protein Phosphorylation, Nature Communications, 2015, 1-6. (Year: 2015).*
Barber, K.W. et al., "Encoding human serine phosphopeptides in bacteria for proteome-wide identification of phosphorylation-dependent interactions," Nature Biotechnology, 2018, vol. 36, pp. 638-644.
Barber, K.W. et al. Kinase Substrate Profiling Using a Proteome-wide Serine-Oriented Human Peptide Library Biochemistry, Aug. 7, 2018; 57(31):4717-4725. doi: 10.1021/acs.biochem.8b00410.
Barber, Karl et al., Nature Biotechnology: Supplementary Figures, 16 pages, doi:10.1038/nbt.4150.
Bolger, A. et al., Trimmomatic: a flexible trimmer for Illumina sequence data. Bioinformatics, 30, 2114-2120, doi:10.1093/bioinformatics/btu170 (2014).
Collins, B. C. et al. Quantifying protein interaction dynamics by SWATH mass spectrometry: application to the 14-3-3 system. Nature Methods, 10, 1246-1253, doi:10.1038/nmeth.2703 (2013).
Edwin, F., et al., HECT Domain-containing E3 Ubiquitin Ligase Nedd4 Interacts with and Ubiquitinates Sprouty2. Journal of Biological Chemistry 285, 255-264, doi:10.1074/jbc.M109.030882 (2010).
Gao, S. et al. Ubiquitin Ligase Nedd4L Targets Activated Smad2/3 to Limit TGF-β Signaling. Molecular Cell 36, 457-468, doi:10.1016/j.molcel.2009.09.043 (2009).
Ghosh, I., et al., Antiparallel Leucine Zipper-Directed Protein Reassembly: Application to the Green Fluorescent Protein. Journal of the American Chemical Society 122, 5658-5659, doi:10.1021/ja994421w (2000).
Heo, J.-M., et al., The PINK1-PARKIN Mitochondrial Ubiquitylation Pathway Drives a Program of OPTN/NDP52 Recruitment and TBK1 Activation to Promote Mitophagy. Molecular Cell 60, 7-20, doi:10.1016/j.molcel.2015.08.016 (2015).
Hoppmann, C., et al., "Site-specific incorporation of phosphotyrosine using an expanded genetic code," Nature Chemical Biology, 2017, vol. 13, pp. 842-844.
Hornbeck, P. V. et al. PhosphoSitePlus: a comprehensive resource for investigating the structure and function of experimentally determined post-translational modifications in man and mouse. Nucleic Acids Research 40, doi:10.1093/nar/gkr1122 (2012).

(Continued)

*Primary Examiner* — Amy M Bunker
(74) *Attorney, Agent, or Firm* — Mannava & Kang, P.C.; Carol L. Bunner

(57) ABSTRACT

The present invention relates to libraries of phosphopeptide-encoding oligonucleotides and methods of preparing such libraries. The present invention also relates to methods of detecting, visualizing, or screening for phosphorylation-dependent protein-protein interactions using recombinant phosphopeptides and/or phosphopeptide-encoding oligonucleotides. The present invention also relates to sets or kits of oligonucleotides having regions that encode phosphopeptides.

7 Claims, 30 Drawing Sheets
Specification includes a Sequence Listing.

(56) References Cited

OTHER PUBLICATIONS

Huttlin, E. L. et al. Architecture of the human interactome defines protein communities and disease networks. Nature, doi:10.1038/nature22366 (2017).
Iakoucheva, L. M. et al. The importance of intrinsic disorder for protein phosphorylation. Nucleic acids research 32, 1037-1049 (2004).
Johnson, C. et al. Bioinformatic and experimental survey of 14-3-3-binding sites. Biochemical Journal 427, 69-78, doi:10.1042/BJ20091834 (2010).
Johnson, G. L. & Lapadat, R. Mitogen-Activated Protein Kinase Pathways Mediated by ERK, JNK, and p38 Protein Kinases. Science 298, 1911-1912, doi:10.1126/science.1072682 (2002).
Kanai, F. et al. TAZ: a novel transcriptional co-activator regulated by interactions with 14-3-3 and PDZ domain proteins. The EMBO Journal 19, 6778-6791, doi:10.1093/emboj/19.24.6778 (2000).
Kosuri, S. et al. Scalable gene synthesis by selective amplification of DNA pools from high-fidelity microchips. Nature Biotechnology 28, 1295-1299, doi:10.1038/nbt.1716 (2010).
Lajoie, M. J. et al. Genomically Recoded Organisms Expand Biological Functions. Science 342, 357-360, doi:10.1126/science.1241459 (2013).
Larman, B. H. et al. Autoantigen discovery with a synthetic human peptidome. Nature Biotechnology 29, 535-541, doi:10.1038/nbt.1856 (2011).
Lee, S. et al. A Facile Strategy for Selective Incorporation of Phosphoserine into Histones. Angewandte Chemie 125, 5883-5887, doi: 10.1002/ange.201300531 (2013).
LeProust, E. M. et al. Synthesis of high-quality libraries of long (150mer) oligonucleotides by a novel depurination controlled process. Nucleic acids research 38, 2522-2540 (2010).
Lu, P.-J., et al., Function of WW Domains as Phosphoserine—or Phosphothreonine-Binding Modules. Science 283, 1325-1328, doi:10.1126/science.283.5406.1325 (1999).
Luo, X. et al., "Genetically encoding phosphotyrosine and its nonhydrolyzable analog in bacteria," Nature Chemical Biology, 2017, vol. 13, pp. 845-849.
Marx, H. et al. A large synthetic peptide and phosphopeptide reference library for mass spectrometry-based proteomics. Nature Biotechnology 31, 557-564, doi:10.1038/nbt.2585 (2013).
Matsumoto, M. et al. A large-scale targeted proteomics assay resource based on an in vitro human proteome. Nature Methods 14, 251-258, doi:10.1038/nmeth.4116 (2016).
Ordureau, A. et al. Defining roles of PARKIN and ubiquitin phosphorylation by PINK1 in mitochondrial quality control using a ubiquitin replacement strategy. Proceedings of the National Academy of Sciences 112, 6637-6642, doi:10.1073/pnas.1506593112 (2015).
O'Shea, J. P. et al. pLogo: a probabilistic approach to visualizing sequence motifs. Nature methods 10, 1211-1212 (2013).
Oza, J.P. et al., "Robust production of recombinant phosphoproteins using cell-free protein synthesis," Nature Communications, 1-7, doi: 10.1038/ncomms9168 (2015).
Park, H.-S. et al. Expanding the Genetic Code of *Escherichia coli* with Phosphoserine. Science 333, 1151-1154, doi:10.1126/science.1207203 (2011).
Pirman, N. L. et al. A flexible codon in genomically recoded *Escherichia coli* permits programmable protein phosphorylation. Nature communications 6, 8130, doi:10.1038/ncomms9130 (2015).
Rogerson, D. T. et al. Efficient genetic encoding of phosphoserine and its nonhydrolyzable analog. Nature Chemical Biology 11, 496-503, doi:10.1038/nchembio.1823 (2015).
Sawyer, N. et al. Designed Phosphoprotein Recognition in *Escherichia coli*. ACS Chemical Biology 9, 2502-2507, doi:10.1021/cb500658w (2014).
Skouloudaki, K. & Walz, G. YAP1 Recruits c-Abl to Protect Angiomotin-Like 1 from Nedd4-Mediated Degradation. PLoS ONE 7 (2012).
Spagnol, G. et al. Structural Studies of the Nedd4 WW Domains and Their Selectivity for the Connexin43 (Cx43) Carboxyl Terminus. Journal of Biological Chemistry 291, 7637-7650, doi:10.1074/jbc.m115.701417 (2016).
Tinti, M. et al. ANIA: ANnotation and Integrated Analysis of the 14-3-3 interactome. Database 2014, doi:10.1093/database/bat085 (2014).
Tzivion, G., et al., FoxO transcription factors; Regulation by AKT and 14-3-3 proteins. Biochimica et Biophysica Acta (BBA)—Molecular Cell Research 1813, 1938-1945 (2011).
Ubersax, J. A. & Ferrell, J. E. Mechanisms of specificity in protein phosphorylation. Nature Reviews Molecular Cell Biology 8, 530-541, doi:10.1038/nrm2235 (2007).
Yaffe, M. B. et al. The Structural Basis for 14-3-3:Phosphopeptide Binding Specificity. Cell 91, 961-971, doi:10.1016/S0092-8674(00)80487-0 (1997).
Yang, et al., Nedd4 and Nedd4-2: closely related ubiquitin-protein ligases with distinct physiological functions. Cell Death & Differentiation 17, 68-77, doi:10.1038/cdd.2009.84 (2009).
Zhang, M.S. et al., "Biosynthesis and genetic encoding of phosphothreonine through parallel selection and deep sequencing," Nature Methods, 2017, vol. 14(7), pp. 729-736.
Zhou, S. et al. SH2 domains recognize specific phosphopeptide sequences. Cell 72, 767-778, doi:10.1016/0092-8674 (93)90404-E (1993).
International Search Report & Written Opinion dated Jun. 3, 2019, Application No. PCT/US2019/018432, 13 pages.
Tinti, M. et al.,"Profiling Phosphopeptide-Binding Domain Recognition Specificity Using Peptide Microarrays," Small Molecule Microarrays: Methods and Protocols, Methods in Molecular Biology, Mahesh Uttamchandani and Shao Q. Yao (eds.), 2017, 177-193.
European Patent Office, "The extended European search report, EP application No. 19754403.4-1118", dated Mar. 3, 2022, 14 pages.
Wehr Michael C. et al., "Analysis of transient phosphorylation-dependent protein-protein interactions in living mammalian cells using split-TEV", BMC Biotechnology, Biomed Central Ltd, vol. 8, No. 1, Jul. 13, 2008, 15 pages.
Spotts J M et al., "Time-lapse imaging of a dynamic phosphorylation-dependent protein-protein interaction in mammalian cells", Proceedings of the National Academy of Sciences of the United States of America (PNAS), vol. 99, No. 23, Nov. 12, 2002, pp. 15142-15147.
European Patent Office, "The partial supplemental European search report, EP application No. 19754403.4-1118", dated Nov. 29, 2021, 17 pages.

\* cited by examiner

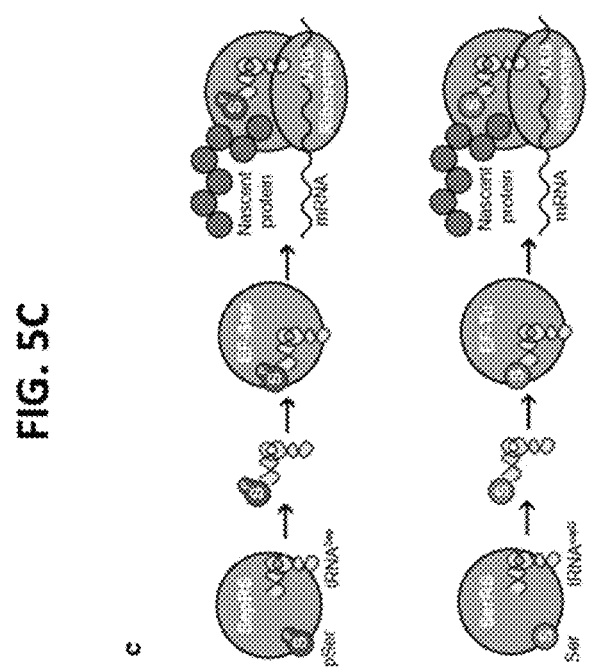
FIG. 5A
FIG. 5B
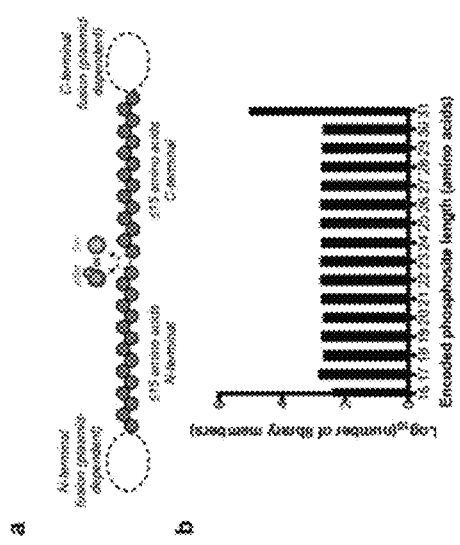
FIG. 5C

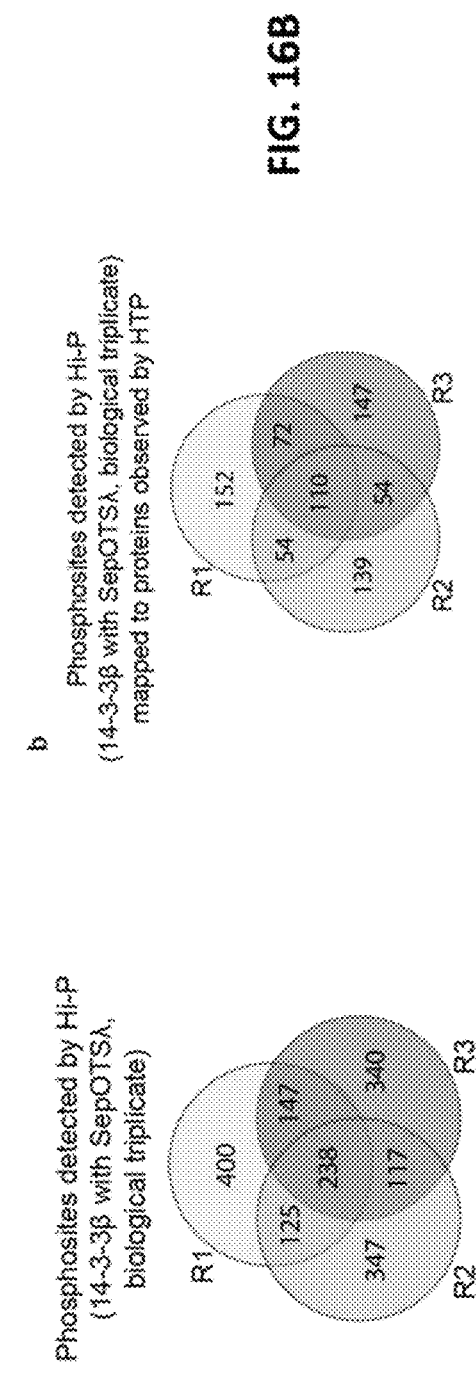
FIG. 16A
FIG. 16B
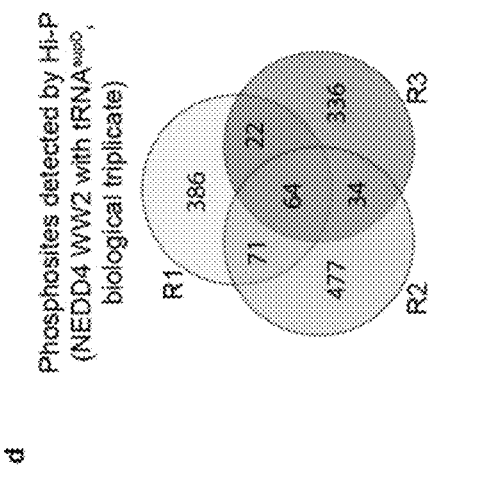
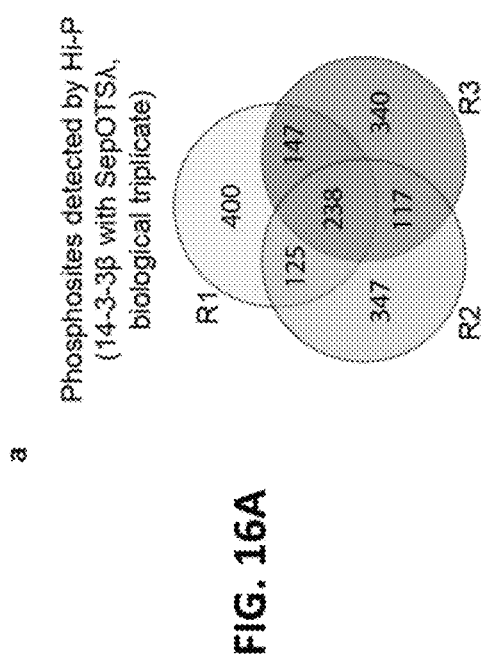
FIG. 16C
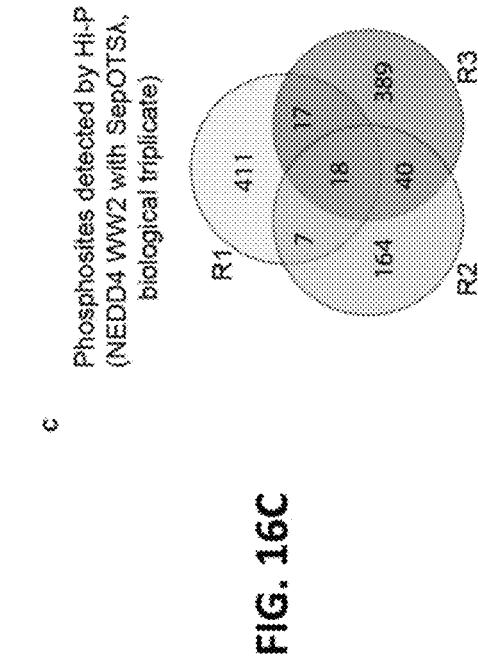
FIG. 16D

PHOSPHOPEPTIDE-ENCODING OLIGONUCLEOTIDE LIBRARIES AND METHODS FOR DETECTING PHOSPHORYLATION-DEPENDENT MOLECULAR INTERACTIONS

CROSS REFERENCE TO RELATED APPLICATIONS

This application claims benefit of the filing dates and rights of priority to U.S. Provisional Application No. 62/632,144, filed on Feb. 19, 2018 and U.S. Provisional Application No. 62/639,279, filed on Mar. 6, 2018, which are incorporated by references herein.

FIELD OF THE INVENTION

The present invention relates to libraries of phosphopeptide-encoding oligonucleotides and methods of preparing such libraries. The present invention also relates to methods of detecting phosphorylation-dependent protein-protein interactions or other molecular interactions, using recombinant phosphopeptides expressed from phosphopeptide-encoding oligonucleotides.

BACKGROUND OF THE INVENTION

Protein phosphorylation is one of the most common and critical post-translational modifications governing signaling cascades in humans. Phosphorylation of protein kinases governs their activity and regulation. The importance of regulation by phosphorylation is further emphasized by the fact that protein kinases comprise nearly 2% of the human proteome and numerous kinases have been implicated in processes that control cell proliferation, motility, and apoptosis in healthy and diseased human cells.

The dynamic interplay between kinases, phosphatases and their substrates results in the presence of thousands of unique phosphorylated proteins in a human cell at any given time, influencing cellular identity and function. Ubersax, J. A. & Ferrell, J. E. Mechanisms of specificity in protein phosphorylation. *Nature Reviews Molecular Cell Biology* 8, 530-541, doi:10.1038/nrm2235 (2007). Serine phosphorylation is one of the most common post-translational modification in eukaryotes, playing an integral role in the modulation of enzymatic activity and intermolecular interactions. See Yaffe, M. B. et al. The Structural Basis for 14-3-3: Phosphopeptide Binding Specificity. *Cell* 91, 961-971, doi:10.1016/S0092-8674(00)80487-0 (1997); Johnson, G. L. & Lapadat, R. Mitogen-Activated Protein Kinase Pathways Mediated by ERK, JNK, and p38 Protein Kinases. *Science* 298, 1911-1912, doi:10.1126/science.1072682 (2002).

While identification of phosphorylation sites within the human proteome has progressed in recent years, understanding of phosphorylation cascades is limited due to lack of knowledge of which kinases are responsible for each phosphorylation event and the specific arrangement of phosphorylation sites leading to an active kinase that phosphorylates its target substrate. Establishing connections of kinases to the phosphoproteome and revealing signaling networks also remain important challenges.

Since phosphorylation plays a central role in protein-protein interactions through phospho-binding domains, new approaches that can address these questions in a comprehensive and unbiased fashion are needed. Studying protein phosphorylation has been limited by the inability to generate phosphoproteins with the specificity of natural systems. Genetically encoded non-standard amino acids (NSAAs) have recently enabled site-specific incorporation of phosphoserine into proteins.

Recent human interactome studies have identified tens of thousands of putative protein-protein interactions (See Huttlin, E. L. et al. Architecture of the human interactome defines protein communities and disease networks. *Nature*, doi:10.1038/nature22366 (2017)), but the relevance of phosphorylation in assembled complexes is difficult to ascertain due to heterogeneous and often low-stoichiometric phosphorylation in cells. To elucidate the structural and functional importance of protein phosphorylation, genetically programmable incorporation of phosphoserine (pSer) as a nonstandard amino acid in *E. coli* has proven a powerful tool to generate recombinant phosphoproteins. Park, H.-S. et al. Expanding the Genetic Code of *Escherichia coli* with Phosphoserine. *Science* 333, 1151-1154, doi:10.1126/science.1207203 (2011); Pirman, N. L. et al. A flexible codon in genomically recoded *Escherichia coli* permits programmable protein phosphorylation. *Nature communications* 6, 8130, doi:10.1038/ncomms9130 (2015); Heo, J.-M., et al., The PINK1-PARKIN Mitochondrial Ubiquitylation Pathway Drives a Program of OPTN/NDP52 Recruitment and TBK1 Activation to Promote Mitophagy. *Molecular Cell* 60, 7-20, doi:10.1016/j.molcel.2015.08.016 (2015); Ordureau, A. et al. Defining roles of PARKIN and ubiquitin phosphorylation by PINK1 in mitochondrial quality control using a ubiquitin replacement strategy. *Proceedings of the National Academy of Sciences* 112, 6637-6642, doi:10.1073/pnas.1506593112 (2015); Rogerson, D. T. et al. Efficient genetic encoding of phosphoserine and its nonhydrolyzable analog. *Nature Chemical Biology* 11, 496-503, doi:10.1038/nchembio.1823 (2015); and Lee, S. et al. A Facile Strategy for Selective Incorporation of Phosphoserine into Histones. *Angewandte Chemie* 125, 5883-5887, doi:10.1002/ange.201300531 (2013). However, this technology has been limited to the study of only a few proteins and the functional significance of the majority of protein phosphorylation sites remains unknown.

It has been shown that a genomically recoded organism (GRO), in which all TAG stop codons were converted to TAA and the deletion of RF-1, converted TAG to an open sense codon dedicated for incorporating phosphoaminoacids. Pirman, N. L. et al. A flexible codon in genomically recoded *Escherichia coli* permits programmable protein phosphorylation. *Nature communications* 6, 8130 (2015); Lajoie, M. J. et al. Genomically Recoded Organisms Expand Biological Functions. *Science* 342, 357-360 (2013). This enables efficient and multiple site-specific expression of human phosphoproteins in an engineered bacterial system (i.e., GRO containing phosphoserine orthogonal translation system, OTS). Furthermore, it provides a technology to address questions probing the connectivity of the human phosphoproteome and the functional landscape of phospho-binding domains.

BRIEF DESCRIPTION OF THE DRAWINGS

FIGS. 5A to 5H illustrates design, production and evaluation of a library of phosphopeptide-encoding oligonucleotides that encodes a human serine phosphoproteome.

FIG. 16A shows overlap between phosphosite sequences observed in biological triplicate samples by Hi-P using the 14-3-3σ isoform and the mode #2 phosphosite library expressed using SepOTSλ. FIG. 16B shows overlap of phosphosite sequences by Hi-P in biological triplicate mapping to proteins that had been previously-observed candidate interactors with 14-3-3β. FIG. 16C shows overlap between phosphosite sequences observed in biological triplicate samples by Hi-P using the NEDD4 WW2 domain and the mode #2 phosphosite library expressed using SepOTSλ. FIG. 16D shows overlap between phosphosite sequences observed in biological triplicate samples by Hi-P using the NEDD4 WW2 domain and the mode #2 phosphosite library expressed using tRNA$^{supD}$. R=replicate.

DETAILED DESCRIPTION OF THE INVENTION

Figure 1A:
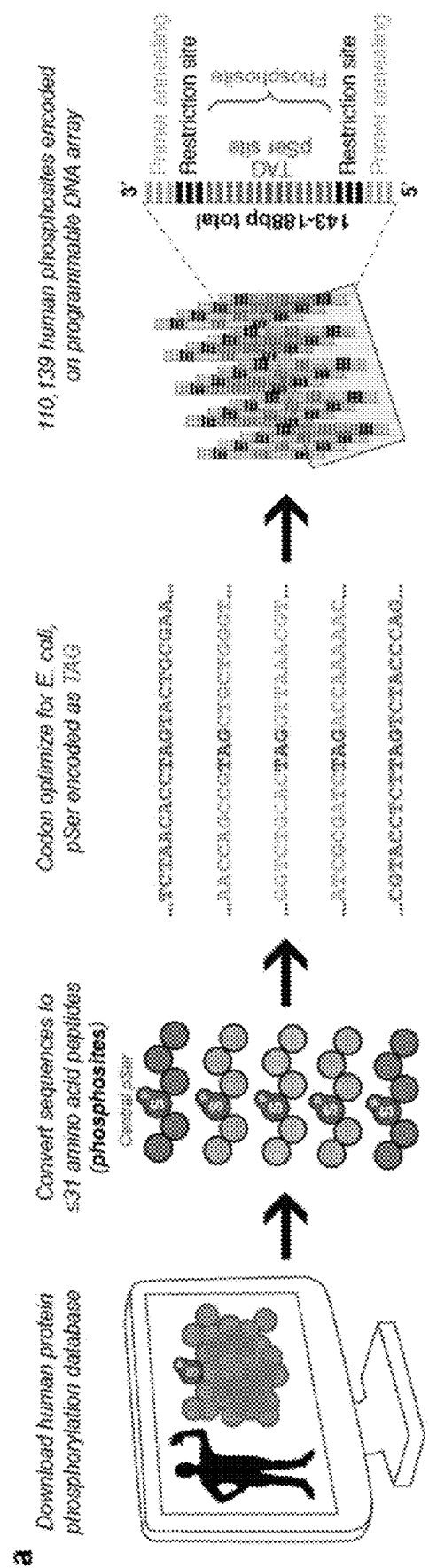
FIGS. 1A to 1C illustrate design and production of a library of phosphopeptide-encoding oligonucleotides.

As one aspect of the present invention, methods of preparing a library of phosphopeptide-encoding oligonucleotides are provided. The methods comprise selecting phosphopeptide sequences matching regions of native protein sequences comprising (i) a phosphorylation-susceptible residue and (ii) 0 to 15 residues on each side of the phosphorylation-susceptible residue. The selected phosphopeptide sequences are converted into phosphopeptide-encoding nucleic acid sequences. A library of phosphopeptide-encoding oligonucleotides having the converted phosphopeptide-encoding nucleic acid sequences is synthesized.

As another aspect of the present invention, sets or kits of plasmids, vectors or cells are provided. In some embodiments, the sets or kits of plasmids and/or vectors comprise phosphopeptide-encoding oligonucleotides made according to any of the preparation methods described herein. In some embodiments, sets or kits of cells are provided which comprise amplification products of a library of phosphopeptide-encoding oligonucleotides as described herein. In some embodiments of the sets or kits, the phosphopeptide-encoding oligonucleotides or amplicons thereof are inserted into vectors or plasmids which further comprise a region encoding a first portion of a reporter.

As another aspect of the present invention, methods to detect or visualize a phosphorylation-dependent protein-protein interaction or other molecular interaction are provided. In some embodiments, these methods use the sets or kits of plasmids or cells described herein. The detecting or visualizing methods can comprise expressing the phosphopeptide-encoding oligonucleotides to provide a first fusion protein comprising a phosphopeptide and a first portion of a reporter; providing a second fusion protein comprising a candidate having a known or suspected phosphoprotein-binding region and a second portion of the reporter; and detecting a signal from interaction of the first fusion protein and the second fusion protein.

As another aspect of the present invention, sets or kits of oligonucleotides are provided. Each of the oligonucleotides has a region that encodes a phosphopeptide, wherein the set or kit comprises at least 10 different oligonucleotides (alternatively at least 100, 1000, 3,000, 10,000, 30,000, or 100,000 different oligonucleotides). In some embodiments, each of the oligonucleotides comprises a codon that codes for a phosphorylated residue in the presence of one or more enzymes or factors (such as Sep aminoacyl-tRNA synthetase and engineered elongation factor Tu). For example, the codon can be TAG or UAG.

As yet another aspect of the present invention, methods are provided for screening candidates for a phosphorylation-dependent protein-protein interaction or other molecular interactions. The methods comprise providing a first fusion protein comprising a phosphopeptide and a first portion of a reporter; providing a second fusion protein comprising a candidate having a suspected phosphoprotein-binding region and a second portion of the reporter; detecting a signal from interaction of the first fusion protein and the second fusion protein; and identifying the candidate as having a phosphopeptide-binding region.

The present disclosure describes the first bacterially encoded representation of the entire human serine phosphoproteome, using a phosphoserine (pSer) orthogonal translation system in a genomically recoded strain of E. coli (i.e., GRO). From a library of phosphopeptide-encoding oligonucleotides, site-specific pSer incorporation was detected in >36,000 recombinant phosphoproteins by mass spectrometry. Utility of synthetic phosphoproteomes is demonstrated by importing the recombinant human phosphoproteome library module into a proximity capture/high-throughput sequencing platform to detect and identify phosphorylation-dependent protein-protein interactions or other molecular interactions. Using the novel detection method, a 30-fold sequence enrichment of previously-known pSer-dependent 14-3-3 interactions was obtained, and >600 novel candidate pSer-dependent interactions for 14-3-3 proteins and WW domains were obtained. Many of those interactions do not comply with known interaction sequence motifs.

The present disclosure provides superior methods and reagents to address functional questions surrounding the phosphoserine component of the human phosphoproteome. The present disclosure enables identification of phosphorylation sites that drive protein-protein interactions or other molecular interactions in general, followed by systematic screens of the substrates, thereby allowing one to assign biological function to a portion of the human phosphoproteome.

The present disclosure provides a rapid and cost-effective production pipeline for synthetic phosphoproteomes that could be developed for any organism, tissue, or diseases of interest.

Definitions

The terms "nucleic acid", "polynucleotide" or "oligonucleotide" refer to a DNA molecule, an RNA molecule, or analogs thereof. The terms are generally interchangeable herein, with oligonucleotide generally referring to shorter sequences and polynucleotide generally referring to longer sequences. As used herein, the terms "nucleic acid", "polynucleotide" and "oligonucleotide" include, but are not limited to DNA molecules such as cDNA, genomic DNA, plasmid or vector DNA or synthetic DNA and RNA molecules. Moreover, as used herein, the terms "nucleic acid", "polynucleotide" and "oligonucleotide" include single-stranded and double-stranded forms. A standard convention in the art is that oligonucleotides, polynucleotides, RNA molecules, distinct strands of DNA molecules, and various nucleic acids comprising 2 or more nucleotides are generally numbered from their 5' ends, and this convention is used throughout, including instances of 5' extensions or "overhangs" covalently linked to such molecules.

The term "modification" in the context of an oligonucleotide or polynucleotide includes but is not limited to (a) end modifications, e.g., 5' end modifications or 3' end modifications, (b) nucleobase (or "base") modifications, including replacement or removal of bases, (c) sugar modifications, including modifications at the 2', 3', and/or 4' positions, and (d) backbone modifications, including modification or replacement of the phosphodiester linkages. The term "modified nucleotide" generally refers to a nucleotide having a modification to the chemical structure of one or more of the base, the sugar, and the phosphodiester linkage or backbone portions, including nucleotide phosphates.

As used herein, the term "portion" or "fragment" of a sequence, protein, or oligonucleotide refers to any portion of the sequence (e.g., a nucleotide subsequence or an amino acid subsequence) that is smaller than the complete sequence, protein, or oligonucleotide. Portions of oligonucleotides can be any length, for example, at least 5, 10, 15, 20, 25, 30, 40, 50, 75, 100, 150, 200, 300 or 500 or more nucleotides in length. A portion of a sequence can be about 50%, 40%, 30%, 20%, 10% of the sequence, e.g., one-third of the sequence or shorter, e.g., 7, 6, 5, 4, 3, or 2 nucleotides in length.

As used herein, the terms "protein" and "peptide" refer to polymers or oligomers having a sequence of amino acid subunits joined by peptide bonds. The terms are generally interchangeable herein, with protein generally referring to longer sequences and peptide generally referring to shorter sequences. Accordingly, the term "protein-protein interaction" refers to interactions between two or more proteins or domains thereof, between two or more peptides, or between one or more proteins or domains thereof and one or more peptides, and includes "protein-peptide" interactions and "domain-peptide" interactions. The term "molecular interaction" refers to interactions between two or more molecules, such as protein-protein interactions, protein-lipid interactions, and protein-carbohydrate interactions.

The term "derived from" in the context of a molecule refers to a molecule isolated or made using a parent molecule or information from that parent molecule. For example, a phosphopeptide may be derived from a native phosphoprotein.

The term "substantially identical" in the context of two or more oligonucleotides and/or polynucleotides (or two or more peptides and/or proteins) refers to sequences or subsequences that have at least about 60%, at least about 70%, at least about 80%, at least about 90%, about 90-95%, at least about 95%, at least about 98%, at least about 99% or more nucleotide (or amino acid) sequence identity, when compared and aligned for maximum correspondence using a sequence comparison algorithm or by visual inspection. Preferably, the "substantial identity" between oligonucleotides exists over a region of the oligonucleotides and/or polynucleotides at least about 20 nucleotides in length, at least about 50 nucleotides in length, at least about 100 nucleotides in length, at least about 200 nucleotides in length, at least about 300 nucleotides in length, at least about 500 nucleotides in length, or over the entire length of the and/or polynucleotide. Preferably, the "substantial identity" between two or more peptides and/or proteins exists over a region of the peptides and/or proteins at least about 50 amino acid residues in length, at least about 100 amino acid residues in length, or over the entire length of the peptides and/or proteins.

The term "essentially all" in the context of a phosphoproteome means that all known members of the phosphoproteome are included. Alternatively, at least about 60%, at least about 70%, at least about 80%, at least about 90%, about 90-95%, at least about 95%, at least about 98%, at least about 99% or more known members of the proteome are included.

As disclosed herein, a number of ranges of values are provided. It is understood that each intervening value, to the tenth of the unit of the lower limit, between the upper and lower limits of that range is also specifically contemplated. Each smaller range or intervening value encompassed by a stated range is also specifically contemplated. The term "about" generally refers to plus or minus 10% of the indicated number. For example, "about 10%" may indicate a range of 9% to 11%, and "about 20" may mean from 18-22. Other meanings of "about" may be apparent from the context, such as rounding off, so, for example "about 1" may also mean from 0.5 to 1.4.

The present disclosure describes the design and production of libraries, sets, and kits comprising oligonucleotides encoding essentially all phosphopeptides of a phosphoproteome (that is, all phosphopeptides derived from full proteins in a phosphoproteome). To encode the serine component of the human phosphoproteome, 110,139 previously-observed instances of serine phosphorylation were identified. Singly phosphorylated phosphopeptides containing 16-31 amino acids (also referred to herein as phosphosites) were designed, corresponding to a central pSer residue flanked by 15 amino acids from the parent protein, or fewer for sites close to protein termini. This design is illustrated in (FIG. 1A, FIG. 5A-B). The phosphopeptide sequences were converted into oligonucleotides. Oligonucleotides having lengths of 143-188 nucleotides produced by Agilent Technologies Inc. (using techniques generally described in LeProust, E. M. et al., (2010)) were used to form a library of phosphopeptide-encoding oligonucleotides.

Figure 1B:
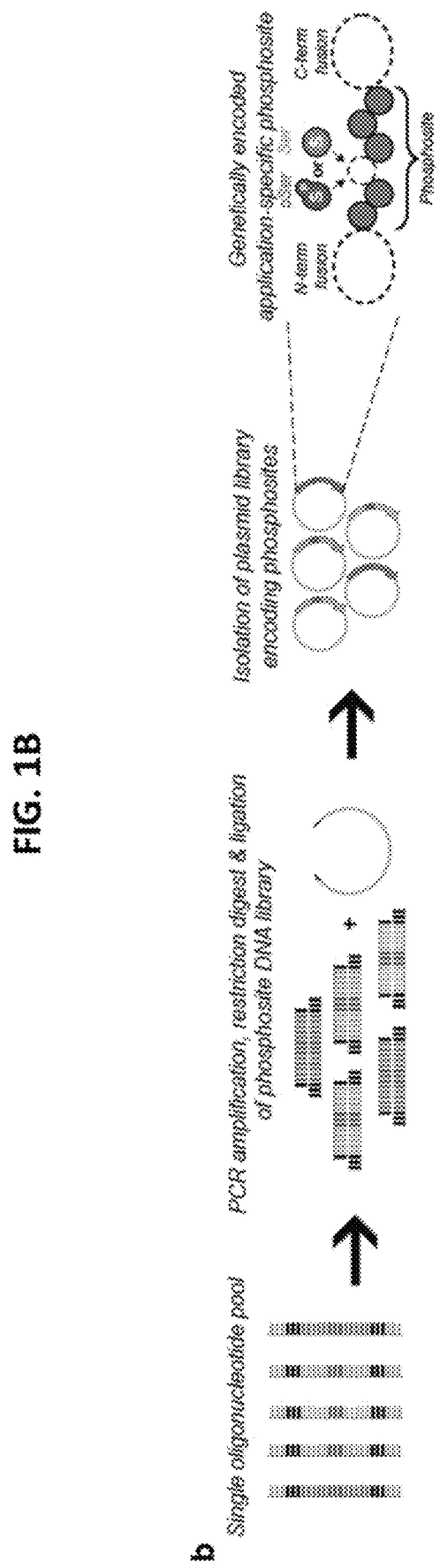
Figure 1C:
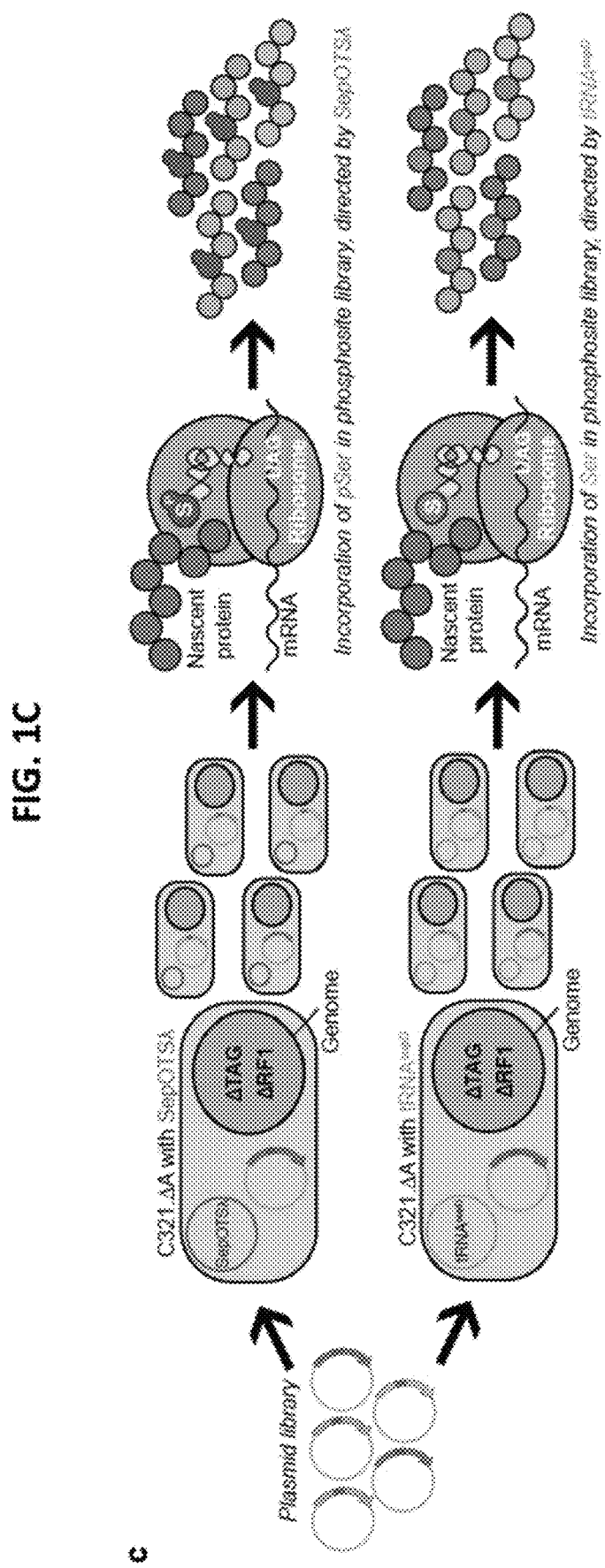

FIGS. 1A and 1B illustrate in more detail the design, synthesis and implementation of a library of phosphopeptide-encoding oligonucleotides that corresponds to a human phosphoproteome. The phosphopeptide-encoding oligonucleotides were designed based on the PhosphoSitePlus database (Hornbeck et al. (2015)) and synthesized as oligonucleotides harboring a central TAG codon to direct pSer or Ser incorporation. Oligonucleotides encoding these phosphosites were synthesized on a programmable DNA microarray and included universal primer annealing and restriction sites, enabling single-pool introduction of the entire phosphosite DNA library into an application-dependent expression vector. FIG. 1C illustrates how separate translation systems (SepOTSλ and tRNA$^{supD}$) were used to incorporate either pSer or Ser into the recombinant phosphoproteome libraries for analysis by mass spectrometry or other downstream applications.

Figure 2A:
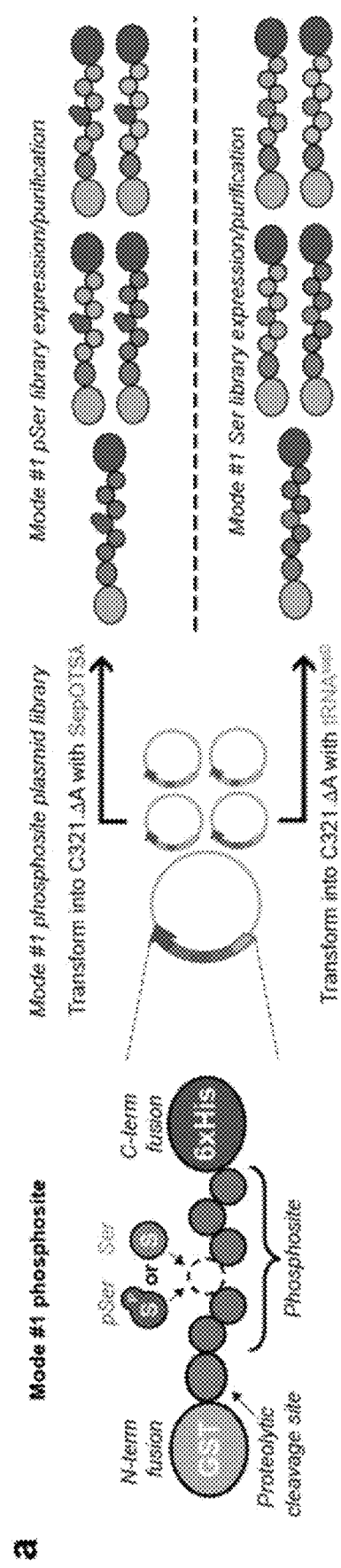
FIGS. 2A to 2D illustrates how a human phosphosite collection was expressed and observed.
Figure 2B:
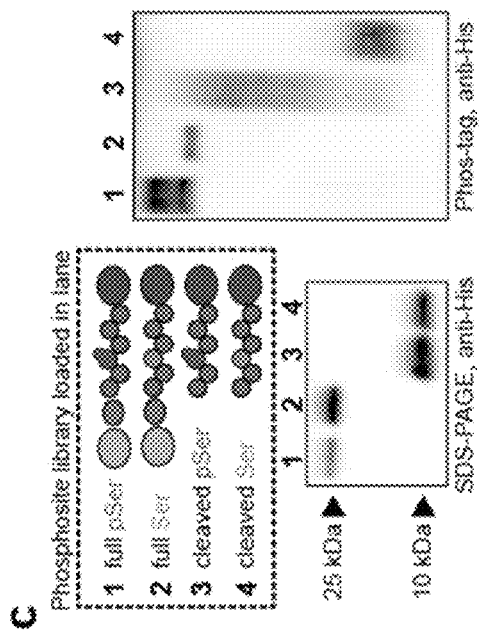
Figure 2C:
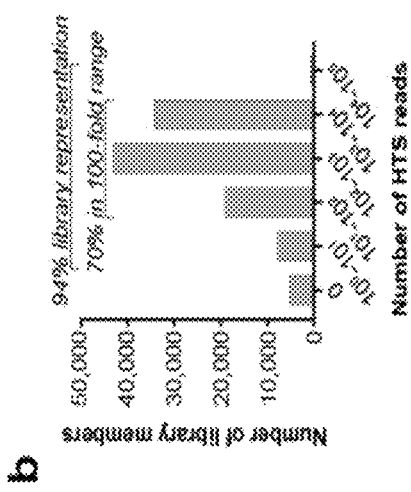
Figure 2D:
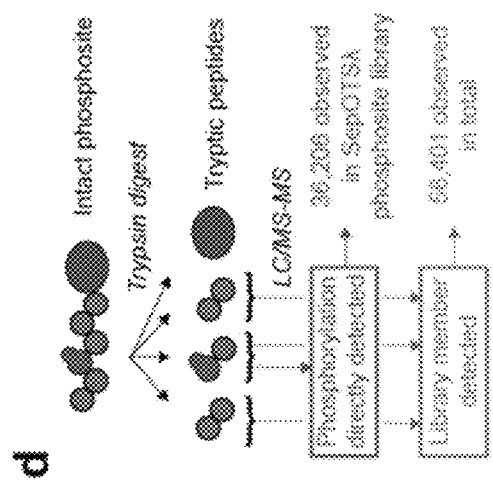

FIG. 2A illustrates how high-level expression of a human phosphosite collection was enabled. First the phosphosite DNA library was introduced into a vector encoding an N-terminal GST fusion tag, a proteolytic cleavage site and a C-terminal 6xHis tag, referred to as mode #1. FIG. 2B shows the plasmid library used for phosphoproteome expression as GST fusion proteins encodes ~94% of the designed recombinant DNAs as determined by high-throughput sequencing (HTS) analysis, with 70% of sequences falling within a 100-fold range of abundance. FIG. 2C shows Western blot from Phos-tag acrylamide gel illustrates broad mobility shift of recombinant pSer-encoding protein library, as both a GST fusion and as enzymatically cleaved short proteins. FIG. 2D shows >36,000 unique phosphopeptides containing pSer at the encoded position were directly observed by LC-MS/MS, and evidence for >56,000 unique protein library members was observed across all samples.

Figure 3A:
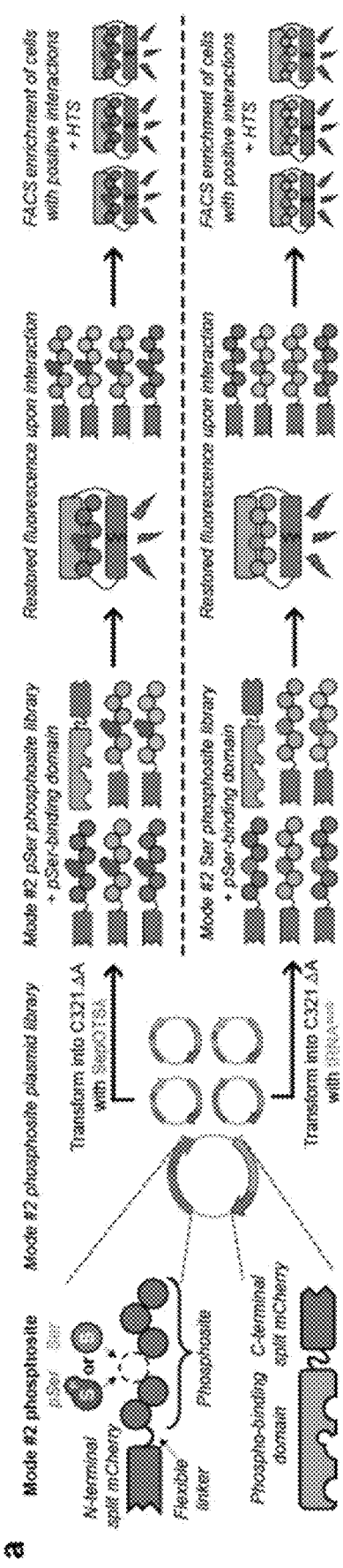
FIGS. 3A to 3G illustrate methods of detecting phosphorylation-dependent protein-proteins interactions with 14-3-3 isoforms using a library of phosphopeptide-encoding oligonucleotides.

FIG. 3A shows an experimental workflow in which a library of phosphopeptide-encoding oligonucleotides is expressed to provide fusion protein comprising a phosphopeptide and a first portion of a reporter (mCherry). A second fusion protein comprising a candidate having a known or suspected phosphoprotein-binding region and a second portion of the reporter is also expressed. A signal from interaction of the first fusion protein and the second fusion protein. Split mCherry in *E. coli* enables identification of protein-protein interactions by restored fluorescence signal. Cells expressing pSer-encoding phosphoproteins that interact with a phospho-binding protein are isolated by FACS. pSer-dependent interactions are assessed by comparing cells expressing either the pSer or Ser protein variant. In FIG. 3A, N-mCh means N-terminal split mCherry; C-mCh means C-terminal split mCherry; and HTS means high-throughput sequencing.

The present disclosure provides a phosphoproteome display technology capable of generating tens of thousands of human phosphoproteins identifiable by mass spectrometry and retaining important binding characteristics of the native human phosphoproteome. This modular synthetic representation of the human serine phosphoproteome can be deployed as a collection of purified fusion proteins or paired with functional domains in the present methods for living screens to reveal novel candidate pSer-mediated protein-protein interactions. Previous work has established the relevance of genetically encoded peptide or protein representations of the human proteome for autoantigen discovery using phage display or as a proteomics standard. Matsumoto, M. et al. A large-scale targeted proteomics assay resource based on an in vitro human proteome. Nature Methods 14, 251-258, doi:10.1038/nmeth.4116 (2016); Larman, B. H. et al. Autoantigen discovery with a synthetic human peptidome. Nature Biotechnology 29, 535-541, doi: 10.1038/nbt.1856 (2011). The present technology builds upon this concept, permitting the targeted synthesis of human-derived phosphoproteins via site-specific incorporation of phosphoserine to probe phosphorylation-specific protein-protein interactions. Compared to other high-throughput pull-down and co-immunoprecipitation techniques (see, for example, Huttlin, E. L. et al. (2017); and Collins, B. C. et al. Quantifying protein interaction dynamics by SWATH mass spectrometry: application to the 14-3-3 system. *Nature Methods* 10, 1246-1253, doi:10.1038/nmeth.2703 (2013)), the present methods for screening phosphorylation-dependent protein interactions is agnostic to cell type and kinase-independent, in contrast to eukaryotic systems. Additionally, phosphorylation in the present library of phosphopeptides is precisely defined by the genetic code and the biological context can be identified by DNA sequencing, thus revealing the amino acid sequence directly responsible for interaction coordination and obviating the need for domain interaction scanning and alanine substitution analysis.

The present disclosure demonstrates novel methods of detecting phosphorylation-dependent protein-protein interactions. The methods recapitulated bona fide interactions and provided a rapid pipeline for identification of novel candidate protein-protein interactions for human phosphorylation-binding proteins of various sizes and binding modalities. The phosphoprotein library is derived from the human phosphoproteome, allowing direct interrogation of an array of physiologically relevant binding sites that are not detectable using motif analysis and bioinformatics approaches, offering distinct advantages over phosphorylation-oriented randomized peptide libraries. See Yaffe, M. B. et al. (1997); and Marx, H. et al. A large synthetic peptide and phosphopeptide reference library for mass spectrometry-based proteomics. *Nature Biotechnology* 31, 557-564, doi:10.1038/nbt.2585 (2013). The present methods were used to identify binding partners that do not fully conform to canonical interaction motifs and identify mixed modes of phosphorylation-dependent and independent binding. The genetically encoded human phosphoproteome is amenable to in vivo selections in *E. coli*, thereby offering a scalable and cost-effective platform capable of interrogating the human serine phosphoproteome. The new methods enable the construction of further targeted disease- or tissue-specific phosphoproteomes or fully synthetic phosphoprotein libraries that can be screened for pSer-dependent binding properties via the present methods.

As one aspect, methods of preparing a library of phosphopeptide-encoding oligonucleotides are provided. The present methods comprise selecting phosphopeptide sequences matching regions of native protein sequences comprising (i) a phosphorylation-susceptible residue and (ii) 0 to 15 residues on each side of the phosphorylation-susceptible residue. The methods also comprise converting the selected phosphopeptide sequences into phosphopeptide-encoding nucleic acid sequences. The method comprises synthesizing a library of phosphopeptide-encoding oligonucleotides having the reverse-translated phosphopeptide-encoding nucleic acid sequences.

Previously, individual recombinant phosphoproteins have been made in *E. coli* for structural/functional studies. A massive DNA library was designed that represents every instance of serine phosphorylation from the human proteome as a new, short protein sequence. This approach for designing short protein sequences representative of human serine phosphorylation sites encoded in *E. coli* codon-optimized oligonucleotides has never been performed before, and the scale and diversity of phosphoprotein synthesis from a single plasmid library (>10,000-fold more complex than previous studies) is a large and unique advance. The deployment of this phosphoprotein library to identify phosphorylation-specific interactions is also a new approach. A single phosphorylation-dependent interaction has previously been detected by BiFC in *E. coli*, though that interaction was not identified. Moreover, it was not based on a human amino acid sequence and did not employ any of the design strategies disclosed herein.

The use of a phosphoprotein library as well as the use of FACS paired with next generation sequencing (an important feature of the present methods of detection and screening) to identify phosphorylation-dependent interactions, including human protein-protein interactions, has never been performed before. Thus, the present approach is the first to identify these types of interactions using BiFC in *E. coli*. The present approach described herein is also uniquely able to site-specifically encode multiple pSER AA at any position of interest at any combination, a capability which has not been achieved previously. The DNA/protein design, recombinant phosphoprotein library synthesis, and application to identify phosphorylation-dependent protein-protein interactions are all novel.

A. Design and Production of Oligonucleotide Library

The present disclosure provides methods of designing and producing a library of phosphopeptide-encoding oligonucleotides are provided. Phosphopeptide sequences are selected from regions of native protein sequences comprising (i) a phosphorylation-susceptible residue and (ii) 0 to 15 residues on each side of the phosphorylation-susceptible residue. For the preparation of the library, the phosphopeptide sequences can be selected by identifying phosphorylation-susceptible amino acid sequences comprising at least one phosphorylation-susceptible residue in full-length native protein sequences, and elongating the phosphorylation-susceptible amino acid sequences to include up to 15 residues from the matching full-length native protein sequences on each side of the phosphorylation-susceptible residue, thereby providing phosphopeptide sequences comprising 16 to 31 residues.

The oligonucleotides were designed such that when they were expressed, pSer or Ser was incorporated into the peptides in a site-specific manner. This is accomplished by employing either the pSer orthogonal translation system (SepOTSλ) or tRNA$^{supD}$ and the native translational machinery, respectively, to suppress UAG codons from the recombinant gene library in a genomically recoded strain of *E. coli* (FIG. 5A). See Pirman, N. L. et al., (2015); Lajoie, M. J. et al. Genomically Recoded Organisms Expand Biological Functions. *Science* 342, 357-360, doi:10.1126/science.1241459 (2013).

Other elements can be included in the phosphopeptide-encoding oligonucleotides. In some embodiments, the phosphopeptide-encoding oligonucleotides comprise primer annealing sites on each side of the phosphopeptide sequences (such as universal primer annealing sites or orthogonal primer annealing sites). This can facilitate amplifying the phosphopeptide-encoding oligonucleotides. In some embodiments, the phosphopeptide-encoding oligonucleotides comprise restriction enzyme cleavage sites on each side of the phosphopeptide-encoding sequences (such as KpnI at the 5' end and HindIII at the 3' end).

Once the converted phosphopeptide-encoding nucleic acid sequences are designed into suitable oligonucleotides, they can be synthesized using a suitable large-scale oligonucleotide production technique. For example, a library of phosphopeptide-encoding oligonucleotides was synthesized by Agilent Technologies, Inc. (Santa Clara, Calif.), using techniques as generally described in LeProust, E. M. et al., (2010). The library had phosphopeptide-encoding oligonucleotides having a length of 143-188 nucleotides and sequence complexity of 110,139 with twofold synthesis redundancy. The oligonucleotides can be amplified and digested with restriction enzymes, then ligated into either a suitable vector.

The present methods of preparing phosphopeptide-encoding oligonucleotides can also comprise ligating the phosphopeptide-encoding oligonucleotides, or an amplification product of the phosphopeptide-encoding oligonucleotides, to vectors or plasmids (such as pNAS1B or pCRT7 or any other vector or plasmid). Also the methods can comprise transforming the vectors into cells (such as bacterial cells, for example *E. coli* cells, preferably C321.ΔA cells or any *E. coli* cells that facilitate recombinant protein expression). Such cells can also contain a plasmid that facilitates ribosomal incorporation of a phosphorylated amino acid into a protein from a codon (such as a SepOTSλ plasmid). Such vectors can be transformed into cells that do not contain a plasmid that facilitates ribosomal incorporation of a phosphorylated amino acid into a protein from a codon (such as a SepOTSλ plasmid).

B. Sets and Kits of Phosphopeptide-Encoding Oligonucleotides

The present disclosure provides sets and kits which are new representations of human phosphoproteins to recapitulate known biology and to discover new biology. A library of phosphopeptide-encoding oligonucleotides (described in more detail in Example 1) was designed with unique, codon-optimized, TAG-containing DNA sequences that do not occur in nature and having every previously-observed instance of serine phosphorylation in the human proteome. In some embodiments, the present sets and kits are new synthetic reagents that represent the human phosphoproteome in a library of synthetic phosphopeptides. These synthetic phosphopeptides are capable of mimicking human biology, as demonstrated herein. These short, human-inspired phosphoproteins do not exist as-is in nature, and have never been designed in this way before. The phosphoprotein design principles and the phosphoproteome library of these unique sequences constitute a novel reagent.

The present sets and kits are also "modular" and by the basic principles of recombinant DNA technology can be appended to any protein sequence and therefore represent a new combinatorial chemistry to manipulate the entire human proteome, or the entire proteome of another species. The present disclosure enables, and reports the successful achievement of, a large-scale design and synthesis of recombinant phosphoproteins of interest for functional studies. The design is also modular for the investigation of phosphorylation in various protein contexts. Genetically encoded phosphoprotein libraries allow for comparative assessment of the function of phosphorylation in tens of thousands of different contexts. Recombinant phosphoprotein libraries have never been made before, and its generation depends on the design principles described herein.

The present methods and materials enable scalable and renewable phosphoprotein synthesis (once the DNA library is constructed, it can be regenerated in *E. coli* indefinitely and used to produce phosphoprotein libraries at virtually any desired scale). The present methods and materials are less expensive than solid-phase peptide synthesis for such diversified peptide sequences. It is believed that no commercially available technology allows such a high level of sequence diversity or long peptide lengths, and would cost drastically more than the present technology. The present methods are also easily adaptable to modification by changing or selecting one or more DNA sequence to study alternative designs or interactions. The peptides can also be subject to evolution (e.g., error-prone PCR) such that the library can serve as a scaffold from which derivatives can be generated and studied.

In some embodiments of the present sets or kits, the oligonucleotides are contained in a plasmid, vector, or cell. In some embodiments, the oligonucleotides are contained in cells comprising a plasmid encoding $tRNA^{supD}$. In some embodiments, the oligonucleotides are contained in a first plasmid or vector in a cell, and the cell also contains a second plasmid or vector encoding $tRNA^{supD}$. In some embodiments, the oligonucleotides are contained in a vector or plasmid encoding $tRNA^{supD}$ (for example, a pNAS1R vector or a pCRT7 vector). In some embodiments, the oligonucleotides are contained in cells comprising a phosphoserine orthogonal translation system.

In some embodiments of the present sets or kits, the set or kit comprises oligonucleotides encoding phosphopeptides corresponding to essentially all proteins susceptible to phosphorylation (which may include multiple phosphopeptides corresponding to a single protein, when that protein can be phosphorylated at multiple different positions), or another group of protein regions susceptible to phosphorylation, such as essentially all eukaryotic proteins, essentially all prokaryotic proteins, essentially all mammalian proteins, essentially all human proteins, essentially all insect proteins, essentially all plant proteins, or a combination thereof. Any of the foregoing can be essentially all proteins susceptible to serine phosphorylation, essentially all proteins susceptible to threonine phosphorylation, essentially all proteins susceptible to tyrosine phosphorylation, or a combination thereof.

The present disclosure provides sets or kits containing many different phosphopeptide-encoding oligonucleotides. The sets or kits can comprise at least 10 different oligonucleotides (alternatively at least 100, 1000, 3,000, 10,000, 30,000, or 100,000 different oligonucleotides). In some embodiments, each of the oligonucleotides comprises one or more codons that codes for a phosphorylated residue in the presence of one or more enzymes or factors (such as Sep aminoacyl-tRNA synthetase and engineered elongation factor Tu). For example, the codon can be TAG or UAG.

In some embodiments of the present sets or kits, the set or kit comprises oligonucleotides encoding essentially all phosphopeptides of a phosphoproteome (that is, all phosphopeptides derived from full proteins in a phosphoproteome) (such as a eukaryotic phosphoproteome, a prokaryotic phosphoproteome, a mammalian phosphoproteome, a human phosphoproteome, an insect phosphoproteome, a plant phosphoproteome, or another phosphoproteome). Any of the foregoing phosphoproteomes can be a serine phosphoproteome, a threonine phosphoproteome, a tyrosine phosphoproteome, or a combination thereof).

In some embodiments of the present sets or kits, the set or kit comprises at least 10 different phosphopeptides (alternatively at least 100, 1000, 3,000, 10,000, 30,000, or 100,000 different phosphopeptides). In some embodiments, each of the phosphopeptides is from 16 to 31 amino acids in length and comprises one or more phosphoserines, phosphotyrosines, a phosphothreonines, or combinations thereof.

C. Reporters And Fusion Proteins

A reporter is employed in many embodiments of the present methods, sets and kits, and it is contemplated that the reporter can be a reporter protein expressed from an oligonucleotide. In some embodiments, the reporter is an enzyme, (such as horseradish peroxidase, beta-galactosidase or alkaline phosphatase), an affinity tag, or a protein that modulates resistance or sensitivity to antibiotics. For example, the reporter protein can be selected from the group consisting of Beta lactamase, DHFR, focal adhesion kinase, Gal4, Horseradish peroxidase, LacZ, luciferase, TEV, and ubiquitin.

In some embodiments, the reporter is a fluorescent protein. For example, in some embodiments of the present methods, sets or kits, each of the oligonucleotides, or a vector or plasmid comprising one of the oligonucleotides or its sequence, further comprises a sequence encoding a reporter protein or portion thereof. For example, the reporter protein can be a fluorescent protein selected from the group consisting of ZsGreen1, ZsYellow1, DsRed2, GFP, eGFP, YFP, eYFP, BFP, eBFP, CFP, eCFP, FP, AmCyan 1, DsRed-Express, AsRed2, HcRed1,mPlum, mCherry, tdTomato, mStrawberry, J-Red, DsRed-monomer, mOrange, mKO, MCitrine, Venus, Ypet, EYFP, Emerald, CyPet, mCFPm, Cerulean, and T-Sapphire. In some preferred embodiments, the fluorescent protein is selected from the group consisting of mCherry, Cerulean, GFP, and YFP.

In some embodiments, the reporters described herein are split so as to be more helpful for the study of phosphorylation-dependent protein-protein interactions. Split reporter proteins can be used to study protein-protein interactions within cells. The reporter protein is split into two portions which are fused to the potentially interacting proteins in the protein-protein interaction of interest, such as a phosphopeptide and a candidate having a known or suspected phosphoprotein-binding region. In the present context, a first fusion protein can comprise a phosphopeptide and a first portion of a reporter, and a second fusion protein can comprise a candidate having a known or suspected phosphoprotein-binding region and a second portion of the reporter. The first fusion protein can be encoded by a first polynucleotide, and the second fusion protein can be encoded by a second polynucleotide. The first and second polynucleotides can be transformed into and expressed within a cell.

In the absence of the protein-protein interaction, the portions of the split-reporter do not reassemble, and a signal from the reporter is not observed. However, if the phosphopeptide and the candidate have sufficient affinity for one another, the resulting protein-protein interaction brings the two portions of the split reporter together, resulting in the reassembly of a functional reporter protein and in a signal. By detecting a signal from interaction of a first fusion protein comprising a phosphopeptide and a second fusion protein comprising a candidate, protein-protein interactions can be identified.

When the reporter is a split fluorescent protein, the signal can be detected by detecting a bimolecular fluorescence complementation (BiFC) signal from interaction of the first fusion protein and the second fusion protein. In some embodiments, the BiFC signal is detected by flow cytometry.

In some embodiments where a fluorescent reporter is used and expressed within a cell, the methods can comprise selecting a cell using Fluorescence-Activated Cell Sorting (FACS) and sequencing the phosphopeptide-encoding region of the first polynucleotide. The methods can also comprise identifying a candidate as having a phosphoprotein-binding region based on a signal from the fluorescent reporter. In some embodiments, the methods can be used to identify the candidate as comprising an unrecognized phosphoprotein-binding motif.

In some embodiments of the present sets or kits, each polynucleotide further comprises a sequence encoding an affinity tag selected from the group consisting of glutathione s-transferase (GST) tags, maltose binding protein (MBP), chitin binding protein, cellulose-binding protein, calmodulin binding peptide, streptavidin binding peptide (SBP), poly-arginine, poly-histidine, FLAG (DYKDDDDK) (SEQ ID NO:62), 3x FLAG, streptavidin (strep)-tag II, c-myc, RNaseA S-peptide (S-tag), natural histidine affinity tag (HAT), alkaline phosphatase (ALP), J3-D-galactosidase, beta-D-glucose oxidase, luciferase, peroxidase, and xanthine oxidase.

D. Methods of Detecting And Screening Candidates For Protein-Protein Interactions The present disclosure also provides methods for screening candidates for a phosphorylation-dependent protein-protein interaction. The methods comprise providing a first fusion protein comprising a phosphopeptide and a first portion of a reporter; providing a second fusion protein comprising a candidate having a suspected phosphoprotein-binding region and a second portion of the reporter; detecting a signal from interaction of the first fusion protein and the second fusion protein; and identifying the candidate as having a phosphopeptide-binding region.

In some embodiments of the present screening methods, the candidate is an antibody or antibody-like protein of known or unknown phosphoprotein-binding properties. In some embodiments, the present screening method also comprises identifying the candidate as comprising an unrecognized phosphoprotein-binding motif. The interaction can be detected inside a cell or outside a cell (for example, in protein extracts).

In some embodiments, the first fusion protein is expressed within a cell by a first polynucleotide transformed into the cell, and the first polynucleotide comprises a phosphopeptide-encoding portion. In some embodiments, the second fusion protein is expressed within the cell by a second polynucleotide transformed into the cell.

The present screening methods can also comprise sequencing the first polynucleotide from a cell having an identified candidate for a phosphorylation-dependent protein-protein interaction. In some embodiments, the second polynucleotide from a cell having an identified candidate is also sequenced, to identify a region encoding the phosphoprotein-binding region.

In some embodiments of the present screening methods, the reporter is a fluorescent protein, and the signal is detected by detecting a bimolecular fluorescence complementation (BiFC) signal from interaction of the first fusion protein and the second fusion protein. For example, the BiFC signal can be detected by flow cytometry, wherein the first and second fusion proteins are encoded by first and second polynucleotides within a cell. The present methods can also comprise selecting a cell using Fluorescence-Activated Cell Sorting (FACS) and sequencing the phosphopeptide-encoding region encoded by the first polynucleotide, or the phosphoprotein-binding region encoded by the second polynucleotide, or both of the first and second polynucleotides.

Bimolecular fluorescence complementation (BiFC) techniques have been successfully used to capture and report protein-protein interactions. Ghosh, I., et al., Antiparallel Leucine Zipper-Directed Protein Reassembly: Application to the Green Fluorescent Protein. *Journal of the American Chemical Society* 122, 5658-5659, doi:10.1021/ja994421w (2000). This approach was recently shown to be effective in *E. coli* and to function with the genetically encoded phosphoserine technology. Sawyer, N. et al. Designed Phosphoprotein Recognition in *Escherichia coli*. *ACS Chemical Biology* 9, 2502-2507, doi:10.1021/cb500658w (2014). The present disclosure adapts the above approaches in combination with the library of phosphopeptide-encoding oligonucleotides to develop the present methods, including a proximity capture method that enables identification of phosphorylation-dependent protein-protein interactions from the human serine phosphoproteome or other phosphoproteomes.

In the present methods, the modular recombinant phosphoprotein library described herein allows the importation of phosphoprotein cassettes into various genetic modules to generate a vast, phosphorylated "prey" library. The present methods then allow the introduction of any protein domain as "bait" whereby all productive "bait-prey" interactions will reconstitute mCherry fluorescence in living cells, which are then isolated by fluorescence-activated cell sorting (FACS) followed by analysis using high-throughput DNA sequencing to identify candidate pSer-dependent interactions (FIG. 2A).

Libraries

In one aspect, the present invention provides a library of phosphopeptides or phosphopeptide-encoding oligonucleotides. In certain embodiments, the library contains two or more phosphopeptides or oligonucleotides as disclosed herein. The library can contain from about 10 to about $10^7$ individual members, e.g., about 10 to about $10^2$, about $10^2$ to about $10^3$, about $10^3$ to about $10^5$, from about $10^5$ to about $10^7$ members. An individual member of a phosphopeptide library differs from other members of the library at least in the peptide sequence, i.e., at least one amino acid in an individual member is different from an amino acid at the same position in another member. Similarly, an individual member of a phosphopeptide-encoding oligonucleotide library differs from other members of the library at least in the encoded peptide sequence, i.e., at least one amino acid encoded by in an individual member is different from an amino acid encoded at the same position in another member.

In some embodiments, the library comprises at least $10^2$ unique peptides or oligonucleotides. In some embodiments, the library comprises at least $10^3$ unique peptides or oligonucleotides. In some embodiments, the library comprises at least $10^4$ unique peptides or oligonucleotides. In some embodiments, the library comprises at least $10^5$ unique peptides or oligonucleotides. In some embodiments, the library comprises at least $10^6$ unique peptides or oligonucleotides.

Oligonucleotide Synthesis

In certain embodiments, synthesis of the oligonucleotides may be conducted on a solid support having a surface to which chemical entities may bind. In some embodiments, oligonucleotides being synthesized are attached, directly or indirectly, to the same solid support and may form part of an array. An "array" is a collection of separate molecules of known monomeric sequence each arranged on a solid support in a spatially defined and a physically addressable manner, such that the location of each sequence is known. An "array," or "microarray" used interchangeably herein includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. An array is "addressable" when it has multiple regions of different moieties (e.g., different polynucleotide sequences) such that a region (i.e., a "feature" of the array) at a particular predetermined location (i.e., an "address") on the array will detect a particular target or class of targets (although a feature may incidentally detect non-targets of that feature). Array features are typically, but need not be, separated by intervening spaces. The number of features that can be contained on an array will largely be determined by the surface area of the substrate, the size of a feature and the spacing between features. Arrays can have densities of up to several hundred thousand or more features per $cm^2$, such as 2,500 to 200,000 features/$cm^2$. The features may or may not be covalently bonded to the substrate.

Suitable solid supports may have a variety of forms and compositions and derive from naturally occurring materials, naturally occurring materials that have been synthetically modified, or synthetic materials. Examples of suitable support materials include, but are not limited to, silicas, silicon and silicon oxides, teflons, glasses, polysaccharides such as agarose (e.g., Sepharose® from Pharmacia) and dextran (e.g., Sephadex® and Sephacyl®, also from Pharmacia), polyacrylamides, polystyrenes, polyvinyl alcohols, copolymers of hydroxyethyl methacrylate and methyl methacrylate, and the like. In some embodiments, the solid support is a plurality of beads.

The initial monomer of the oligonucleotide to be synthesized on the substrate surface can be bound to a linker which in turn is bound to a surface hydrophilic group, e.g., a surface hydroxyl moiety present on a silica substrate. In some embodiments, a universal linker is used. In some other embodiments, the initial monomer is reacted directly with a surface hydroxyl moiety, surface amine or other reactive functional group. Alternatively, oligonucleotides can be synthesized first, and attached to a solid substrate post-synthesis by any method known in the art. Thus, the present disclosure can be used to prepare arrays of oligonucleotides wherein the oligonucleotides are either synthesized on the array, or attached to the array substrate post-synthesis. Subsequently, the oligonucleotides or a pool or a plurality of pools of ologonucleotides can optionally and selectively be cleaved from the array substrate and be used as a library or libraries.

In certain embodiments, a peptide or an oligonucleotide is provided in purified or isolated form. In certain embodiments, a peptide or an oligonucleotide is provided at a purity of at least about 80%, or at least about 90%, or at least about 95%, or at least about 99% purity. In certain embodiments, a peptide or an oligonucleotide is provided as part of a composition. In certain embodiments, a peptide or an oligonucleotide is provided in aqueous compositions suitable for use as, or inclusion in, a composition for a reaction. Those of skill in the art are well aware of the various substances that can be included in reaction compositions.

In certain embodiments, a phosphopeptide is provided as a recombinant polypeptide. In certain examples, the recombinant polypeptide is prepared as a fusion protein. For example, in certain embodiments, a nucleic acid encoding the phosphopeptide is linked to another nucleic acid encoding a fusion partner, e.g., glutathione-S-transferase (GST), 6x-His epitope tag, or M13 Gene 3 protein. Suitable host cells can be used to express the fusion protein. In certain embodiments, the fusion protein is isolated by methods known in the art. In certain embodiments, the fusion protein can be further treated, e.g., by enzymatic digestion, to remove the fusion partner and obtain the phosphopeptide. Alternatively, phosphopeptides can be made with recombinant technology using a host cell system or an in vitro translation-transcription system known in the art. Details of such systems and technology can be found in e.g., WO2014144761 WO2014144592, WO2013176772, US20140273226, and US20140273233, the contents of which are incorporated herein by reference in their entireties.

Fusion Proteins

In certain embodiments, the phosphopeptide is fused to another protein or polypeptide heterologous to the phosphopeptide to create a fusion protein. In certain embodiments, the heterologous sequence includes one or more effector domains, such as a cleavage domain, a transcriptional activation domain, a transcriptional repressor domain, or an epigenetic modification domain. Additional examples of the effector domain include a nuclear localization signal, cell-penetrating or translocation domain, or a marker domain. In certain embodiments, the effector domain is located at the N-terminal, the C-terminal, or in an internal location of the fusion protein. In certain embodiments, the phosphopeptide of the fusion protein is or is derived from a phosphopeptide.

In certain embodiments, the fusion protein comprises a reporter or a portion of a marker. Non-limiting examples of markers include fluorescent proteins, purification tags, and epitope tags. In certain embodiments, the marker is a fluorescent protein. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1,), blue fluorescent proteins (e.g. EBFP, EBFP2, Azurite, mKalamal, GFPuv, Sapphire, T-sapphire,), cyan fluorescent proteins (e.g. ECFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), orange fluorescent proteins (mOrange, mKO, Kusabira-Orange, Monomeric Kusabira-Orange, mTangerine, tdTomato) and any other suitable fluorescent protein. In certain embodiments, the marker domain is a purification tag and/or an epitope tag. Exemplary tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6xHis, biotin carboxyl carrier protein (BCCP), and calmodulin.

A kit or system may contain, in an amount sufficient for at least one assay or experiment, any combination of the components described herein (where the components can be phosphopeptide-encoding oligonucleotides, vectors, plasmids, cells, phosphopeptides, or other materials described herein). In some applications, one or more components may be provided in pre-measured single use amounts in individual, typically disposable, tubes or equivalent containers. The amount of a component supplied in the kit can be any appropriate amount and may depend on the market to which the product is directed. The container(s) in which the components are supplied can be any conventional container that is capable of holding the supplied form, for instance, microfuge tubes, microtiter plates, ampoules, bottles, or integral testing devices, such as fluidic devices, cartridges, lateral flow, or other similar devices.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like). The kits may further include instructions recorded in a tangible form for use of the components.

EXAMPLES

Example 1

In this example, a library of phosphopeptide-encoding oligonucleotides was prepared. 15-residue amino acid sequences corresponding to previously observed phosphorylation sites across the human proteome were downloaded from PhosphoSitePlus on 11 Jan. 2015. See Hornbeck, P. V. et al. PhosphoSitePlus: a comprehensive resource for investigating the structure and function of experimentally determined post-translational modifications in man and mouse. *Nucleic Acids Research* 40, doi:10.1093/nar/gkr1122 (2012). Entries were filtered to include only human proteins containing phosphoserine at the central position, and duplicate entries were removed. The 15-residue sequences were then matched to corresponding full-length human proteins and elongated to contain 31 amino acids (15 on either side of the phosphoserine residue). If phosphoserine occurred within 15 residues of the N- or C-terminus, the peptide sequence was extended to the end of the protein. Using Geneious software, amino acid sequences were reverse translated and codon optimized for *Escherichia coli* K12 (high). The central phosphoserine residue was encoded as TAG. Other post-translational modifications were not taken into account. KpnI followed by an AAG (Lys) codon were encoded at the 5' end of the genes, while HindIII was included at the 3' end.

The sequences of primer pairs used to PCR amplify the DNA library were previously described. Kosuri, S. et al. Scalable gene synthesis by selective amplification of DNA pools from high-fidelity microchips. *Nature Biotechnology* 28, 1295-1299, doi:10.1038/nbt.1716 (2010). Individual primers were blasts searched against the DNA library for entries containing high sequence homology (https://blast.ncbi.nlm.nih.gov/Blast.cgi). The $\Delta T_m$ between primer-specific and non-specific library sequences was ensured to be ≥15° C. to reduce non-specific amplicons (https://www.idtdna.com/calc/analyzer). Ten sets of 20 by orthogonal primer annealing sequences were encoded in the library to facilitate amplification of DNA subpools, and one set of 20 bp universal primer annealing sequences was encoded in every DNA sequence at the 5' and 3' termini (Table A). This resulted in 110,139 DNA library sequences between 143 and 188 bp in length.

TABLE A

| ID | Primer sequence | | $T_m$ (° C.) | # blastn results | Highest $T_m$ of blastn results (° C.) | $\Delta T_m$ (° C.) |
|---|---|---|---|---|---|---|
| 1F | ACCCAAAGAACTCGATTCCT | (SEQ ID NO: 1) | 53.7 | 3086 | 37.2 | 16.5 |
| 1R | ATGGAGGTCCTTTTGTTCCT | (SEQ ID NO: 2) | 53.7 | 1229 | 33.4 | 20.3 |
| 2F | AGCGTCGAATGAATGCATAC | (SEQ ID NO: 3) | 53.3 | 566 | 38.2 | 15.1 |
| 2R | AACTTCAGGGCTGTGTCTAA | (SEQ ID NO: 4) | 53.6 | 1428 | 38.6 | 15.0 |
| 3F | AGACCAGGATGGCTGATAAG | (SEQ ID NO: 5) | 53.8 | 2554 | 32.7 | 21.1 |
| 3R | GTTTCGTGCCCACATATACC | (SEQ ID NO: 6) | 53.6 | 414 | 33.4 | 20.2 |
| 4F | AATCCTTGCGTCAATGGTTC | (SEQ ID NO: 7) | 53.5 | 238 | 37.9 | 15.6 |
| 4R | GGGTTCTCGGATTTTACACG | (SEQ ID NO: 8) | 53.5 | 6096 | 34.3 | 19.2 |
| 5F | TGTCGTGCCTCTTTATCTGT | (SEQ ID NO: 9) | 53.6 | 282 | 33.8 | 19.8 |
| 5R | GCTTCGGTGTATCGGAAATG | (SEQ ID NO: 10) | 53.8 | 4943 | 38.1 | 15.7 |
| 6F | TATTCATGCTTGGACGGACT | (SEQ ID NO: 11) | 53.7 | 285 | 34.5 | 19.2 |
| 6R | ACTATGTACCGCTTGTTGGA | (SEQ ID NO: 12) | 53.6 | 1152 | 26.2 | 27.4 |
| 7F | TTCCGTTTATGCTTTCCAGC | (SEQ ID NO: 13) | 53.5 | 2615 | 35.5 | 18.0 |

TABLE A-continued

| ID | Primer sequence | | $T_m$ (° C.) | # blastn results | Highest $T_m$ of blastn results (° C.) | $\Delta T_m$ (° C.) |
|---|---|---|---|---|---|---|
| 7R | TCCTTGGAGTTTAGAGCGAG | (SEQ ID NO: 14) | 53.9 | 2344 | 27.5 | 26.4 |
| 8F | TGCAAGTGTACAAATCCAGC | (SEQ ID NO: 15) | 53.4 | 1595 | 23.2 | 30.2 |
| 8R | GAACGGTGATCCCTTTCCTA | (SEQ ID NO: 16) | 54 | 3677 | 34.3 | 19.7 |
| 9R | GAGATGAGTAGACGAGTGGG | (SEQ ID NO: 17) | 53.9 | 27 | 31.6 | 22.3 |
| 9R | ATGGTCACTGACTCGCATTA | (SEQ ID NO: 18) | 53.6 | 431 | 36.5 | 17.1 |
| 10F | TGTCATATGCTAACGTCCGT | (SEQ ID NO: 19) | 53.6 | 4037 | 37.0 | 16.6 |
| 10R | TGGCTACTTTCTTAGCGGAA | (SEQ ID NO: 20) | 53.6 | 2729 | 34.7 | 18.9 |
| END-F | TTATAATCATCCTCCCCGGC | (SEQ ID NO: 21) | 54 | 45 | 15.8 | 38.2 |
| END-R | CCAAATAGGATGTGTGCTCG | (SEQ ID NO: 22) | 53.6 | 236 | 34.4 | 19.2 |

The gene library was produced using an oligonucleotide library synthesized by Agilent Technologies having a length of 143-188 nucleotides and sequence complexity of 110,139 with twofold synthesis redundancy. LeProust, E. M. et al. Synthesis of high-quality libraries of long (150 mer) oligonucleotides by a novel depurination controlled process. Nucleic acids research 38, 2522-2540 (2010). DNA was provided as a 10 pmol lyophilized pool. Phosphoprotein genes were PCR amplified in a single pool using primers End-F and End-R (Table A). The PCR product was then extracted on a 2% agarose gel, digested with KpnI and HindIII restriction enzymes and ligated into either the pNAS1B or pCRT7 vectors modified as described in more detail below. The ligation reaction was desalted by drop dialysis (V-Series membrane, Millipore) and then transformed into ElectroMAX DH10B cells by electroporation (1 mm cuvette using Gene Pulser Xcell from Bio-Rad, 1800 V 200 W 25 mF), and recovered in 700 µL SOC medium for 1 h at 37° C., 230 rpm. The transformation mixture was then inoculated directly into 50 mL LB with 100 ng/µL ampicillin and grown overnight at 37° C., 230 rpm, and the plasmid library was isolated by miniprep (Omega Bio-tek).

The modified C321.ΔA strain used in this example and the following examples, and the SepOTSλ and tRNA$^{supD}$-encoding plasmids, are available from Addgene. Pirman, N. L. et al. A flexible codon in genomically recoded Escherichia coli permits programmable protein phosphorylation. Nature communications 6, 8130, doi:10.1038/ncomms9130 (2015). For all Hi-P experiments, a new tRNA$^{supD}$ plasmid was generated by removing the four tRNA$^{Sep}$ genes from the SepOTSγ plasmid (containing SepRS9-EFSep21) (see Pirman et al. (2015) and Lee, S. et al. A Facile Strategy for Selective Incorporation of Phosphoserine into Histones. Angewandte Chemie 125, 5883-5887, doi:10.1002/ange.201300531 (2013)) by NotI restriction digest and replacing them with two gene copies of tRNA$^{supD}$ from the original supD plasmid so comparisons between pSer- and Ser-encoding proteins were performed in isogenic plasmids/strains except for the tRNA$^{Sep}$/tRNA$^{supD}$ locus.

Phosphoprotein fusion proteins were encoded in the pCRT7 Topo tetR pLtetO vector (see Pirman et al. (2015)) with the following modifications: XbaI and HindIII enzymes were used to remove the tetR, pLtetO and recombinant protein expression loci from pCRT7. In parallel, a multiple cloning site containing pBAD, ribosome binding site, and an NdeI site (G1, Table B) were introduced between BamHI and SacI sites in the pNAS1B vector. Sawyer, N. et al. Designed Phosphoprotein Recognition in Escherichia coli. ACS Chemical Biology 9, 2502-2507, doi:10.1021/cb500658w (2014).

TABLE B

| ID | Purpose | Sequence (5' to 3') |
|---|---|---|
| G1 | Addition of MCS to pNAS vector by NdeI/SacI digest | CGGGATCCTACCTGACGCTTTTTATCGCAACTCTCTACT GTTTCTCCATACCCGTTTTTGGGCTAACAGGAGGAATT ACATATGTCTAGAGTTTAAACCGGACCGTGTACATTATA AGAGCTCCCG (SEQ ID NO: 23) |
| G2 | NEDD4 WW2-C-terminal mCherry | GAGGAATTACATATGTCAGGCTTACCGCCCGGATGGGAA GAAAAACAAGATGAGCGCGGTCGCTCTTACTACGTCGAT CACAATTCCCGTACAACAACTTGGACGAAGCCCACTGTG GAGCTCGGAGCGGCTGCAGGAGGAAGCGGAGGCGCGCTG AAGGGCGAGATCAAGCAGAGGCTGAAGCTGAAGGACGGC GGCCACTACGACGCTGAGGTCAAGACCACCTACAAGGCC AAGAAGCCCGTGCAACTGCCCGGCGCCTACAACGTCAAC ATCAAGTTGGACATCACCTCCCACAACGAGGACTACACC ATCGTGGAACAGTACGAACGCGCCGAGGGCCGCCACTCC ACCGGCGGCATGGACGAGCTGTACAAGCACCACCACCAC CACCACTAATTATAAAAAAAA (SEQ ID NO: 24) |

TABLE B-continued

| ID | Purpose | Sequence (5' to 3') |
|---|---|---|
| G3 | NEDD4 WW2 gene with NdeI/SacI restriction sites (other irrelevant genes also encoded) | GTCCATATGTCACCCCTTCCGCCAGGTTGGGAAGAGCGT CAAGACATCCTGGGTCGTACTTATTACGTTAACCACGAG TCACGTCGCACCCAGTGGAAGCGTCCAACACCGGAGCTC ATCGGTCATATGGGATTTTTGCCGAAGGGGTGGGAGGTC CGTCATGCGCCCAATGGTCGTCCATTTTTCATCGACCAC AACACAAAGACTACGACGTGGGAGGACCCACGCCTTGAG CTCTACTGGCATATGGGGCCTCTTCCCCCCGGATGGGAG GAACGCACTCACACTGATGGACGCATTTTTTATATCAAT CACAACATTAAGCGCACGCAATGGGAGGACCCACGCTTG GAGCTCTGGAACCATATGCCGGGATTACCGAGCGGATGG GAAGAACGCAAAGATGCCAAAGGGCGTACCTACTATGTG AACCATAACAATCGCACTACGACATGGACGCGCCCCATT ATGGAGCTCTAC (SEQ ID NO: 25) |
| G4 | 14-3-3β gene with NdeI/SacI restriction sites | GAGTCACTCATATGACGATGGACAAATCAGAGCTGGTAC AGAAGGCAAAACTGGCTGAACAAGCTGAGCGTTACGACG ACATGGCGGCTGCAATGAAGGCGGTTACGGAACAAGGGC ACGAGCTGAGTAATGAGGAACGCAACTTATTAAGTGTTG CGTACAAAAATGTAGTCGGCGCACGTCGTAGTAGTTGGC GCGTTATCAGCAGTATTGAGCAGAAAACCGAGCGCAACG AGAAGAAGCAACAAATGGGTAAAGAATACCGTGAAAAGA TCGAAGCCGAACTGCAGGATATTTGTAATGATGTGCTTG AATTGCTGGATAAGTACTTGATCCCCAACGCTACACAAC CCGAATCGAAAGTTTTTTACCTTAAAATGAAGGGCGACT ATTTTCGCTATCTTAGCGAGGTGGCTAGTGGTGATAACA AGCAAACCACCGTGTCAAACTCGCAACAAGCATACCAGG AAGCATTCGAGATTAGCAAGAAGGAGATGCAGCCCACGC ACCCTATCCGTTTGGGCCTTGCCCTGAATTTCTCAGTTT TCTACTACGAAATCTTGAACTCTCCAGAGAAAGCGTGCT CGCTGGCCAAAACGGCTTTTGACGAGGCTATCGCAGAAT TGGACACACTGAATGAGGAAAGCTATAAAGATTCGACAC TTATTATGCAGTTATTACGTGATAATCTTACACTGTGGA CCAGCGAGAACCAAGGCGACGAAGGGGACGCTGGAGAAG GAGAGAACGAGCTCAGTCAGTC (SEQ ID NO: 26) |
| G5 | 14-3-σ gene with NdeI/SacI restriction sites | GAGTCACTCATATGGAACGCGCGTCTTTAATTCAGAAAG CCAAGTTAGCTGAGCAGGCGGAGCGTTACGAAGACATGG CAGCGTTTATGAAAGGCGCCGTCGAGAAAGGGGAAGAAT TATCGTGTGAAGAGCGCAATTTGTTGTCAGTGGCATACA AAAATGTCGTGGGTGGTCAGCGTGCAGCGTGGCGTGTGC TGAGCAGTATCGAACAAAAGTCAAATGAGGAAGGTTCCG AAGAAAAAGGCCCCGAAGTTCGCGAGTATCGTGAGAAGG TTGAGACTGAGCTGCAAGGGGTTTGCGACACCGTGCTTG GACTGCTGGACTCCCACTTGATTAAAGAAGCGGGTGATG CCGAATCCCGTGTCTTCTACTTAAAAATGAAGGGGGACT ATTACCGTTATTTAGCCGAGGTAGCAACGGGCGACGACA AAAAGCGTATTATCGACTCAGCTCGTTCTGCCTATCAGG AAGCGATGGATATTTCAAAGAAAGAGATGCCACCCACAA ATCCAATTCGTCTTGGATTGGCGTTAAATTTCTCCGTGT TTCACTACGAGATCGCGAATTCACCGGAGGAAGCGATTT CTCTGGCAAAGACAACATTTGACGAGGCTATGGCTGACC TTCACACACTTTCGGAGGACTCGTATAAAGATTCCACCT TGATTATGCAACTTCTGCGCGACAATTTGACGCTTTGGA CCGCCGATAACGCAGGTGAGGAGGGTGGCGAAGCGCCTC AAGAGCCCCAATCCGAGCTCAGTCAGTC (SEQ ID NO: 27) |
| G6 | N-terminal mCherry-phosphosite cassette | GCACTGACCGAATTCATTAAAGAGGAGAAAGGTTCCATG GCATCCGTGAGCAAGGGCGAGGAGGATAACATGGCCATC ATCAAGGAGTTCATGCGCTTCAAGGTGCACATGGAGGGC TCCGTGAACGGCCACGAGTTCGAGATCGAGGGCGAGGGC GAGGGCCGCCCCTACGAGGGCACCCAGACCGCCAAGCTG AAGGTGACCAAGGGTGGCCCCCTGCCCTTCGCCTGGGAC ATCCTGTCCCCTCAGTTCATGTACGGCTCCAAGGCCTAC GTGAAGCACCCCGCCGACATCCCCGACTACTTGAAGCTG TCCTTCCCCGAGGGCTTCAAGTGGGAGCGCGTGATGAAC TTCGAGGACGGCGGCGTGGTGACCGTGACCCAGGACTCC TCCCTGCAGGACGGCGAGTTCATCTACAAGGTGAAGCTG CGCGGCACCAACTTCCCCTCCGACGGCCCCGTAATGCAG AAGAAGACCATGGGCTGGGAGGCCTCCTCCGAGCGGATG TACCCCGAGGACGGTGGCTCTGGCTCTGGGTCGACTGGT GGTACCGGCGCCAAAtctgacAAGCTTTAACAGCTGAAA AAA (SEQ ID NO: 28) |

The araC and pBAD regions from the modified pNAS1B plasmid were excised using SphI and XhoI enzymes. This insert and the XbaI/HindIII-digested pCRT7 vector were blunted using a Quick Blunting™ Kit (NEB) and heated together. Then, primers P1 and P2 (Table C) were used to amplify an N-terminal GST fusion tag and a human rhinovirus 3C proteolytic cleavage site from the pGEX6P-1 encoding a GST fusion protein, and adding a multiple cloning site with KpnI and HindIII sites, a 6xHis tag and a TAA stop codon. Primers P3 and P4 (Table C) were used to add NdeI and SacI sites to the P1/P2 PCR product via secondary PCR amplification.

phoprotein genes were subsequently inserted via KpnI/HindIII sites (between the proteolytic cleavage site and 6xHis tag).

Example 1A

FIG. 5A illustrates pSer- and Ser-containing phosphoproteins being expressed in cells harboring the SepOTSλ or tRNA$^{supD}$, respectively. The SepOTSλ relies on tRNA$^{Sep}$ that can suppress UAG codons, pSer-tRNA$^{Sep}$ synthetase SepRS and engineered elongation factor EF-Tu. Ser incorporation at UAG relies only on supplementation of tRNA$^{supD}$ and otherwise utilizes the endogenous translation

TABLE C

| ID | Purpose | Sequence (5' to 3') |
|---|---|---|
| P1 | To amplify GST + HRV3C | GCATTGCGAATTCATTAAAGAGGAGAAAGGAACCATGTCCCCTATACTAGGTTATGG (SEQ ID NO: 29) |
| P2 | To amplify GST + HRV3C with added MCS, 6xHis, and stop codon | GTACAGCCTAGGTTAATGATGGTGGTGGTGGTGAAGCTTGTCAGATTTGGCGCCGGTACCGGGCCCCTGGAACAGAACTTC (SEQ ID NO: 30) |
| P3 | To add NdeI site to P1/P2 PCR product | GACTGTCATATGTCCCCTATACTAGGTTATTGG (SEQ ID NO: 31) |
| P4 | To add SacI site to P1/P2 PCR product | CAGTCAGAGCTCTTAATGATGGTGGTGGTGGTG (SEQ ID NO: 32) |
| P5 | To remove SacI site next to PsiI | AGTCAGTTATAACAGCTCTTGGCTGTTTTGGCGG (SEQ ID NO: 33) |
| P6 | To remove SacI site next to PsiI | TGAACTCGAGGAGTTTGTAGAAACGC (SEQ ID NO: 34) |
| P7 | To change HindIII site in modified pNAS vector | GCAGCACGCGTACCATGTAGCTTAATCAGCTGTTA (SEQ ID NO: 35) |
| P8 | To change HindIII site in modified pNAS vector | TAACAGCTGATTAAGCTACATGGTACGCGTGCTGC (SEQ ID NO: 36) |
| P9 | PCR amplification of phosphosite libraries for HTS | NNNNNNNAGTCTGGGTCGACTGGTGGTACC (SEQ ID NO: 37) |
| P10 | PCR amplification of phosphosite libraries for HTS | NNNNNNNNNAGCGTACCATGTAGCTTAATCAGCTGTTAAAGCTT (SEQ ID NO: 38) |
| P11 | PCR amplification of phosphosite libraries for HTS | NNNNNNNTCTCTGGGTCGACTGGTGGTACC (SEQ ID NO: 39) |
| P12 | PCR amplification of phosphosite libraries for HTS | NNNNNNNNTCCGTACCATGTAGCTTAATCAGCTGTTAAAGCTT (SEQ ID NO: 40) |
| P13 | PCR amplification of phosphosite libraries for HTS | NNNNNNNNGATCTGGGTCGACTGGTGGTACC (SEQ ID NO: 41) |
| P14 | PCR amplification of phosphosite libraries for HTS | NNNNNNNGACGTACCATGTAGCTTAATCAGCTGTTAAAGCTT (SEQ ID NO: 42) |
| P15 | PCR amplification of phosphosite libraries for HTS | NNNNNNNNNCTTCTGGGTCGACTGGTGGTACC (SEQ ID NO: 43) |
| P16 | PCR amplification of phosphosite libraries for HTS | NNNNNNCTCGTACCATGTAGCTTAATCAGCTGTTAAAGCTT (SEQ ID NO: 44) |

Figure 5D:
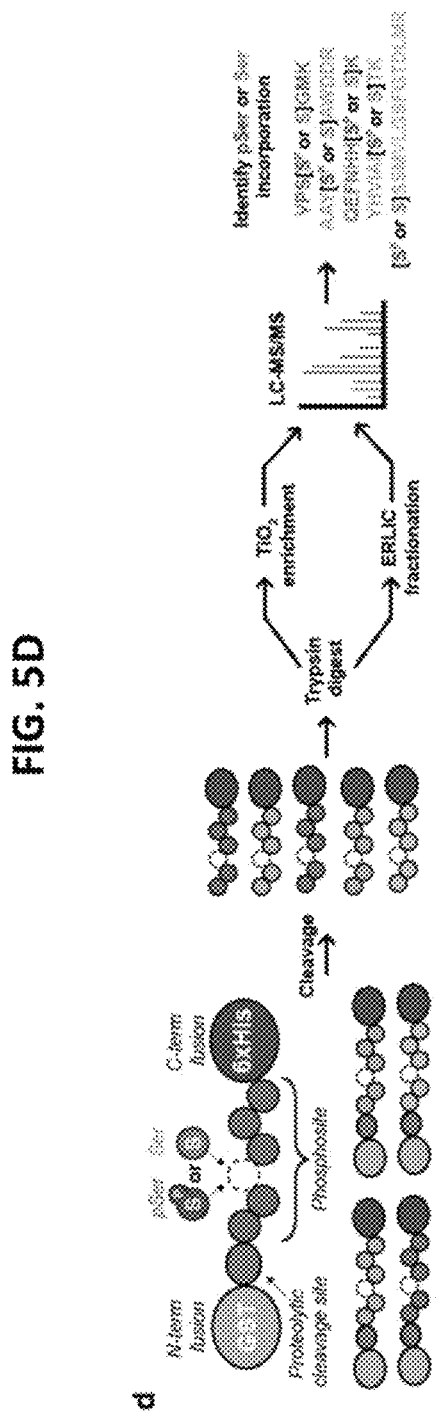

This PCR product was introduced into the modified pCRT7 vector via NdeI/SacI sites, and recombinant phosmachinery. Incorporation of pSer or Ser into recombinant phosphoproteins was specified by a central TAG codon. ≤15 amino acids were encoded on either side corresponding to the observed sequence within a human protein as listed in the PhosphoSitePlus database. In the case where pSer was observed close to a protein terminus, fewer than 15 amino acids were encoded. FIG. 5B shows the peptide lengths of synthetic phosphoproteins corresponding to the purple protein region in FIG. 5A. The majority of phosphoproteins were 31 amino acids in length. FIG. 5C illustrates a mass spectrometry workflow for the enrichment or fractionation and detection of phosphoproteins from a complex mixture. Mass spectrometry-based proteomics was used to confirm phosphosite expression and site-specific incorporation of pSer across different mode #1 library preparations (FIG. 5D).

Figure 5F:
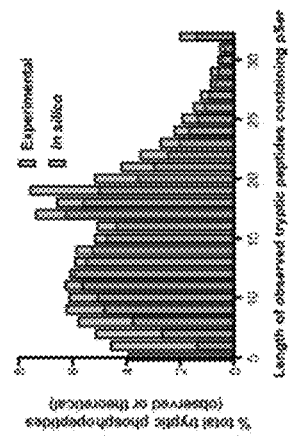
Figure 5E:
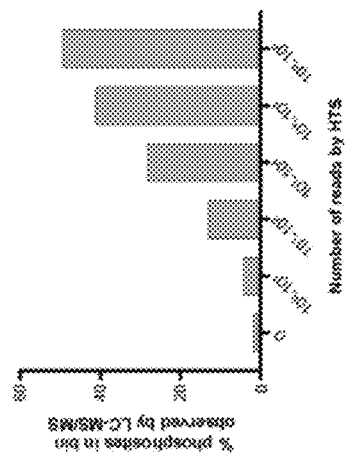

FIG. 5E demonstrates that increased DNA abundance in the expression plasmid library as shown by next-generation sequencing (NGS) (as described in Example 3) increases likelihood of phosphoprotein detection by LC-MS/MS.

Figure 5G:
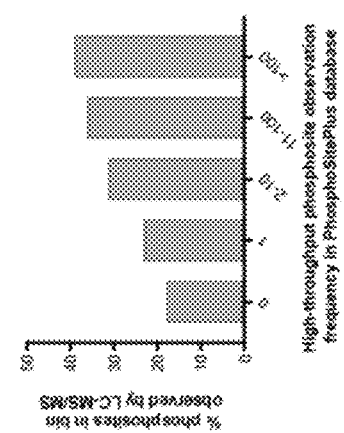
Figure 5H:
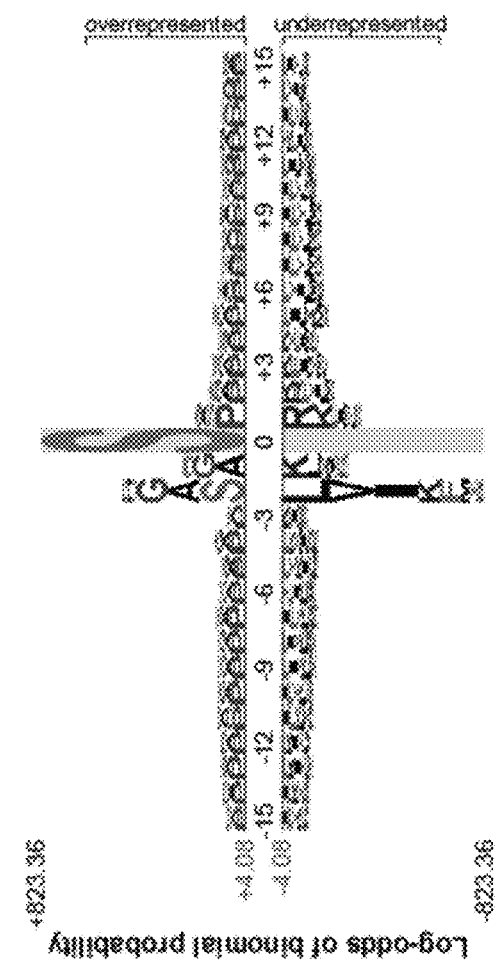

FIG. 5F provides a length distribution of theoretical and experimentally detected phosphoproteins. This distribution shows decreased likelihood of observing small (≤10 amino acids) recombinant phosphoproteins. FIG. 5G demonstrates there is a positive correlation between frequency of previous observation in high-throughput LC-MS/MS experiments as listed by PhosphoSitePlus and experimental recombinant phosphoprotein observation. FIG. 5H shows that sequence features at the −1 and −2 positions correlate with ability to synthesize, purify and/or detect recombinant phosphoproteins. The Fixed central pSer residue highlighted is in gray. See O'Shea, et al. (2013).

Example 2

In this example, a library of phosphopeptide-encoding oligonucleotides was expressed, and the phosophopeptides were purified. Plasmid libraries were electroporated into modified C321.ΔA cells containing either the SepOTSλ or tRNA$^{supD}$-encoding plasmids. Electroporated cells were directly inoculated into 100 mL LB supplemented with 100 ng/μL ampicillin and 25 ng/μL kanamycin and grown overnight at 30° C., 230 rpm. 4×500 mL of LB with 100 ng/μL ampicillin, 25 ng/μL kanamycin, and 2 mM O-phospho-L-serine was inoculated with overnight culture to an $OD_{600}$ of 0.15 and grown at 30° C., 230 rpm until $OD_{600}$—0.6-0.8. Phosphoprotein library and SepOTSλ expression was then induced with 0.2% arabinose and 1 mM isopropyl β-D-1-thiogalactopyranoside, respectively. Cells were grown for an additional 4 h at 30° C., 230 rpm. Cells were harvested by centrifugation and frozen at −80° C.

500 mL cell pellets were resuspended in 6 mL lysis buffer (50 mM Tris pH 7.4, 500 mM NaCl, 500 μM EDTA, 500 μM EGTA, 10% glycerol, 1 mM DTT, 50 mM NaF, 1 mM $NaVO_4$, 1 mg/mL lysozyme, 1 Roche cOmplete protease inhibitor tablet per 50 mL) and sonicated on ice using a QSonica Q500 with ⅛" microtip probe (10 s on, 40 s off, 40% amplitude, on for 3 min total). Combined lysates were then passed over 1 mL equilibrated Ni-NTA resin (Qiagen) in a purification column by gravity. Resin was then washed with 10 mL wash buffer (50 mM Tris pH 7.4, 500 mM NaCl, 500 μM EDTA, 500 μM EGTA, 10% glycerol, 1 mM DTT, 50 mM NaF, 1 mM $NaVO_4$, 20 mM imidazole) and eluted with 5 mL elution buffer (50 mM Tris pH 7.4, 500 mM NaCl, 500 μM EDTA, 500 μM EGTA, 10% glycerol, 1 mM DTT, 50 mM NaF, 1 mM $NaVO_4$, 250 mM imidazole). The eluate was then incubated with 1 mL equilibrated glutathione HiCap resin (Qiagen) mixing end-over-end for 30 min at RT and washed with 10 mL wash buffer by gravity. 4 mL elution buffer (50 mM Tris pH 7.4, 500 mM NaCl, 500 μM EDTA, 500 μM EGTA, 10% glycerol, 1 mM DTT, 50 mM NaF, 1 mM $NaVO_4$, 50 mM reduced L-glutathione) was then passed over the resin. Eluate was buffer exchanged (50 mM Tris pH 7, 150 mM NaCl, 1 mM EDTA, 1 mM DTT) and concentrated to ~500 μL using an Amicon Ultra-4 10 kDa molecular weight cutoff spin column (Millipore) and incubated with 20 μL (40 units) PreScission protease (GE Healthcare Life Sciences) end-over-end overnight at 4° C. Peptide was then passed through an Amicon Ultra-0.5 30 kDa molecular weight cutoff to remove the cleaved GST and uncleaved library. The peptide library was then concentrated using Amicon Ultra-0.5 3 kDa molecular weight cutoff and buffer exchanged with 10 mM Tris, pH 8. Concentrated peptide was quantified by bicinchoninic acid assay and dried by centrifugal vacuum concentration.

Figure 6:
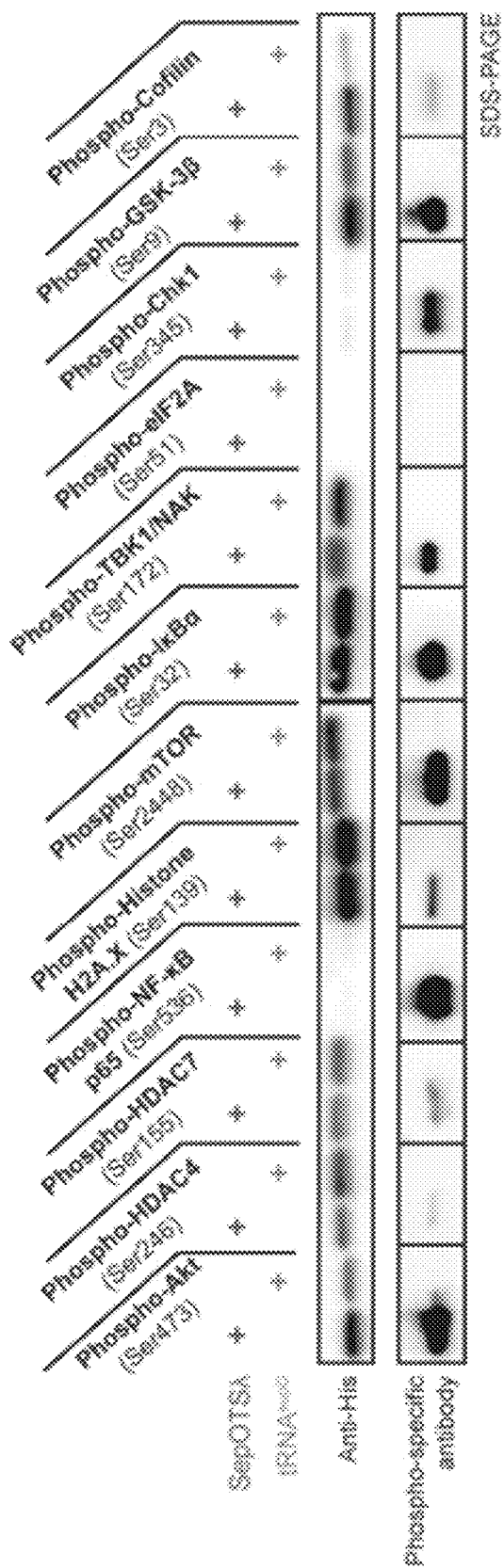
FIG. 6 shows recombinant phosphoproteins produced by cells expressing phosphopeptide-encoding oligonucleotides described herein are recognized by phospho-specific antibodies.

Clonal phosphoprotein expression and evaluation as in FIG. 6 was performed by co-transformation of the SepOTSλ or tRNA$^{supD}$-encoding plasmids with the phosphoprotein gene on the modified pCRT7 plasmid in chemically competent (standard RbCl method) modified C321.ΔA cells. Cells were plated on LB agar with 100 ng/μL ampicillin and 25 ng/μL kanamycin and grown for 18 h at 30° C. Up to 5 colonies were picked and grown in 5 mL 100 ng/μL ampicillin and 25 ng/μL kanamycin and grown overnight at 30° C., 230 rpm. A 25% glycerol stock was made of each strain, and each stock was restreaked on a selective agar plate and incubated for 18 h at 30° C. 5 colonies were picked in 5 mL LB 100 ng/μL ampicillin and 25 ng/μL kanamycin and grown in 5 mL LB containing 100 ng/μL ampicillin and 25 ng/μL kanamycin at 30° C., 230 rpm overnight. Cells were then diluted to $OD_{600}$=0.15 in 20 mL LB with 100 ng/μL ampicillin, 25 ng/μL kanamycin and 2 mM O-phospho-L-serine, grown to mid-log ($OD_{600}$=0.6-0.8), and protein expression was induced with 0.2% arabinose and 1 mM IPTG. Cells were grown for an additional 4 h at 30° C., 230 rpm. An equivalent number of cells as 1 mL $OD_{600}$=2.5 was spun down for 5 minutes at 4,000×g, supernatant was aspirated, and cell pellets were frozen at −80° C. overnight, and then lysed for 10 minutes in 40 μL lysis buffer (50 mM Tris pH 7.4, 150 mM NaCl, 1 mM DTT, 50 mM NaF, 1 mM $NaVO_4$, 5% glycerol, Roche cOmplete protease inhibitors, 1x Novagen BugBuster). Lysates were then spun down at 21,000×g for 7 minutes to remove cell debris. 1 μL lysate was run per lane on acrylamide gels.

Example 2A

100 μM Phos-tag acrylamide (Wako) within handmade 12% acrylamide gels was used for visualization of phosphoproteins by western blot. SDS-PAGE gels (4-15% acrylamide, Bio-Rad) and Phos-tag gels were transferred onto PVDF membranes. Anti-His westerns were performed using 1:2,500 diluted rabbit Anti-6xHis antibody (PA1-983B, Thermo Fisher Scientific) in 5% w/v milk in TEST for 1 h and 1:10,000 diluted donkey anti-rabbit HRP (711-035-152, Jackson ImmunoResearch) in 5% w/v milk in TBST for 1 h.

Figure 4B:
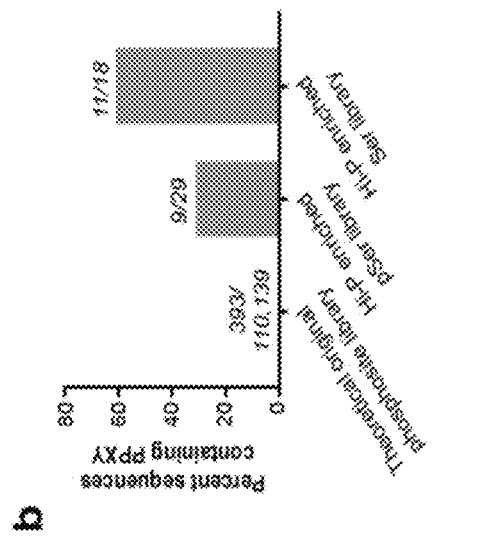
FIGS. 4A to 4D illustrate methods of detecting phosphorylation-dependent protein-proteins interactions with NEDD4 WW2 domains using a library of phosphopeptide-encoding oligonucleotides.

Phos-tag gel analysis demonstrated robust pSer incorporation within the phosphoprotein library (FIG. 1C). Mass spectrometry-based proteomics was used to confirm site-specific incorporation of pSer vs. Ser across the different library preparations (FIG. 5C). Evidence for the presence of at least 56,401 phosphosites was obtained across all samples, and pSer was directly observed in more than 36,2060 unique proteins synthesized using the SepOTSλ. A relatively low number of library members (<1,200) containing pSer was detected in the Ser library, likely due to false discovery by mass spectrometry, column carryover during preparative steps or low levels of endogenous phosphorylation by *E. coli* kinases. Comprehensive library validation by proteomics was limited by incomplete DNA representation in the plasmid library, small tryptic peptide fragment length and inclusion of phosphoproteins not well suited for mass spectrometry (FIGS. 4D to 4E).

The recombinant human serine phosphoproteome disclosed herein enables the detection of important pSer-dependent protein-protein interactions and enables screening candidates for such interactions. To test that the synthetic phosphoproteins retain known phosphorylation-dependent binding characteristics, 12 separate mode #1 phosphosites were synthesized from the library containing the epitopes of pSer-specific rabbit monoclonal antibodies (Table D). 11 of 12 pSer-encoding mode #1 phosphosites were recognized by their corresponding antibodies, while epitope-matched Ser-encoding proteins were not (FIG. 6). Protein phosphorylation generally occurs in intrinsically disordered regions lacking well-defined secondary and tertiary structure (Iakoucheva, L. M. et al. The importance of intrinsic disorder for protein phosphorylation. Nucleic acids research 32, 1037-1049 (2004)) and, similar to previous results from combinatorial arrays of short synthetic phosphopeptides (Yaffe, M. B. et al., (1997); Zhou, S. et al. SH2 domains recognize specific phosphopeptide sequences. *Cell* 72, 767-778, doi: 10.1016/0092-8674(93)90404-E (1993)), the present phosphoprotein display contains the minimal information required to mediate known phosphorylation-dependent interactions.

FIG. 6 demonstrates that the pSer-containing recombinant phosphoproteins produced by cells expressing phosphopeptide-encoding oligonucleotides as described herein are recognized by phospho-specific antibodies. GST-fusion phosphoproteins predicted to be recognized by common pSer-specific antibodies offered by Cell Signaling Technologies were expressed clonally in C321.ΔA with either pSer or Ser. $OD_{600}$-normalized lysates were analyzed by SDS-PAGE and either anti-His or anti-phosphoprotein western, as indicated. 11/12 recombinant phosphoproteins were successfully expressed. Proteins produced using the SepOTSλ and not tRNA$^{supD}$ were recognized by the phospho-specific antibodies, indicating anticipated pSer incorporation and phospho-specific antibody epitope recognition. Phospho-specific primary antibodies used in FIG. 6 are listed in Table D below and were used in 1:1,000 dilutions in 5% w/v milk in TBST for 1 h. Protein bands were then visualized using Clarity ECL substrate (Bio-Rad) and an Amersham Imager 600 (GE Healthcare Life Sciences).

TABLE D

| Product Name | Protein | Phosphosite amino acid seq (s = pSer) | DNA sequence |
| --- | --- | --- | --- |
| Phospho-Akt (Ser473) (D9E) XP ® Rabbit mAb | AKT1 | MECVDSERRPHFPQFsYSASGTA (SEQ. ID NO: 63) | ATGGAATGCGTTGACTCTGAACGTCGTCC GCACTTCCCGCAGTTCtagTACTCTGCGT CTGGCACCGCG (SEQ ID NO: 45) |
| Phospho-HDAC4 (Ser246)/HDAC5 (Ser259)/HDAC7 (Ser155) (D27B5) Rabbit mAb | HDAC4 | GMYDAKDDFPLRKTAsEPNLKLR SRLKQKVA (SEQ. ID NO: 64) | GGTATGTACGACGCGAAAGACGACTTCCC GCTGCGTAAAACCGCGtagGAACCGAACC TGAAACTGCGTTCTCGTCTGAAACAGAAA GTTGCG (SEQ ID NO: 46) |
| Phospho-HDAC4 (Ser246)/HDAC5 (Ser259)/HDAC7 (Ser155) (D27B5) Rabbit mAb | HDAC7 | LPSDPPEHFPLRKTVsEPNLKLR YKPKKSLE (SEQ. ID NO: 65) | CTGCCGTCTGACCCGCCGGAACACTTCCC GCTGCGTAAAACCGTTtagGAACCGAACC TGAAACTGCGTTACAAACCGAAAAAATCT CTGGAA (SEQ ID NO: 47) |
| Phospho-NF-κB p65 (Ser536) (93H1) Rabbit mAb | NFkB-p65 | PGLPNGLLSGDEDSFsIADMDFS ALLSQISS (SEQ. ID NO: 66) | CCGGGTCTGCCGAACGGTCTGCTGTCTGG TGACGAAGACTTCTCTtagATCGCGGACA TGGACTTCTCTGCGCTGCTGTCTCAGATC TCTTCT (SEQ ID NO: 48) |
| Phospho-Histone H2A.X (Ser139) (20E3) Rabbit mAb | H2AX | VGPKAPSGGKKATQAsQEY (SEQ. ID NO: 67) | GTTGGTCCGAAAGCGCCGTCTGGTGGTAA AAAAGCGACCCAGGCGtagCAGGAATAC (SEQ ID NO: 49) |
| Phospho-m TOR (Ser2448) (D9C2) XP ® Rabbit mAb | mTOR | DTNTKGNKRSRTRTDsYSAGQSV EILDGVEL (SEQ. ID NO: 68) | GACACCAACACCAAAGGTAACAAACGTTC TCGTACCCGTACCGACtagTACTCTGCGG GTCAGTCTGTTGAAATCCTGGACGGTGTT GAACTG (SEQ ID NO: 50) |
| Phospho-IκBa (Ser32) (14D4) Rabbit mAb | IkB-alpha | RDGLKKERLLDDRDHsGLDSMKD EEYEQMVK (SEQ. ID NO: 69) | CGTGACGGTCTGAAAAAAGAACGTCTGCT GGACGACCGTACGACtagGGTCTGGACTC TATGAAAGACGAAGAATACGAACAGATGG TTAAA (SEQ ID NO: 51) |
| Phospho-TBK1/NAK (Ser172) (D52C2) XP ® Rabbit mAb | TBK1 | DFGAARELEDDEQFVsLYGTEEY LHPDMYER (SEQ. ID NO: 70) | GACTTCGGTGCGGCGCGTGAACTGGAAGA CGACGAACAGTTCGTTtagCTGTACGGCA CCGAAGAATACCTGCACCCGGACATGTAC GAACGT (SEQ ID NO: 52) |
| Phospho-eIF2a (Ser51) (D9G8) XP ® Rabbit mAb | eIF2-alpha | LEYNNIEGMILLSELsRRRIRSI NKLIRIGR (SEQ. ID NO: 71) | CTGGAATACAACAACATCGAAGGTATGAT CCTGCTGTCTGAACTGtagCGTCGTCGTA TCCGTTCTATCAACAAACTGATCCGTATC GGTCGT (SEQ ID NO: 53) |

TABLE D-continued

| Product Name | Protein | Phosphosite amino acid seq (s = pSer) | DNA sequence |
|---|---|---|---|
| Phospho-Chk1 (Ser345) (133D3) Rabbit mAb | Chk1 | TSPSYIDKLVQGSIFsQPTCPDH MLLNSQLL (SEQ. ID NO: 72) | ACCTCTCCGTCTTACATCGACAAACTGGT TCAGGGTATCTCTTTCtagCAGCCGACCT GCCCGGACCACATGCTGCTGAACTCTCAG CTGCTG (SEQ ID NO: 54) |
| Phospho-GSK-3β (Ser9) (D85E12) XP® Rabbit mAb | GSK3B | MSGRPRTTsFESCKPVQQPSAFG (SEQ. ID NO: 73) | ATGTCTGGTCGTCCGCGTACCACCtagTT CGCGGAATCTTGCAAACCGGTTCAGCAGC CGTCTGCGTTCGGT (SEQ ID NO: 55) |
| Phospho-Cofilin (Ser3) (77G2) Rabbit mAb | Cofilin-1 | MAsGVAVSDGVIKVFNDM (SEQ. ID NO: 74) | ATGGCGtagGGTGTTGCGGTTTCTGACGGT GTTATCAAAGTTTTCAACGACATG (SEQ ID NO: 56) |

Example 3

In this example, high-throughput sequencing information was generated for the library of phosphopeptide-encoding oligonucleotides produced in Example 1.

For this example, and for other experiments using high-throughput sequencing, DNA libraries encoding phosphoproteins prepared as GST-fusion constructs as in FIG. 1C were grown from ElectroMAX DH10B glycerol stocks containing the phosphoprotein gene library on the modified pCRT7 vector by direct inoculation of the glycerol stock in 100 mL LB with 100 ng/μL ampicillin and grown overnight at 37° C., 230 rpm. Plasmid library was harvested by maxiprep (Perfectprep, Eppendorf). A KpnI/HindIII digest of approximately 500 μg plasmids was performed and the phosphoprotein gene library insert was extracted on a 2% agarose gel. DNA was used for 75 bp paired-end sequencing.

PCR amplicons of phosphoprotein gene libraries in the modified pNAS1B vector for Hi-P experiments were generated using various combinations of primers P9-P16 (See Table C above), allowing for sample multiplexing and determination of sample of origin from degenerate base ends followed by 2 bp barcodes. DNA was used for 100 bp paired-end sequencing.

DNA samples were end-repaired, A-tailed and adapters were ligated. Indexed libraries that met appropriate cut-offs were quantified by both qRT-PCR (KAPA Biosystems) and insert size distribution was determined with the LabChip GX. Samples with a yield of ≥0.5 ng/μl were used for sequencing.

Sample concentrations were normalized to 350 pM and loaded onto Illumina HiSeq 4000 flow cells at a concentration that yielded 300-350 million passing filter clusters per lane. Each amplicon library was run over 50% of two lanes (multiplexed with 50% exome libraries). The samples were then sequenced using 75 or 100 bp paired-end reads on an Illumina HiSeq 4000 according to Illumina protocols. The 6 bp index was read during an additional sequencing read that automatically followed the completion of read 1. Data generated during sequencing runs was simultaneously transferred to the high-performance computing cluster. A positive control (prepared bacteriophage Phi X library) provided by Illumina was spiked into every lane at a concentration of 0.3% to monitor sequencing quality in real time.

Sequencing reads were first filtered for quality using Trimmomatic (see Bolger, A. et al., Trimmomatic: a flexible trimmer for Illumina sequence data. *Bioinformatics* 30, 2114-2120, doi:10.1093/bioinformatics/btu170 (2014)), which applied a sliding window filter of width 2 bp and a Phred score cutoff of 30. If the average quality score over two consecutive bases fell below 30, the read was trimmed to remove the remaining bases. Quality trimmed read pairs were then merged using BBMerge with the stringency set to "strict" (sourceforge.net/projects/bbmap). Using custom scripts, the merged reads were then sorted and assigned to the various input libraries based on barcodes added during the PCR amplification step. The variable sequence region for each amplicon was then extracted and for each input library the abundance of every unique sequence was calculated.

In order to determine library coverage, sequencing reads were filtered for quality using Trimmomatic with a sliding window filter of 2 bp and Phred score cutoff of 30. Additionally, the first 5 bp were trimmed from the start of the reads. Subsequently, the trimmed read pairs were merged using BBMerge with the stringency set to "strict". The FASTQ file of merged read pairs was then aligned to a FASTA file containing each of the library member sequences using the BWA-mem algorithm with the -M option. The resultant alignment files were then sorted and indexed using samtools and the mappings to each library member were evaluated using BBMap's pileup.sh with "secondary=false".

This sequencing analysis confirmed the presence of 94% of these oligonucleotides in the plasmid library, with 70% of sequences falling within a 100-fold range of abundance (See FIG. 1B).

Example 4A

In this example, the present method of detecting interactions was used to investigate 14-3-3 isoforms β and σ, which are both known to bind phosphoproteins containing pSer/pThr via well-defined interaction motif RSX[SP/TP]XP (SEQ ID NO:61).

The 14-3-3 sequences were fused to C-terminal split mCherry (C-mCh). The protein library, separately encoding either pSer or Ser, fused to N-terminal split mCherry (N-mCh) and isolated cells exhibiting reconstituted mCherry fluorescence by FACS. fluorescence-activated cell sorting was used to identify and select a cell based on a fluorescent signal from interaction of (1) a first fusion protein comprising a phosphopeptide (from the library of phosphopeptide-coding oligonucleotides of Example 1) and a first portion of a reporter (mCherry), and (2) a second fusion protein comprising a phosphoprotein-binding region (14-3-3) and a second portion of the reporter.

A polynucleotide encoding the phosphopeptide-encoding region of the first fusion protein is then sequenced using high-throughput sequencing. 20 mL of modified C321.ΔA cells containing either the SepOTSλ or tRNA$^{sup\ D}$(plasmid modified to include SepRS9-EFSep21, see Example 1) plasmid were grown to $OD_{600}$ of 0.4. Cells were then spun down at 4,000×g for 1 minute, supernatant was decanted, and cells were washed with 20 mL ice cold, deionized water. This was repeated once. Cells were resuspended in 50 mL water, mixed with 1 µL library plasmid (approximately 100 ng/µL), and then the plasmid library for Hi-P experiments (in pNAS1B vector, see below) was transformed using electroporation parameters stated above. The cells were then resuspended in 1 mL of S.O.C. medium (Thermo) and incubated for 1 h at 30° C. and 230 rpm in a 15 mL culture tube. These cells were then directly inoculated in 50 mL of LB with 100 ng/µL ampicillin and 25 ng/µL kanamycin and grown overnight at 30° C. and 230 rpm.

The experiments were performed in the pNAS1B vector with the following modifications: The existing KpnI site was removed by A to T substitution. A multiple cloning site containing pBAD and NdeI and PsiI sites (G1, see Table B above) was introduced between BamHI and SacI sites. The human NEDD4 WW2 domain (see Example 4B below) and the C-terminal split mCherry protein (Sawyer, N. et al. (2014)) with an added 6xHis fusion tag (G2, see Table B above) were introduced between NdeI and PsiI sites. Primers P5 and P6 (see Table C above) were used to PCR amplify the region between PsiI and XhoI sites in this vector but with the PsiI-adjacent SacI site removed. This PCR product was then reintroduced into the vector between PsiI and XhoI sites. NdeI and SacI sites 5' to the C-terminal mCherry cassette allowed the insertion of phosphobinding protein domains of interest (NEDD4-2 WW2, human 14-3-3β and 14-3-3σ from G3, G4 and G5, respectively, Table B). The N-terminal split mCherry cassette (G6, Table B) was introduced between EcoRI and PvuII sites, with internal KpnI/HindIII sites allowing for insertion of a phosphoprotein cassette. Another HindIII site in the vector had been removed by site-directed mutagenesis using P7 and P8 (Table C∂). Phosphoprotein genes and control proteins for targeted clonal validation experiments (FIGS. 2A to 3G) were synthesized by IDT in concatenated <1,000 bp DNA sequences and ligated into either the modified pNAS or pCRT7 vector between KpnI and HindIII sites. All restriction enzymes and T4 DNA ligase were from NEB, all double-stranded *Escherichia coli* K12 codon-optimized gene inserts in Table B were synthesized by IDT, and all oligonucleotides in Table C were synthesized by the Keck Biotechnology Resource Laboratory at the Yale School of Medicine. New plasmids that were used in this work will be made available through Addgene.

The next morning, cultures were diluted to an $OD_{600}$ of 0.15 in 5 mL of LB containing 100 ng/µL ampicillin, 25 ng/µL kanamycin, and 2 mM O-phospho-L-serine and grown at 30° C. and 230 rpm. The cells were grown until $OD_{600}$ reached mid-log (0.6-0.8), then protein expression was induced using 1 mM IPTG, 0.2% arabinose, and 100 ng/µL anhydrotetracycline, and grown at 20° C. and 230 rpm for 20-24 h. 100 µL of cells were spun down at 4,000×g and supernatant was removed. Cells were then resuspended in 3 mL ice cold M9 minimal media in a 5 mL polystyrene tube (Falcon).

Using a BD FACSAria III, cells were interrogated for mCherry-based fluorescence using a 561-nm laser. Cells were sorted using a gate empirically determined to yield substantially enriched fluorescent signal in regrown cell populations, which differed for each phospho-binding domain. Cells were sorted directly into 1 mL LB without antibiotic, recovered at 30° C. and 230 rpm for 3 h, and then supplemented with 2 mL LB with a final concentration of 100 ng/µL ampicillin and 25 ng/µL kanamycin. After 24 h, sorted cell populations were then further supplemented with 2 mL LB with 100 ng/µL ampicillin and 25 ng/µL kanamycin and grown at 30° C. and 230 rpm for an additional 16 h. The procedure for protein expression, preparation for FACS, and cell sorting was repeated, using the same sorting and gating parameters as the first round of sorting. Cells were then recovered, regrown, induced and prepared for FACS as above. Cellular mCherry fluorescence was then observed using the FACSAria III. Plasmid libraries isolated by miniprep of twice-sorted cell populations were prepared for next-generation sequencing as described above. An example control experiment was performed, where cells harboring a known protein interaction pair (NEDD4 WW2-C-mCh and N-mCh-IPGTPPPNYD) (SEQ ID NO:58) (Lu et al., 1999) were mixed at known ratios with cells encoding the NEDD4 WW2-mCh and N-mCh with no fusion peptide; iterative sorting rounds enabled enrichment cells encoding the known interacting proteins at every tested dilution.

Figure 3B:
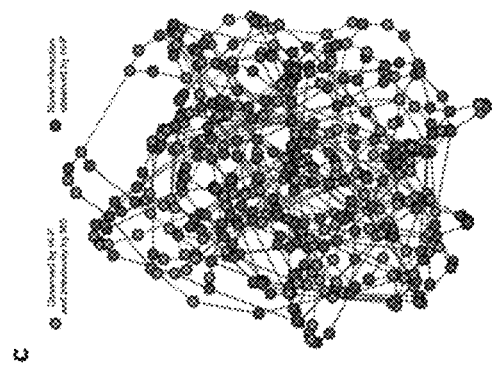
Figure 3C:
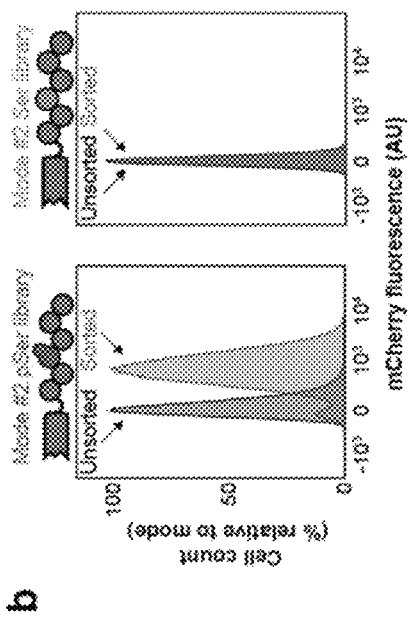
Figure 7:
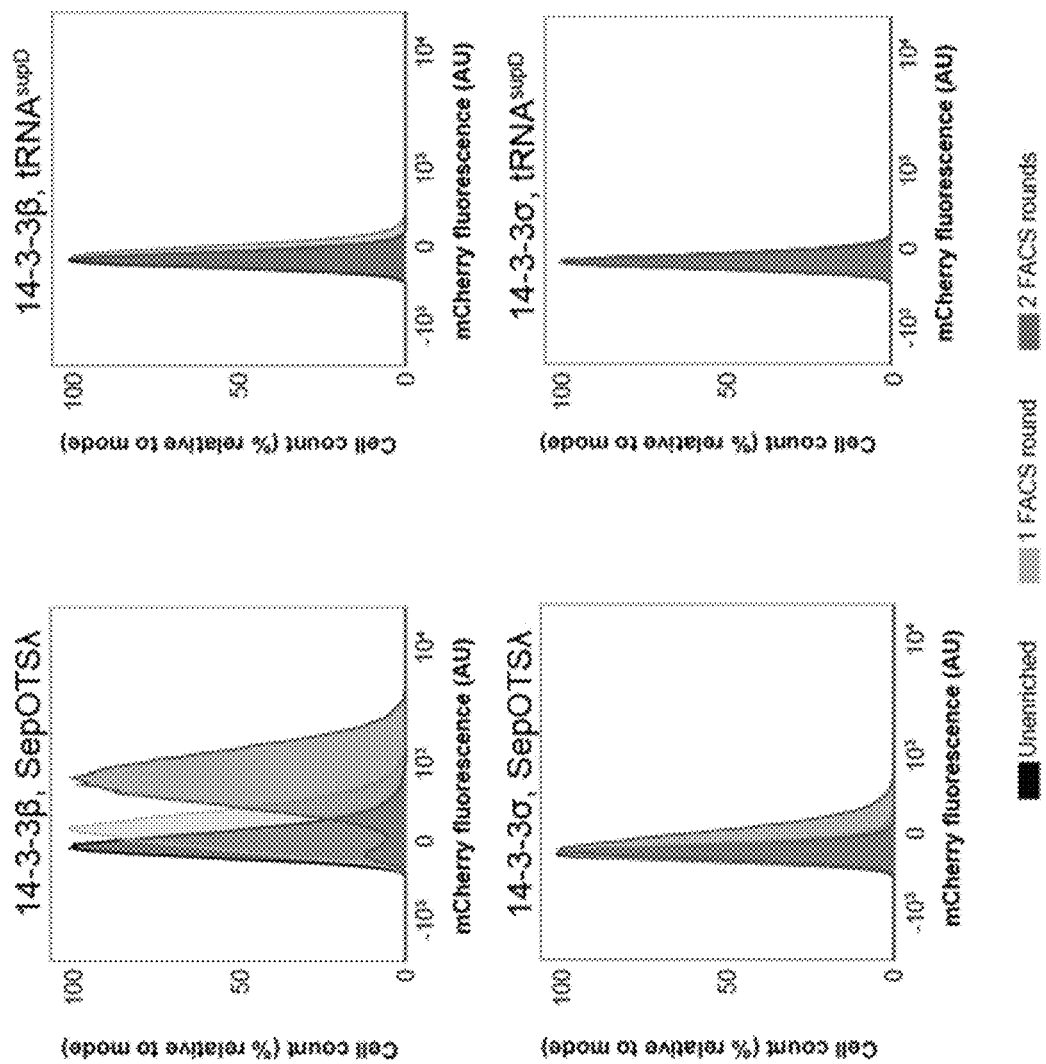
FIG. 7 shows results of screening for phosphoprotein interactions with 14-3-3 isoforms using the present library of phosphopeptide-encoding oligonucleotides.

FIG. 3B shows results of screening for pSer-encoding phosphoprotein interactions with 14-3-3β, while FIG. 7 shows results of screening for such interactions with both 14-3-3 isoforms using the present library of phosphopeptide-encoding oligonucleotides. Mean population fluorescence after FACS increased with SepOTSλ (encoding pSer) but not with tRNA$^{supD}$ (encoding Ser). n=$10^5$ cells for flow cytometry observation. AU means arbitrary units. Sequential FACS experiments yielded cell populations with increased mCherry fluorescence only when using the mode #2 phosphosite library containing pSer (FIG. 3B, FIG. 7). These results indicate that Hi-P recapitulates the known phosphorylation binding preference of 14-3. HTS experiments with both 14-3-3 isoforms identified hundreds of interactions previously observed in other experiments (FIGS. 8A & 8B; see also Tinti, M. et al. (2014)) including TAZ, the top-sequenced candidate phosphosite interactor, which participates in an important phosphorylation-dependent 14-3-3 interaction previously identified in vivo. Kanai, F. et al. TAZ: a novel transcriptional co-activator regulated by interactions with 14-3-3 and PDZ domain proteins. The EMBO Journal 19, 6778-6791, doi:10.1093/emboj/19.24.6778 (2000). Given that approximately 60% of Hi-P-identified phosphosite interactors were derived from human proteins never shown to interact with 14-3-3 isoforms, Hi-P can be useful in the identification of both known and candidate novel interactions. Network analysis using Levenshtein distances to examine similarity between phosphosite sequences showed that novel interactions are dispersed amongst known interactors, indicating a lack of systematic bias in 14-3-3 interactions identified by Hi-P (FIG. 3C).

Figure 8B:
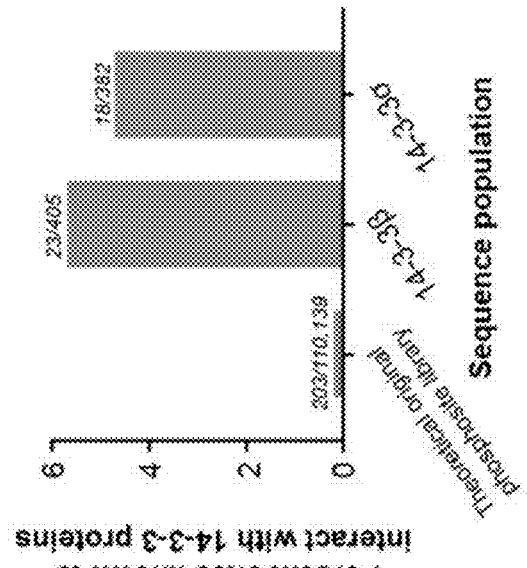
FIGS. 8A and 8B show that the present methods can yield enrichment of previously-known 14-3-3 interacting proteins.
Figure 8A:
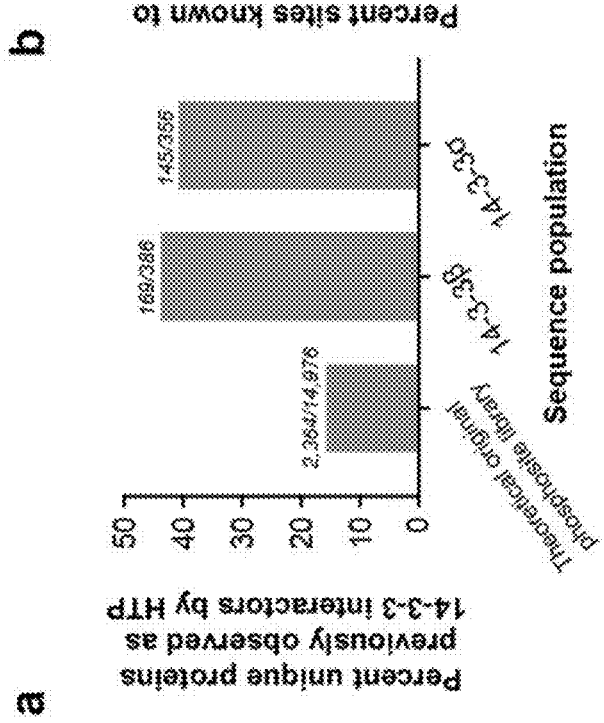

FIG. 8A shows the numbers of unique phosphoproteins previously observed in high-throughput studies occurring in the total unsorted library (precursor) or in FACS-sorted populations according to the present detection methods. FIG. 8B shows direct 14-3-3 interaction sites as determined by previous biochemical studies occurring in the unsorted library (precursor) or in Hi-P FACS-sorted populations. See Tinti, M. et al. ANIA: ANnotation and Integrated Analysis of the 14-3-3 interactome. *Database* 2014, doi:10.1093/database/bat085 (2014).

Global motif analysis from high-throughput sequencing of the library members interacting with 14-3-3 revealed a marked RSXSPXP (SEQ ID NO:57) motif, perfectly matching the canonical 14-3-3 interaction motif (FIG. 3D, FIG. 9A to 9C). Together, these data showed that the human phosphoproteome library disclosed here was able to recapitulate physiologically relevant protein-protein interactions that were effectively identified by the present methods using FACS and sequencing.

It was hypothesized that encoding native human phosphoprotein sequences rather than randomized pools of peptides would enable discovery of interactions that deviate from simple motif analysis. Notably, only about half of the identified sequences contained the −2 S or +2 P 14-3-3 motif elements, consistent with previous work and demonstrating the ability to identify candidate interactors that do not rigorously conform to known motifs (Tables E and F). Johnson, C. et al. Bioinformatic and experimental survey of 14-3-3-binding sites. Biochemical Journal 427, 69-78, doi:10.1042/BJ20091834 (2010).

TABLE E

| position | frequency | value |
|---|---|---|
| P at 2 | 48.76% | 89.7773 |
| S at −2 | 55.37% | 76.9384 |
| R at −3 | 40.77% | 42.9288 |
| A at 1 | 17.36% | 15.7376 |
| R at −4 | 20.11% | 13.7308 |
| L at 1 | 20.66% | 10.8046 |
| L at 4 | 18.18% | 8.50083 |
| A at −2 | 14.33% | 6.51062 |
| A at 3 | 13.77% | 6.44913 |
| A at −1 | 14.60% | 6.2586 |
| S at 0 | 100% | N/A |
| Q at −1 | 9.37% | 5.9796 |
| L at −5 | 16.80% | 5.74403 |
| P at −12 | 13.77% | 4.42936 |
| G at −6 | 12.67% | 4.33248 |
| R at −5 | 14.60% | 4.32866 |

Table E reports positional amino acid frequencies in pSer-encoding phosphoprotein populations interacting with 14-3-3β the present methods. The table shows the frequency of occurrence of significantly over- or underrepresented amino acids at the indicated positions relative to the central pSer site (position 0), and the log-odds of the bionomial probability via pLogo analysis. Background for analysis was all phosphoproteins encoded in the entire theoretical 110,139-member library.

TABLE F

| position | frequency | value |
|---|---|---|
| P at 2 | 47.65% | 80.343 |
| S at −2 | 47.06% | 48.9009 |
| R at −3 | 39.12% | 36.3951 |
| A at 1 | 18.82% | 17.789 |
| A at −2 | 17.35% | 10.4933 |
| Q at −1 | 10.59% | 7.60462 |
| R at −4 | 15.88% | 6.66726 |
| L at 1 | 17.94% | 6.60014 |
| P at −13 | 15.29% | 5.8171 |
| S at 0 | 100% | N/A |
| A at 3 | 13.53% | 5.77798 |
| L at 4 | 16.18% | 5.55519 |
| P at −12 | 14.71% | 5.19983 |

Table F reports positional amino acid frequencies in pSer-encoding phosphoprotein populations interacting with 14-3-3σ as determined by the present methods. The frequency of occurrence of significantly over- or underrepresented amino acids at the indicated positions relative to the central pSer site (position 0), and the log-odds of the bionomial probability via pLogo analysis. Background for analysis was all phosphoproteins encoded in the entire theoretical 110,139-member library.

Figure 10B:
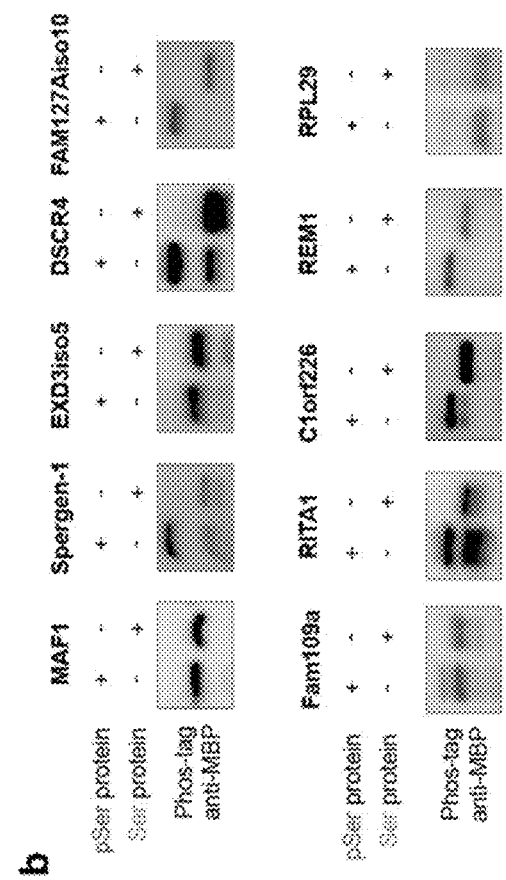
FIGS. 10A to 10C is a western blots of purified fusion proteins comprising phosphopeptides from pull-down assays.
Figure 10A:
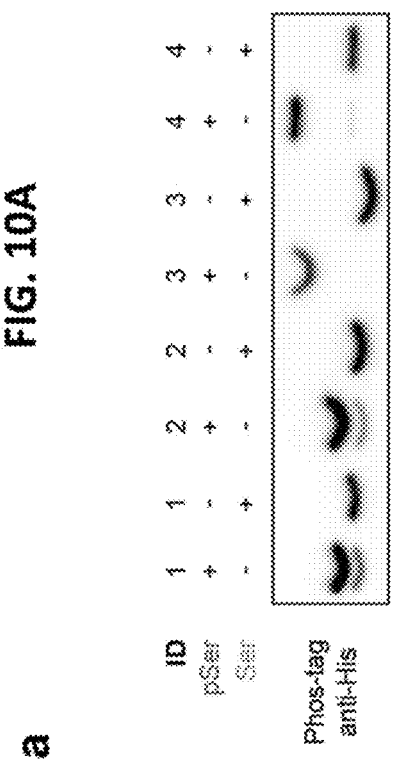
Figure 10C:
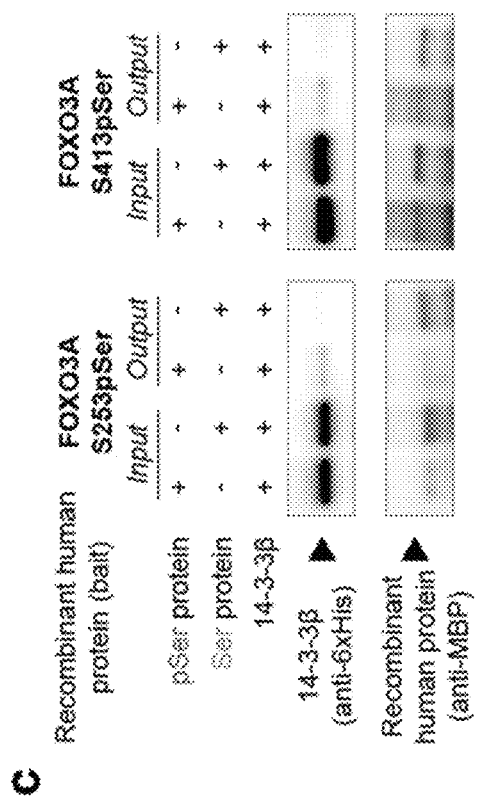

To confirm pSer-dependent interaction, two 14-3-3-interacting phosphoproteins were clonally expressed for each 14-3-3 isoform, and their fluorescence was re-examined in the present detection methods. (See Example 5 for additional detail). The selected phosphoprotein hits matched the RSXSPXP (SEQ ID NO:57) motif to varying degrees (FIG. 3E). The results confirmed the phosphorylation-dependent interactions first identified by Hi-P (FIG. 3F), and in vitro pull-down assays using immobilized GST-fusion constructs of these same protein targets (FIG. 10A) provided additional evidence that the interactions were phosphorylation dependent (FIG. 3G). In in vitro pull-down studies, 9 out of 10 of these proteins exhibited interactions with 14-3-3β that were enhanced by or dependent on pSer incorporation (FIGS. 3G & 10B). To test a known and a candidate novel interaction site from the same full-length protein, human FOXO3A containing pSer at well-defined site (pSer253) (see Tzivion, G., et al., FoxO transcription factors; Regulation by AKT and 14-3-3 proteins. *Biochimica et Biophysica Acta (BBA)-Molecular Cell Research* 1813, 1938-1945 (2011)) and a new site (pSer413) were synthesized. Both were identified by Hi-P. As with the other tested recombinant phosphoproteins, both forms of FOXO3A showed a pSer-dependent interaction with 14-3-3β, demonstrating that Hi-P can confirm known biology and predict potential new interaction sites in the context of full-length proteins (FIG. 10C).

Figure 3D:
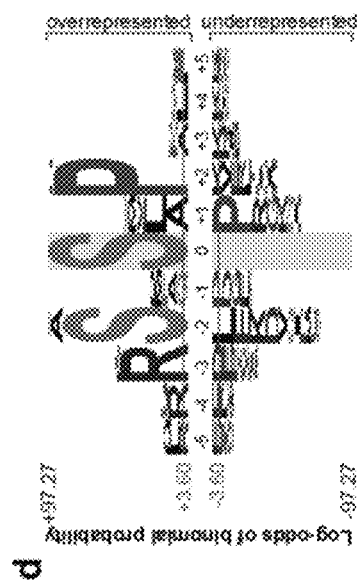
Figure 3E:
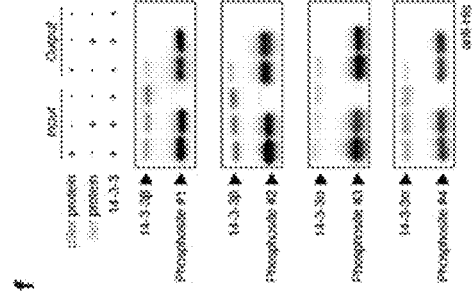
Figure 3F:
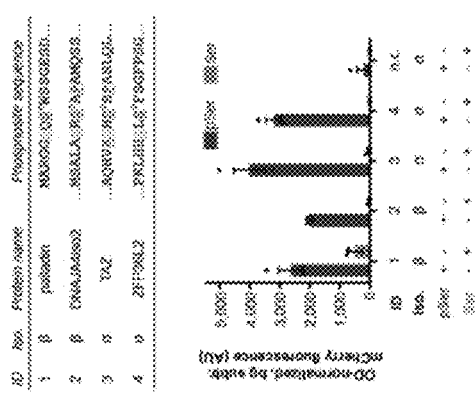
Figure 3G:
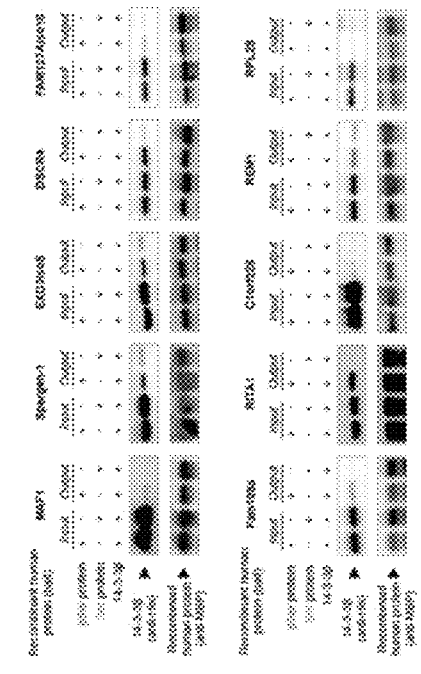

FIG. 3D shows pLogo analysis of 14-3-3 Hi-P results. The red line indicates P=0.05 significance threshold with Bonferroni correction. FIG. 3E shows top-ranking phosphoprotein sequences identified by the present methods of screening using either 14-3-3β or 14-3-3σ isoforms, as indicated. Amino acids surrounding the central pSer residue (in red) adhering to the RSXS$^P$XP (SEQ ID NO:57) motif are colored and bolded. FIG. 3E shows the validation of select 14-3-3 Hi-P hits. Error bars show s.e.m. (n=3 biological replicates); n.c.=negative control phosphoprotein not anticipated to interact with 14-3-3 proteins AGPADAPAGA-VVGGG[S$^P$/S]PRGRPGPVPAPGLLA (SEQ ID NO:59). FIG. 3F is a pull-down analysis of immobilized GST-fusion phosphoproteins. This analysis confirmed that pSer incorporation is necessary for 14-3-3 interaction.

Figure 9A:
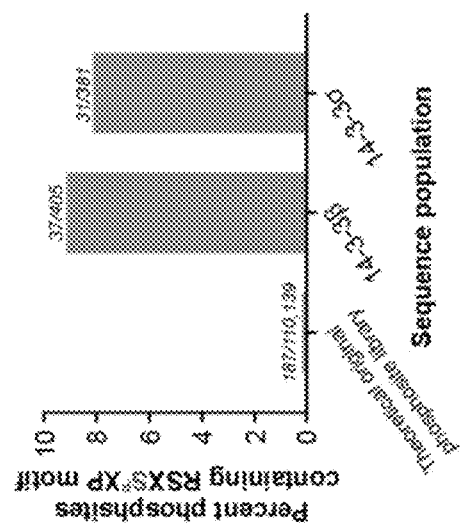
FIGS. 9A to 9C show phosphopeptide ligand sequence analysis for phosphopeptide-interacting 14-3-3 isoforms.
Figure 9B:
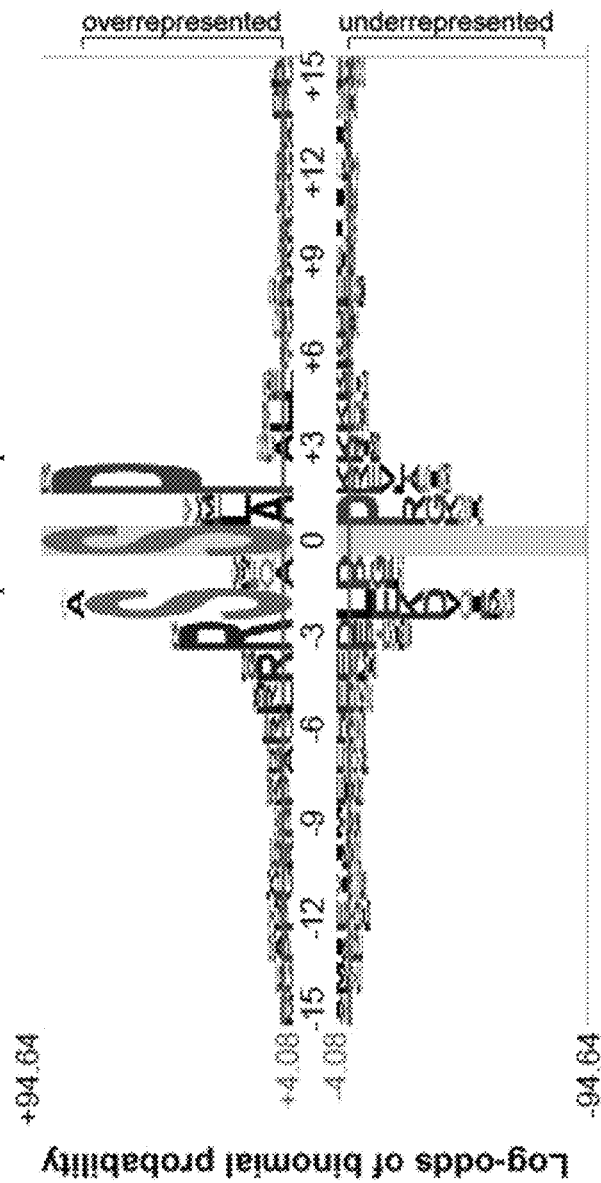
Figure 9C:
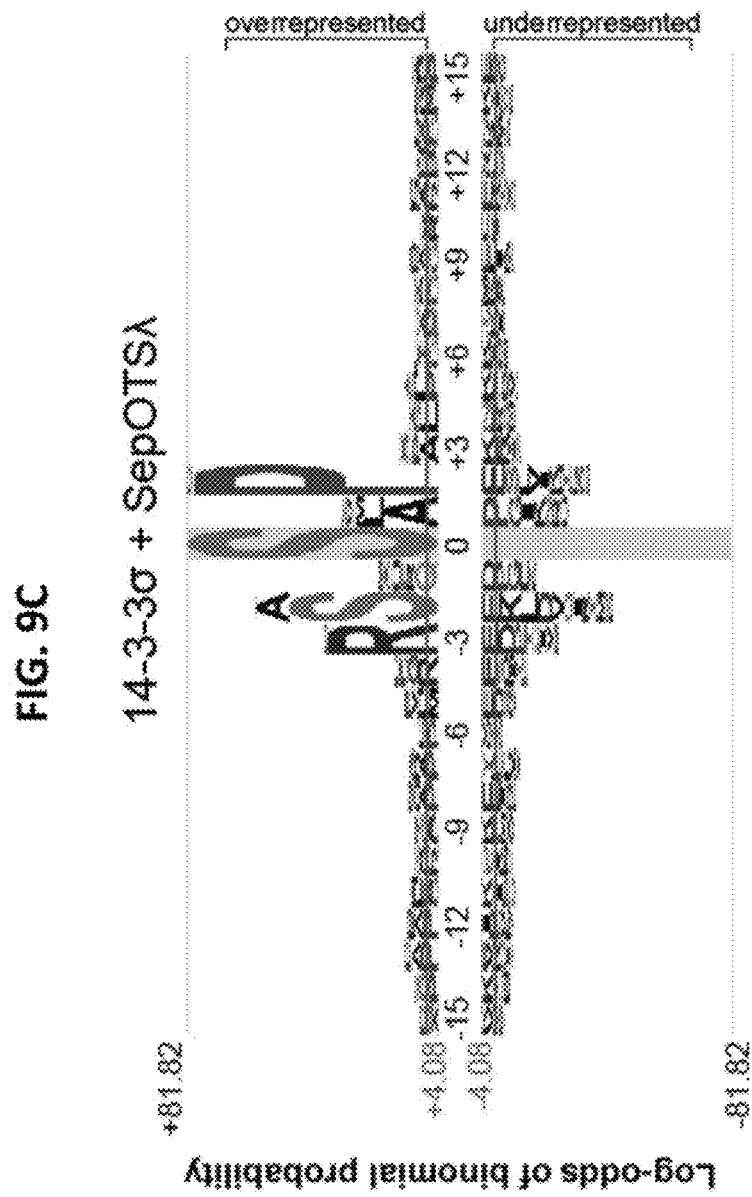

Additional analyses from these experiments are provided in FIGS. 9A to 9C. FIG. 9A indicates the number of protein sequences containing the RSXSPXP (SEQ ID NO:57) motif in the unsorted library (precursor) or in FACS-sorted Hi-P populations. FIGS. 9B and 9C provide pLogo analysis (see O'Shea, J. P. et al. (2013) of phosphoproteins identified by high-throughput sequencing (>1,000 reads) of FACS-derived populations isolated in C321.ΔA with the SepOTSλ using the BiFC split mCherry system co-expression of the phosphoprotein library and either 14-3-3β (FIG. 9B) or 14-3-3σ (FIG. 9C). Red line indicates P=0.0.5 significance threshold with Bonferroni correction.

Example 4B

In this example, the present method of detecting interactions was used to investigate the second WW domain (WW2) of human E3 ubiquitin ligase neural precursor cell-expressed developmentally downregulated 4 (NEDD4) and the WW2 domain of the closely related NEDD4-2 (also known as NEDD4L). This experiment was conducted as described in Example 4A, except that the NEDD4 WW2 domains were used as the phosphopeptide of the first fusion protein.

The NEDD4 WW2 domains are of particular interest since both are believed to exhibit mixed modalities of pSer-dependent, pSer-independent and/or pSer-enhanced ligand binding21-24. See Lu, P.-J., et al., Function of WW Domains as Phosphoserine- or Phosphothreonine-Binding Modules. Science 283, 1325-1328, doi:10.1126/science.283.5406.1325 (1999); Edwin, F., et al., HECT Domain-containing E3 Ubiquitin Ligase Nedd4 Interacts with and Ubiquitinates Sprouty2. Journal of Biological Chemistry 285, 255-264, doi:10.1074/jbc.M109.030882 (2010); Spagnol, G. et al. Structural Studies of the Nedd4 WW Domains and Their Selectivity for the Connexin43 (Cx43) Carboxyl Terminus. Journal of Biological Chemistry 291, 7637-7650, doi:10.1074/jbc.m115.701417 (2016) Gao, S. et al. Ubiquitin Ligase Nedd4L Targets Activated Smad2/3 to Limit TGF-β Signaling. Molecular Cell 36, 457-468, doi:10.1016/j.molcel.2009.09.043 (2009).

Figure 4A:
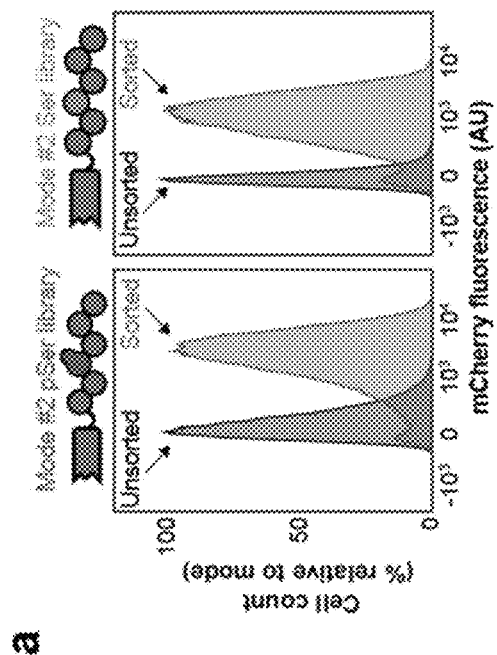
Figure 4C:
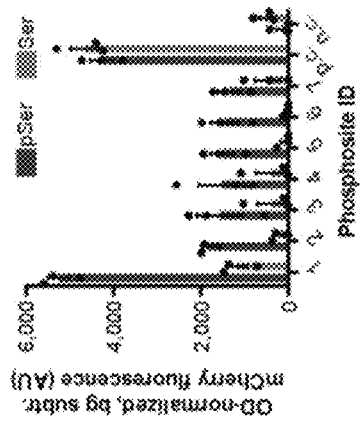
Figure 4D:
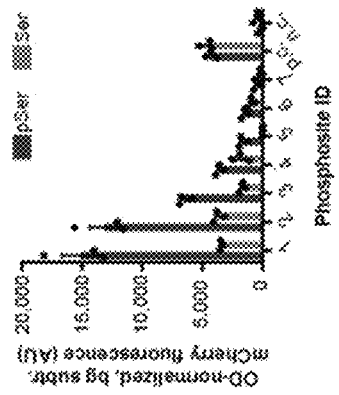
Figure 11B:
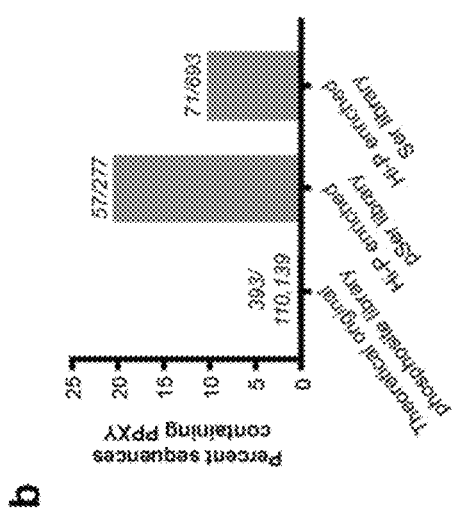
FIGS. 11A and 11B shows FACS screening of phosphoprotein interactions with NEDD4 and NEDD4-2 WW2 domains.
Figure 11A:
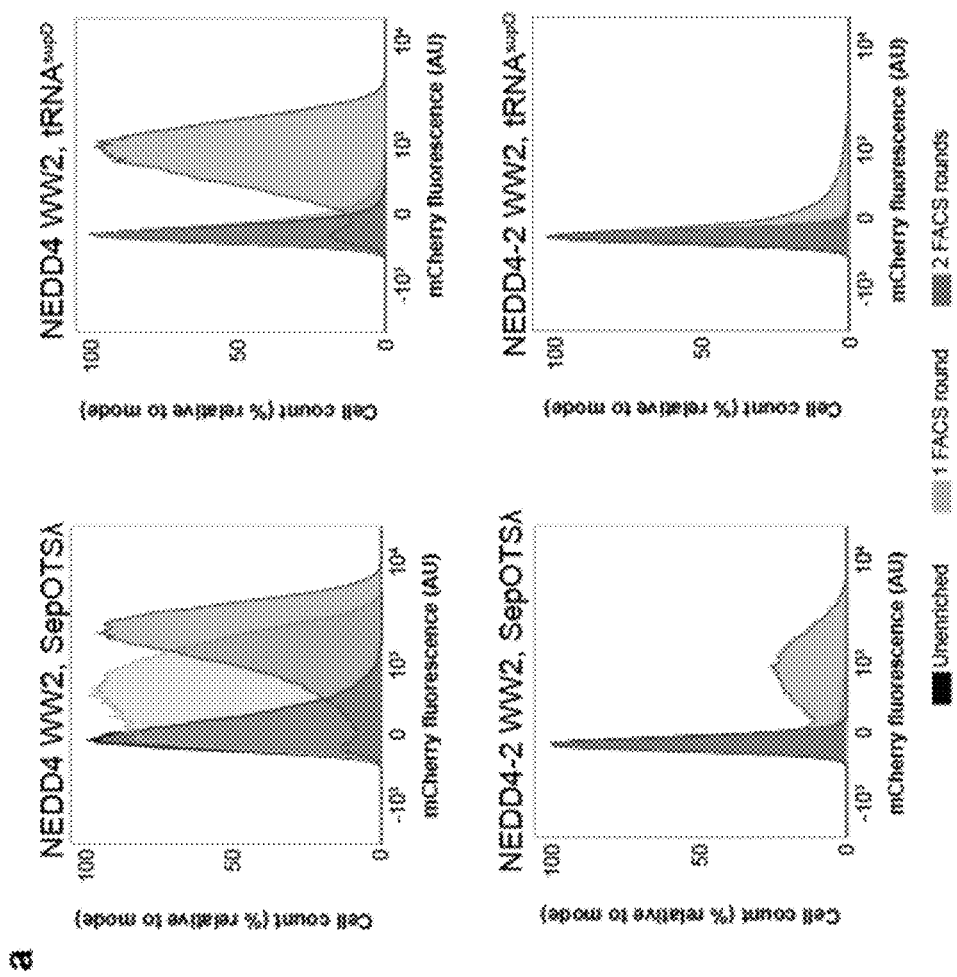
Figure 12A:
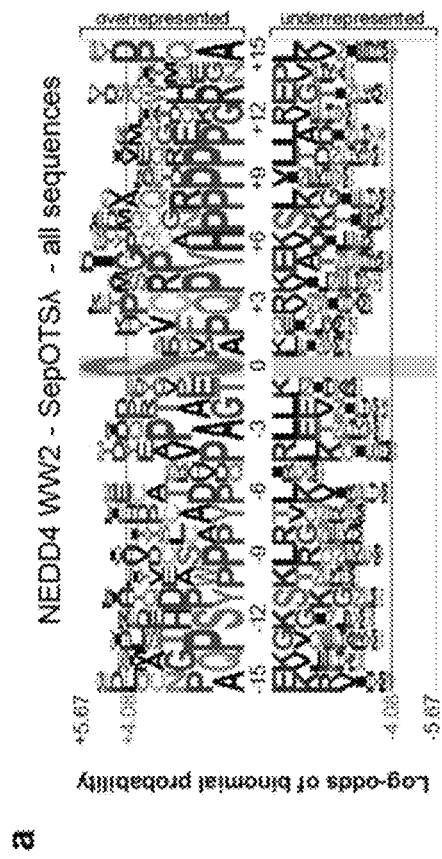
FIGS. 12A to 12F show phosphopeptide ligand sequence analysis for phosphopeptide-interacting NEDD4 WW2 domain.
Figure 12B:
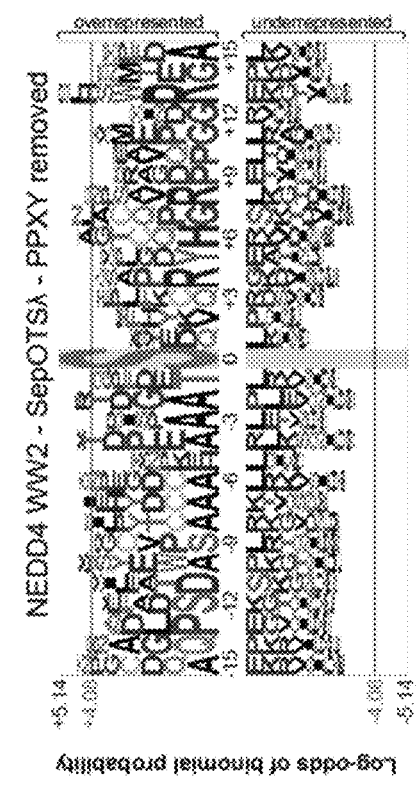
Figure 12C:
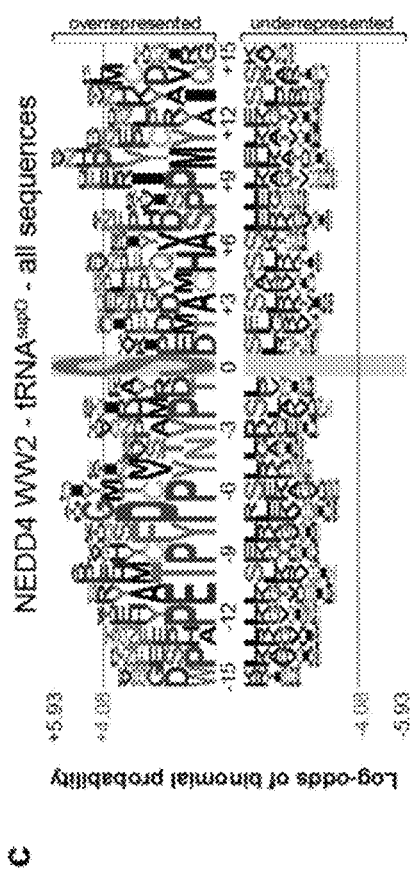

Consistent with these mixed binding modes, reconstituted mCherry fluorescence was observed from both pSer- and Ser-encoding libraries (FIG. 4A, FIG. 11A). In all fluorescent bacterial populations, a high degree of enrichment of proteins containing the PPXY motif (where X is any amino acid) was observed (FIG. 11B). The PPXY motif is a well-known WW domain binding motif, demonstrating that Hi-P can correctly identify WW domain specific interactions (FIG. 4B). See Yang, et al., Nedd4 and Nedd4-2: closely related ubiquitin-protein ligases with distinct physiological functions. Cell Death & Differentiation 17, 68-77, doi: 10.1038/cdd.2009.84 (2009). To analyze the importance of pSer or Ser incorporation in sorted populations, plasmid libraries from FACS-sorted cells encoding pSer or Ser were isolated and retransformed into both strains encoding pSer and Ser. Interestingly, the plasmids derived from pSer-encoding fluorescent populations yielded higher fluorescence signals upon pSer incorporation compared to Ser, while the plasmids derived from Ser-encoding fluorescent populations showed similar fluorescence levels with the incorporation of either pSer or Ser. This result suggests that site-specific incorporation of pSer or Ser into the same protein library may be able to identify protein-protein interactions in mixed binding modalities via Hi-P. Furthermore, motif analysis revealed no sequence element patterns characteristic of NEDD4 WW2 interactors which lacked the PPXY motif, further illustrating that Hi-P can identify pSer-specific interactions that could not be identified using motif analysis (FIGS. 11-12). For clonal validation, twenty 20 NEDD4 WW2 candidate interacting phosphoproteins were individually expressed, and fluorescent analysis was repeated by incorporating either pSer and Ser (FIGS. 4C and 13). Many of these NEDD4 WW2 interactions exhibited enhanced fluorescence when encoding pSer compared to Ser. Interestingly, a similar line of experiments showed that some PPXY-containing NEDD4 WW2 binding sites, culled from both Ser- and pSer-encoding populations, showed more comparable fluorescence with either pSer or Ser, while others yielded starkly greater fluorescence when encoding pSer compared to Ser (FIG. 4D). These observations are consistent with the mixed binding modalities of the NEDD4 WW2 domain and highlight an advantage of using genetically encoded phosphorylation in the context of a functional human phosphoproteome screen according to the present methods.

FIGS. 3A to 3F illustrates the detection of phosphoprotein/NEDD4 WW2 interactions, according to an embodiment of the present methods, using phosphopetides provided by expressing a library of phosphopeptide-encoding oligonucleotides.

pSer- and Ser-encoding phosphoprotein interactions with NEDD4 and NEDD4-2 WW2 domains were detected using the present methods, as shown in FIGS. 3A and 10. FIG. 3A shows results for NEDD4 WW2, and FIG. 11 shows results for both NEDD4 and NEDD4-2 WW2 domains. Experiments with cells co-expressing NEDD4 WW2 or NEDD4-2 WW2, along with the present phosphoproteome library, yielded increased mean population fluorescence with either the SepOTSλ (encoding pSer) or tRNA$^{supD}$ (encoding Ser). n=$10^5$ cells for flow cytometry observation. FIG. 3B shows that experiments with WW2 from NEDD4 or NEDD4-2 resulted in enrichment of PPXY-containing proteins in both pSer- and Ser-encoding populations. The raw number of sequences containing PPXY over number of sequences in population are shown above each bar. All data is for a 1,000-read cutoff by high-throughput sequencing.

the present methods enable isolation of cell populations displaying putative pSer-enhanced or pSer-independent fluorescence signals by BiFC. pLogo analysis (see O'Shea, J. P. et al. pLogo: a probabilistic approach to visualizing sequence motifs. *Nature methods* 10, 1211-1212 (2013) can be used to visualize NEDD4 WW2 interactors identified by the present methods. pSer results that do not contain the PPXY motif are shown. Red line indicates P=0.05 significance threshold with Bonferroni correction. FIGS. 12A to 12C show shosphopeptide ligand sequence analysis for phosphopeptide-interacting NEDD4 WW2 domains. pLogo analysis of phosphoproteins identified by Hi-P (>1,000 reads by high-throughput sequencing) of FACS-derived populations isolated in C321.ΔA with either the SepOTSλ (FIGS. 12A and 12B) or tRNAsupD (FIG. 12C) using the BiFC split mCherry system for co-expression of the phosphoprotein library and the NEDD4 WW2 domain. Phosphoprotein sequences containing PPXY were excluded from analysis in FIG. 12B. Red line indicates P=0.05 significance threshold with Bonferroni correction.

FIG. 4C shows BiFC analysis of select NEDD4 WW2 Hi-P hits from pSer experiments and excluding sequences containing the PPXY motif FIG. 4D shows BiFC analysis of select NEDD4 WW2 Hi-P hits, with PPXY motif (green underlined), from pSer ($S^P$) or Ser (S) experiments. For BiFC experiments in FIGS. 4C and 4D, error bars show s.e.m. (n=3 biological replicates). n.c., negative control N-mCh-WFYSPFLE (SEQ ID NO:60) co-expressed with mouse Nedd4 WW2-C-mCh[21]; p.c., positive control N-mCh-IPGTPPPNYD (SEQ ID NO:58) co-expressed with mouse Nedd4 WW2-C-mCh[21]; AU, arbitrary units.

Figure 12D:
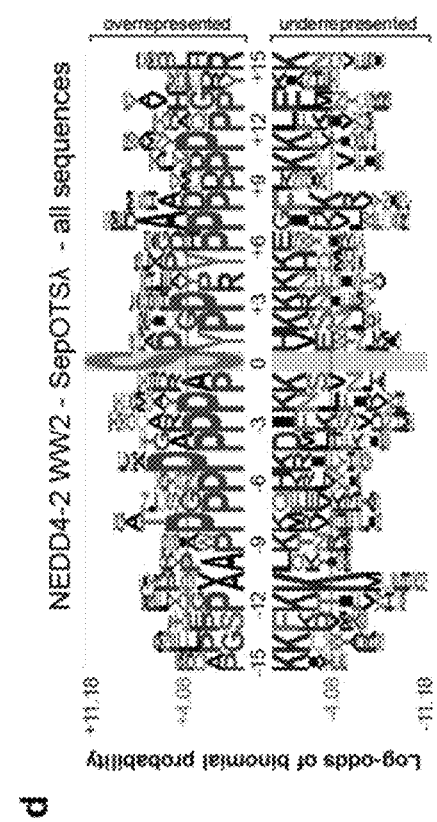
Figure 12E:
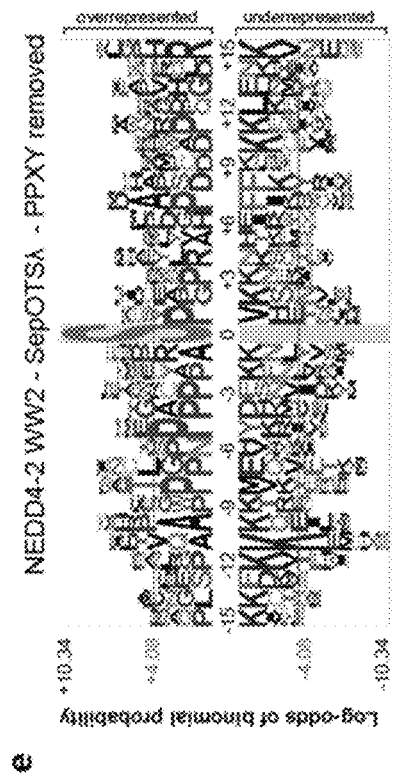
Figure 12F:
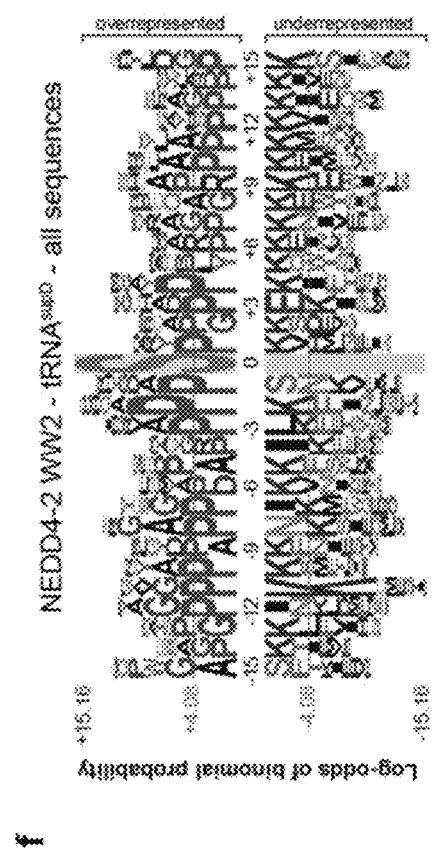
Figure 13:
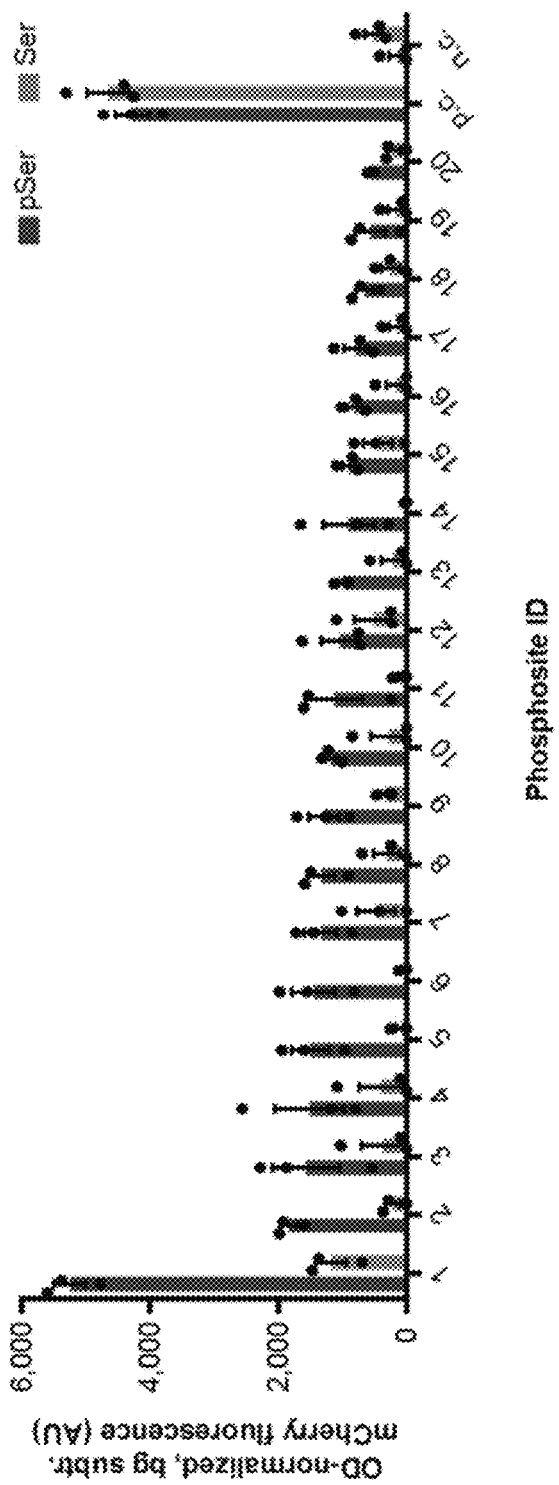
FIG. 13 shows clonal BiFC interaction analysis of NEDD4 WW2 with phosphoproteins identified by the present methods of detecting phosphorylation-dependent protein-protein interactions.

FIGS. 12D to 12F show pLogo analysis of phosphoproteins identified by Hi-P (>1,000 reads by high-throughput sequencing) of FACS-derived populations isolated in C321.ΔA with either the SepOTSλ (FIGS. 12D and 12E) or tRNAsupD (FIG. 12F) using the BiFC split mCherry system for co-expression of the phosphoprotein library and the NEDD4-2 WW2 domain. Phosphoprotein sequences containing PPXY were excluded from analysis in FIG. 12E. Red line indicates P=0.05 significance threshold with Bonferroni correction.

Example 5

In this example, clonal BiFC interaction analysis of NEDD4 WW2 with phosphoproteins was further evaluated. The phosphoproteins for this analysis were identified by the methods of detecting phosphorylation-dependent protein-protein interactions, as recited in Example 4B. Modified C321.ΔA cells harboring either the SepOTSλ or tRNA$^{supD}$ (on plasmid including SepRS9-EFSep21) plasmids were electroporated as detailed above with clonal or library vectors encoding the phosphorylation-binding domain fused to C-terminal split mCherry and the TAG-containing phosphoprotein fused to N-terminal split mCherry. Recovered cells were plated on LB agar containing 100 ng/μL ampicillin and 25 ng/μL kanamycin and grown for 18 h at 30° C. Five colonies were then inoculated in 200 μL LB with 100 ng/μL ampicillin and 25 ng/μL kanamycin in a 96-well plate. This was performed in biological triplicate. Cultures were grown for 16-18 h at 30° C., 530 rpm in a Jitterbug microplate shaker (Boekel). Cultures were then diluted to $OD_{600}$ of about 0.15 in a total of 200 μL LB supplemented with 100 ng/μL ampicillin, 25 ng/μL kanamycin, 2 mM O-phospho-L-serine, 1 mM IPTG, 0.2% arabinose and 100 ng/μL anhydrotetracycline, and grown at 30° C., 530 rpm in the microplate shaker for 24 h. These conditions were found to be sufficient to detect appreciable fluorescent signal with the BiFC system via time-course assay. 100 μL cells were then diluted in 100 μL LB and $OD_{600}$ and fluorescence (580 nm excitation, 610 nm emission) readings were taken on a Synergy H1 microplate reader (BioTek). In parallel, the same strains were grown under identical conditions except without anhydrotetracycline (no phosphoprotein expression) to establish baseline strain fluorescence values for background subtraction. Cells were diluted to ensure fluorescence and $OD_{600}$ measurements fell within the linear range of the plate reader.

FIG. 13 shows clonal BiFC interaction analysis of NEDD4 WW2 with phosphoproteins identified by the present methods of detecting phosphorylation-dependent protein-protein interactions. Phosphoproteins lacking the PPXY motif identified as candidate interactors with NEDD4 WW2 in the presence of the SepOTSλ by Hi-P were expressed clonally in the BiFC mCherry system with either the SepOTSλ or tRNA$^{supD}$. SepOTSλ-dependent mCherry signals were obtained for most phosphoproteins. Error bars show s.e.m. (n=3 biological replicates). p.c., positive control N-mCh-IPGTPPPNYD (SEQ ID NO:58) co-expressed with mouse Nedd4 WW2-C-mCh (Lu, P.-J., et al. (1999)); n.c., N-mCh-WFYSPFLE (SEQ ID NO:60) co-expressed with mouse Nedd4 WW2-C-mCh; AU, arbitrary units.

For data analysis, background-subtracted fluorescence values were normalized by $OD_{600}$ measurements, and negative values were treated as values of zero (below limit of detection). Positive and negative control interactions without TAG codons for the NEDD4 WW2 domain were previously described[21]. The negative control for the 14-3-3 experiment was identified by Hi-P as a candidate interactor with NEDD4 WW2, indicating this protein is capable of participating in binding interactions via but does not interact promiscuously with various phospho-binding domains.

Example 6

In this example, GST pull-down assays were used to confirm the phosphorylation-dependent protein-protein interactions detected in the previous examples. GST-fusion phosphoproteins with C-terminal 6xHis tags were expressed clonally with either the SepOTSλ or tRNA$^{supD}$ (on plasmid including SepRS9-EFSep21) in C321.ΔA in 500 mL cultures and purified using Ni-NTA resin as detailed in the library preparation section. 14-3-3β and 14-3-3σ with C-terminal 6xHis tags were expressed with C-terminal split mCherry using the same expression vector as for the previous example, transformed into BL21, and purified in the same fashion as the GST-fusion phosphoproteins with Ni-NTA.

Purified proteins were buffer exchanged using Amicon Ultra-0.5 10 kDa MWCO columns in storage buffer containing 50 mM Tris pH 7A, 150 mM NaCl, 500 μM EDTA, 500 μM EGTA, 20% glycerol, 1 mM DTT, 50 mM NaF, and 1 mM NaVO$_4$. 10 μg GST-phosphoprotein calculated by Coomassie-stained SDS-PAGE was immobilized on 10 μL pre-equilibrated glutathione HiCap resin (Qiagen) in a total of 100 μL binding buffer (50 mM Tris pH 7.4, 500 mM NaCl, 500 μM EDTA, and 1 mM DTT) and incubated end-over-end at 4° C. for 1 h. The resin was then washed twice with 100 μL binding buffer, resin was spun at 100×g for 1 minute and supernatant was removed. 2 μg 14-3-3 proteins (as estimated by Coomassie stain) was then added to the resin in 10 μL total binding buffer, and 10 μL slurry was removed for SDS-PAGE analysis (input). 95 μL binding buffer was then added, and sample was incubated end-over-end for 14-16 h at 4° C. Resin was then washed twice with 100 μL binding buffer, buffer was removed after spin, and finally 5 μL binding buffer was added to the resin. This final 10 μL slurry was used for SDS-PAGE analysis (output). Input and output samples were incubated at 95° C. for 5 minutes in 10 μL 2x Laemmli buffer, and 0.5 μL of each sample was run per lane in 10 μL total sample volume on 4-15% acrylamide gels (Bio-Rad). FIG. 10A shows the Phos-tag western blot of the purified fusion proteins expressed with pSer or Ser. This assay result provided additional evidence that the interactions detected in Example 3 were phosphorylation dependent.

Example 7

Figure 14A:
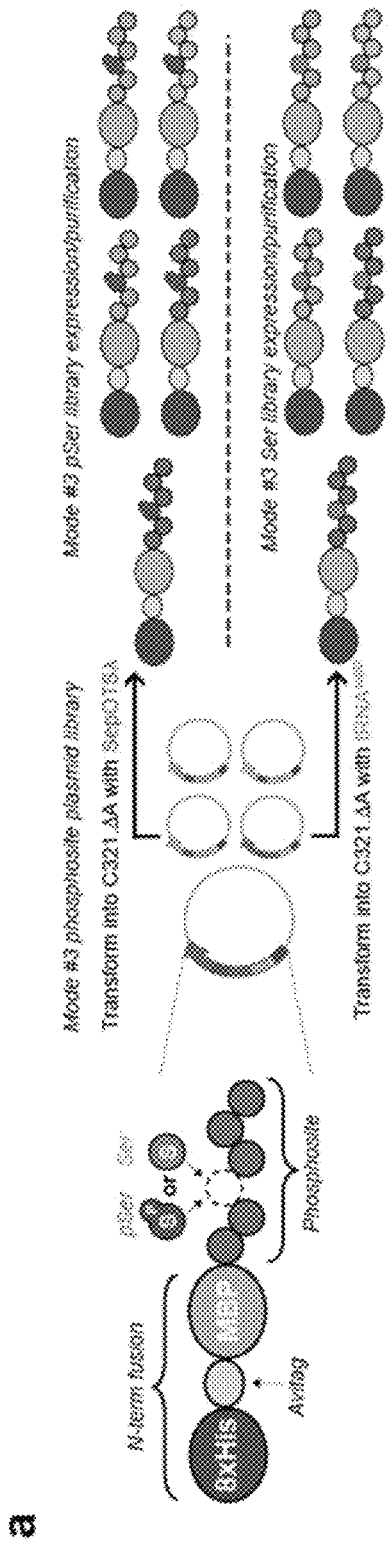
FIG. 14A illustrates mode #3 configuration of phosphosites in targeted library used for expression and purification.
Figure 14B:
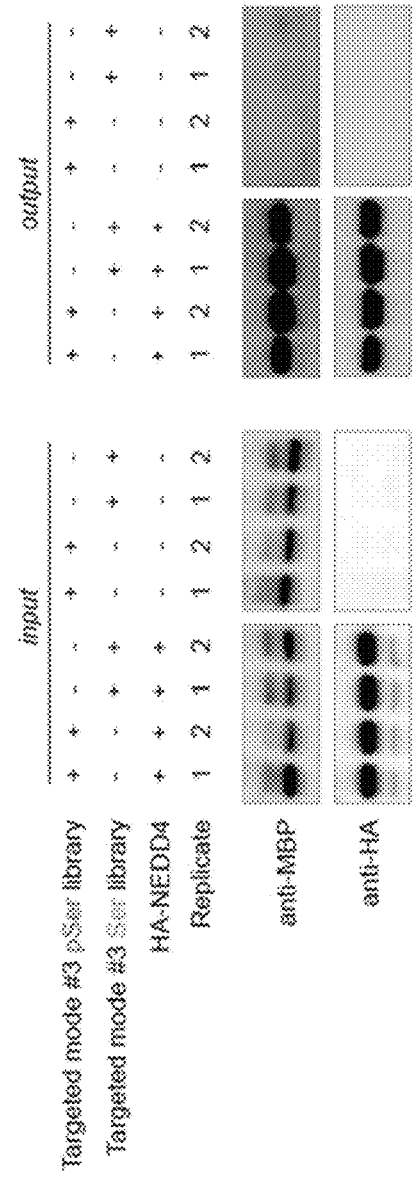
FIG. 14B shows immunoprecipitation of full-length HA-NEDD4 protein using an agarose resin conjugated with an anti-HA antibody.

This example investigated if the novel phosphosite interactions revealed by Hi-P using the isolated WW domain could be recapitulated with a full-length interaction partner expressed in a human cell line. First, a targeted library of 20 phosphosites identified from NEDD4 WW2 Hi-P experiments was expressed (those from FIGS. 4C and 13) with an MBP fusion tag to enhance expression (mode #3, FIG. 14A). Phosphosites containing PPXY sequences were excluded because this type of WW domain interaction is already well characterized. This targeted phosphosite library was spiked into mammalian cell lysates expressing full-length human NEDD4 and performed co-immunoprecipitation (co-IP) mass spectrometry experiments (FIG. 14B). To address pSer specificity, parallel experiments were performed with pSer and Ser targeted mode #3 phosphosite libraries. It was found that several of these phosphosites co-precipitated with NEDD4 in a phosphorylation-dependent manner (See Table B above). A PPXY-free phosphosite from AMOTL1 was the top candidate interactor with NEDD4 as identified by both BiFC (using just the WW2 domain) and co-IP (using the full-length NEDD4 protein), exhibiting enhanced binding with full-length NEDD4 when pSer was incorporated within the phosphosite. AMOTL1 was previously observed to interact with NEDD4-2 in a PPXY-dependent manner (See Skouloudaki, K. & Walz, G. YAP1 Recruits c-Ab1 to Protect Angiomotin-Like 1 from Nedd4-Mediated Degradation. *PLoS ONE* 7 (2012)), but the PPXY-free region identified by Hi-P has never been directly implicated in coordinating an interaction with a NEDD family protein. Overall, results between Hi-P and co-IP may differ because the full-length NEDD4 protein has four total WW domains, while Hi-P only examined the WW2 domain in isolation.

Example 8

This example we evaluated expression-based bias and experimental reproducibility of the platform to further characterize Hi-P. To better understand how phosphosite expression levels may influence identification by Hi-P, the number of Hi-P HTS reads was compared with phosphopeptide ion intensity by mass spectrometry (an indication of phosphosite expression level) for individual phosphosites.

Figure 15A:
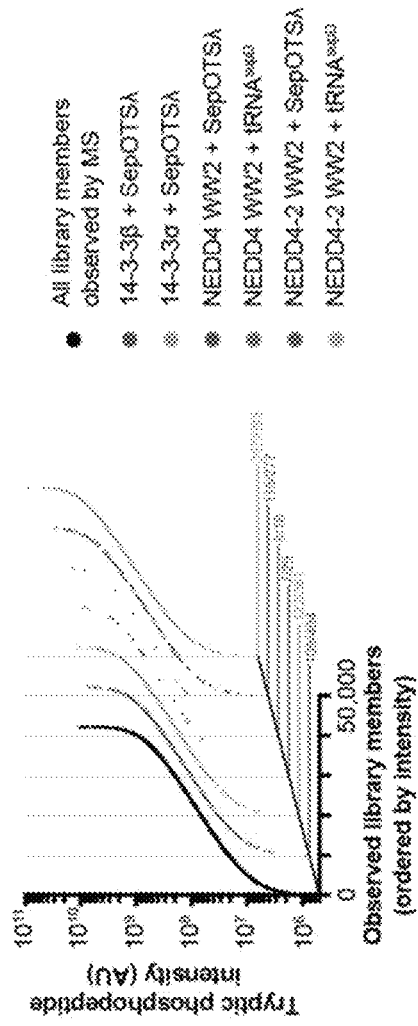
FIG. 15A shows plotted maximum phosphopeptide intensities as observed by LC-MS/MS (mode #1 phosphosites) corresponding to phosphosites identified by Hi-P (mode #2 phosphosites).
Figure 15B:
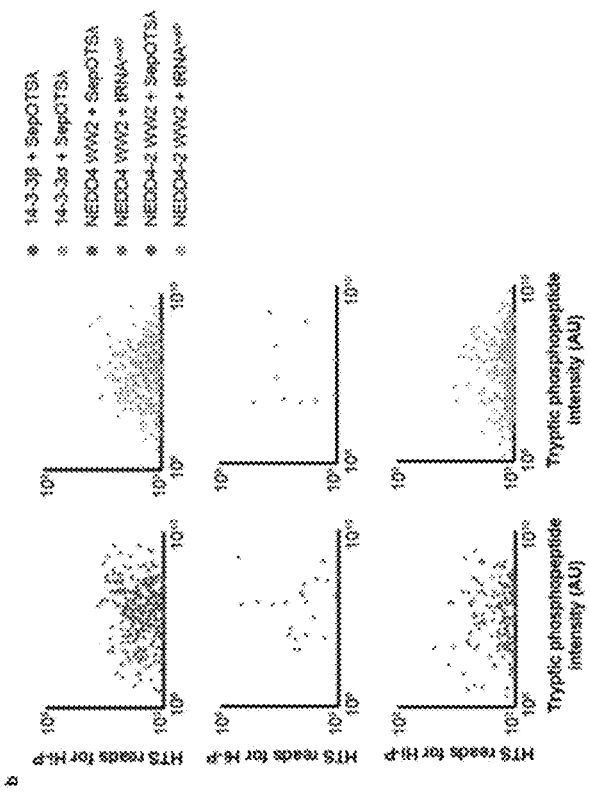
FIG. 15B compares the number of HTS reads by Hi-P of individual mode #2 phosphosites compared to the observed maximum intensity of the corresponding tryptic phosphopeptide by LC-MS/MS (mode #1 phosphosites).

FIG. 15A shows plotted maximum phosphopeptide intensities as observed by LC-MS/MS (mode #1 phosphosites) corresponding to phosphosites identified by Hi-P (mode #2 phosphosites). FIG. 15B compares the number of HTS reads by Hi-P of individual mode #2 phosphosites compared to the observed maximum intensity of the corresponding tryptic phosphopeptide by LC-MS/MS (mode #1 phosphosites). Data presented is for a 1,000 HTS read cutoff.

No correlation was seen between phosphosite ion intensity and Hi-P reads (FIGS. 15A and 15B). It is noted that phosphosite interactors with 14-3-3 isoforms were not identified by Hi-P when using tRNA$^{supD}$ (FIGS. 3B & 7), suggesting that differential expression alone of individual phosphosites cannot drive false positive BiFC interactions. The reproducibility of Hi-P was then investigated by performing three biological replicate experiments for 14-3-3β with the pSer-phosphosite library and the WW2 domain of NEDD4 with either the pSer- or Ser-phosphosite libraries (Table C).

FIGS. 16A-16D illustrate biological triplicates with each replicate R1, R2, and R3 in the triplicate identified. The numbers within each replicate correspond to the number of phosphosite sequences observed by Hi-P in each of the replicates, represented as a Venn diagram and showing the overlap between each replicate. FIG. 16A shows overlap between phosphosite sequences observed in biological triplicate samples by Hi-P using the 14-3-3β isoform and the mode #2 phosphosite library expressed using SepOTSλ. R1 included 125, 147, 238, and 400 phosphosite sequences, R2 included 117, 125, 238, and 347 phosphosite sequences, and R3 included 117, 147, 238, and 340 phosphosite sequences. FIG. 16B shows overlap of phosphosite sequences by Hi-P in biological triplicate mapping to proteins that had been previously-observed candidate interactors with 14-3-3β. R1 included 54, 72, 110, and 152 phosphosite sequences, R2 included 54, 54, 110, and 139 phosphosite sequences, and R3 included 54, 72, 110, and 147 phosphosite sequences. FIG. 16C shows overlap between phosphosite sequences observed in biological triplicate samples by Hi-P using the NEDD4 WW2 domain and the mode #2 phosphosite library expressed using SepOTSβ. R1 included 7, 17, 18, and 411 phosphosite sequences, R2 included 7, 18, 40, and 164 phosphosite sequences, and R3 included 17, 18, 40, and 389 phosphosite sequences. FIG. 16D shows overlap between phosphosite sequences observed in biological triplicate samples by Hi-P using the NEDD4 WW2 domain and the mode #2 phosphosite library expressed using tRNA$^{supD}$. R1 included 22, 64, 71, and 386 phosphosite sequences, R2 included 34, 64, 71, and 477 phosphosite sequences, and R3 included 22, 34, 64, 336 phosphosite sequences. R=replicate.

Considerable overlap between data sets for 14-3-3β was seen (FIGS. 16A & B), but less for the NEDD4 WW2 domain (FIGS. 16C & D). These results indicate that various "bait" structures may behave differently in Hi-P experiments due to their size, ligand binding kinetics, or binding modalities, which may in turn affect reproducibility. As demonstrated above, low-throughput experiments using full-length proteins or functional domains can be conducted to validate interactions predicted by Hi-P.

EXEMPLARY EMBODIMENTS

Exemplary embodiments provided in accordance with the presently disclosed subject matter include, but are not limited to, the claims and the following embodiments:

1. A method of preparing a library of phosphopeptide-encoding oligonucleotides, the method comprising:
   selecting phosphopeptide sequences matching regions of native protein sequences comprising (i) a phosphorylation-susceptible residue and (ii) 0 to 15 or more residues on each side of the phosphorylation-susceptible residue;
   converting the selected phosphopeptide sequences into phosphopeptide-encoding nucleic acid sequences; and
   synthesizing a library of phosphopeptide-encoding oligonucleotides having the reverse-translated phosphopeptide-encoding nucleic acid sequences.

2. The method of embodiment 1, wherein the phosphopeptide-encoding oligonucleotides comprise primer annealing sites on each side of the phosphopeptide sequences (such as universal primer annealing sites or orthogonal primer annealing sites).

3. The method of embodiment 1 or 2, further comprising amplifying the phosphopeptide-encoding oligonucleotides.

4. The method of any of the foregoing embodiments, wherein the phosphopeptide-encoding oligonucleotides comprise restriction enzyme cleavage sites on each side of the phosphopeptide sequences (such as KpnI at the 5' end and HindIII at the 3' end).

5. The method of any of the foregoing embodiments, further comprising ligating the phosphopeptide-encoding oligonucleotides, or an amplification product of the phosphopeptide-encoding oligonucleotides, to vectors (such as pNAS1 B or pCRT7).

6. The method of embodiment 5, further comprising transforming the vectors into cells (such as bacterial cells, for example E. coli cells, preferably C321.ΔA cells).

7. The method of embodiment 6, wherein the cells further contain a plasmid that facilitates ribosomal incorporation of a phosphorylated amino acid into a protein from a codon (such as a SepOTSλ plasmid).

8. The method of embodiment 6, further comprising transforming the vectors into cells that do not contain a plasmid that facilitates ribosomal incorporation of a phosphorylated amino acid into a protein from a codon (such as a SepOTSλ plasmid).

9. The method of any of the foregoing embodiments, wherein the phosphopeptide sequences are selected by:
   identifying phosphorylation-susceptible amino acid sequences comprising at least one phosphorylation-susceptible residue in full-length native protein sequences; and
   elongating the phosphorylation-susceptible amino acid sequences to include residues from the matching full-length native protein sequences on one or both sides of the phosphorylation-susceptible residue, thereby providing phosphopeptide sequences, for example elongating to include up to 15 residues from one or both sides, and/or providing phosphopeptide sequences comprising 16 to 31 residues. The phosphopeptide sequences can be sequences of amino acids of any length, including but not limited to a full length protein.

10. A set or kit of plasmids comprising amplification products of the library of phosphopeptide-encoding oligonucleotides made according to any of the foregoing embodiments.

11. A set or kit of cells comprising amplification products of the library of phosphopeptide-encoding oligonucleotides made according to any of embodiments 1 to 9.

12. The plasmids of embodiment 10 or the cells of embodiment 11, wherein the phosphopeptide-encoding oligonucleotides further comprise a region encoding a first portion of a reporter.

13. A method of using the plasmids or the cells of embodiment 12 to detect or visualize a phosphorylation-dependent protein-protein interaction comprising:

expressing the phosphopeptide-encoding oligonucleotides to provide a first fusion protein comprising a phosphopeptide and a first portion of a reporter;

providing a second fusion protein comprising a candidate having a known or suspected phosphoprotein-binding region and a second portion of the reporter; and detecting a signal from interaction of the first fusion protein and the second fusion protein.

14. The method of embodiment 13, wherein the reporter is an enzyme, (such as horseradish peroxidase, beta-galactosidase or alkaline phosphatase), an affinity tag, or a protein that modulates resistance or sensitivity to antibiotics.

15. The method of embodiment 13, wherein the reporter is a fluorescent protein, and the signal is detected by detecting a bimolecular fluorescence complementation (BiFC) signal from interaction of the first fusion protein and the second fusion protein.

16. The method of embodiment 15, wherein the BiFC signal is detected by flow cytometry.

17. The method of embodiment 15, further comprising selecting a cell using Fluorescence-Activated Cell Sorting (FACS) and sequencing the phosphopeptide-encoding region of the first polynucleotide.

18. The method of any of embodiments 13 to 17, further comprising identifying the candidate as having a phosphoprotein-binding region.

19. The method of embodiment 18, further comprising identifying the candidate as comprising an unrecognized phosphoprotein-binding motif.

20. A set or kit of oligonucleotides, wherein each of the oligonucleotides has a region that encodes a phosphopeptide, wherein the set or kit comprises at least 10 different oligonucleotides (alternatively at least 100, 1000, 3,000, 10,000, 30,000, or 100,000 different oligonucleotides).

21. The set or kit of embodiment 20, wherein each of the oligonucleotides comprises a codon that codes for a phosphorylated residue in the presence of one or more enzymes or factors (such as Sep aminoacyl-tRNA synthetase and engineered elongation factor Tu).

22. The set or kit of embodiment 21, wherein the codon is TAG or UAG.

23. The set or kit of any of embodiments 20 to 22, wherein the oligonucleotides are contained in a plasmid, vector, or cell.

24. The set or kit of any of embodiments 20 to 23, wherein the oligonucleotides are contained in cells comprising plasmid encoding tRNA$^{supD}$.

25. The set or kit of any of embodiments 20 to 24, wherein the oligonucleotides are contained in cells comprising a vector encoding tRNA$^{supD}$ (for example, a pNAS1R vector or a pCRT7 vector).

26. The set or kit of any of embodiments 20 to 25, wherein the set or kit comprises oligonucleotides encoding phosphopeptides corresponding to essentially all proteins susceptible to phosphorylation (which may include multiple phosphopeptides corresponding to a single protein, when that protein can be phosphorylated at multiple different positions), or another group of protein regions susceptible to phosphorylation, such as essentially all eukaryotic proteins, essentially all prokaryotic proteins, essentially all mammalian proteins, essentially all human proteins, essentially all insect proteins, essentially all plant proteins, or a combination thereof. Any of the foregoing can be essentially all proteins susceptible to serine phosphorylation, essentially all proteins susceptible to threonine phosphorylation, essentially all proteins susceptible to tyrosine phosphorylation, or a combination thereof.

27. The set or kit of any of embodiments 20 to 26, wherein the set or kit comprises oligonucleotides encoding essentially all phosphopeptides of a phosphoproteome (that is, all phosphopeptides derived from full proteins in a phosphoproteome) (such as a eukaryotic phosphoproteome, a prokaryotic phosphoproteome, a mammalian phosphoproteome, a human phosphoproteome, an insect phosphoproteome, a plant phosphoproteome, or another phosphoproteome). Any of the foregoing phosphoproteomes can be a serine phosphoproteome, a threonine phosphoproteome, a tyrosine phosphoproteome, or a combination thereof).

28. The set or kit of any of embodiments 20 to 27, wherein each polynucleotide further comprises a sequence encoding a reporter protein or portion thereof.

29. The set or kit of embodiment 28, wherein the protein is a fluorescent protein selected from the group consisting of ZsGreen1, ZsYellow1, DsRed2, GFP, eGFP, YFP, eYFP, BFP, eBFP, CFP, eCFP, FP, AmCyan 1, DsRed-Express, AsRed2, HcRed1,mPlum, mCherry, tdTomato, mStrawberry, J-Red, DsRed-monomer, mOrange, mKO, MCitrine, Venus, Ypet, EYFP, Emerald, CyPet, mCFPm, Cerulean, and T-Sapphire.

30. The set or kit of embodiment 29, wherein the protein is selected from the group consisting of Beta lactamase, DHFR, focal adhesion kinase, Gal4, Horseradish peroxidase, LacZ, luciferase, TEV, and ubiquitin.

31. The set or kit of embodiment 29, wherein the fluorescent protein is selected from the group consisting of mCherry, Cerulean, GFP, and YFP.

32. The set or kit of any of embodiments 20 to 31, wherein each polynucleotide further comprises a sequence encoding an affinity tag selected from the group consisting of glutathione s-transferase (GST) tags, maltose binding protein (MBP), chitin binding protein, cellulose-binding protein, calmodulin binding peptide, streptavidin binding peptide (SBP), poly-arginine, poly-histidine, FLAG (DYKDDDDK) (SEQ ID NO:62), 3x FLAG, streptavidin (strep)-tag II, c-myc, RNaseA S-peptide (S-tag), natural histidine affinity tag (HAT), alkaline phosphatase (ALP), J3-D-galactosidase, beta-D-glucose oxidase, luciferase, peroxidase, and xanthine oxidase.

33. The set or kit of any of embodiments 20 to 32, wherein each of the phosphopeptides is from 16 to 31 amino acids in length and/or comprises one or more phosphoserines, phosphotyrosines, phosphothreonines, acetylated residues, methylated residues, or combinations thereof.

34. The set or kit of embodiment 33, wherein the set or kit comprises at least 10 different phosphopeptides (alternatively at least 100, 1000, 3,000, 10,000, 30,000, or 100,000 different phosphopeptides).

35. A method of screening candidates for a phosphorylation-dependent protein-protein interaction comprising:

providing a first fusion protein comprising a phosphopeptide and a first portion of a reporter;

providing a second fusion protein comprising a candidate having a suspected phosphoprotein-binding region and a second portion of the reporter;

detecting a signal from interaction of the first fusion protein and the second fusion protein; and identifying the candidate as having a phosphopeptide-binding region. 36. The method of embodiment 35, where the candidate is an antibody or antibody-like protein of known or unknown phosphoprotein-binding properties.

37. The method of embodiment 35 or 36, further comprising identifying the candidate as comprising an unrecognized phosphoprotein-binding motif.

38. The method of any of embodiments 35 to 37, wherein the interaction is detected inside a cell.

39. The method of any of embodiments 35 to 37, wherein the interaction is detected outside a cell (for example, in protein extracts).

40. The method of any of embodiments 35 to 39, wherein the reporter is an enzyme, (such as horseradish peroxidase, beta-galactosidase or alkaline phosphatase), an affinity tag, or a protein that modulates resistance or sensitivity to antibiotics.

41. The method of any of embodiments 35 to 40, wherein the first fusion protein is expressed within a cell by a first polynucleotide transformed into the cell, wherein the first polynucleotide comprises a phosphopeptide-encoding portion.

42. The method of embodiment 41, wherein the second fusion protein is expressed within the cell by a second polynucleotide transformed into the cell.

43. The method of any of embodiments 35 to 42, further comprising sequencing the first polynucleotide from a cell having an identified candidate.

44. The method of embodiment 43, further comprising sequencing the second polynucleotide from a cell having an identified candidate to identify a region encoding the phosphoprotein-binding region.

45. The method of any of embodiments 35 to 44, wherein the reporter is a fluorescent protein, and the signal is detected by detecting a bimolecular fluorescence complementation (BiFC) signal from interaction of the first fusion protein and the second fusion protein.

46. The method of embodiment 45, wherein the BiFC signal is detected by flow cytometry.

47. The method of embodiment 45, further comprising selecting a cell using Fluorescence-Activated Cell Sorting (FACS) and sequencing the phosphopeptide-encoding region encoded by the first polynucleotide, or the phosphoprotein-binding region encoded by the second polynucleotide, or both of the first and second oligonucleotides.

The foregoing description of exemplary or preferred embodiments should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

We claim:

1. A method of preparing a library of phosphopeptide-encoding oligonucleotides, the method comprising:
   selecting a plurality of phosphopeptide sequences from full-length native protein sequences, comprising:
   identifying, in a full-length native protein sequence, a plurality of phosphorylation-susceptible amino acid sequences, wherein each phosphorylation-susceptible amino acid sequence comprises a single phosphorylation-susceptible residue;
   elongating each phosphorylation-susceptible amino acid sequence to include up to 15 residues from the full-length native protein sequence on each side of the single phosphorylation-susceptible residue, wherein each phosphopeptide sequence, of the plurality of phosphopeptide sequences, comprises 16 to 31 residues;
   in silico converting each phosphopeptide sequence, of the selected plurality of phosphopeptide sequences, into a phosphopeptide-encoding nucleic acid sequence, wherein the single phosphorylation-susceptible residue is encoded as a codon that does not encode a phosphorylation-residue in nature, and wherein the single phosphorylation-susceptible residue is encoded by a codon of thymine, adenine, and/or guanine; and
   synthesizing a library of phosphopeptide-encoding oligonucleotides having the phosphopeptide-encoding nucleic acid sequences, wherein each phosphopeptide-encoding oligonucleotide, of the library of phosphopeptide-encoding oligonucleotides has one of the phosphopeptide-encoding nucleic acid sequences.

2. The method of claim 1, wherein each phosphopeptide-encoding oligonucleotide, in the library of phosphopeptide-encoding oligonucleotides, comprises primer annealing sites on each side of the phosphopeptide-encoding nucleic acid sequence.

3. The method of claim 1, further comprising amplifying the phosphopeptide-encoding oligonucleotides.

4. The method of claim 1, wherein each phosphopeptide-encoding oligonucleotide, in the library of phosphopeptide-encoding oligonucleotides, comprise restriction enzyme cleavage sites on each side of the phosphopeptide-encoding nucleic acid sequence.

5. The method of claim 1, further comprising ligating each phosphopeptide-encoding oligonucleotide in the library of phosphopeptide-encoding oligonucleotides, to vectors.

6. The method of claim 5, further comprising transforming the vectors into cells.

7. The method of claim 6, wherein the cells further contain a plasmid that facilitates ribosomal incorporation of a phosphorylated amino acid into a protein from one or more codons.

* * * * *

SEQUENCE LISTING

```
<160> NUMBER OF SEQ ID NOS: 74

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
acccaaagaa ctcgattcct                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
atggaggtcc ttttgttcct                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
agcgtcgaat gaatgcatac                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 4
aacttcaggg ctgtgtctaa                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
agaccaggat ggctgataag                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
gtttcgtgcc cacatatacc                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
aatccttgcg tcaatggttc                                                    20

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
gggttctcgg attttacacg                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
tgtcgtgcct ctttatctgt                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
gcttcggtgt atcggaaatg                                                    20

<210> SEQ ID NO 11
```

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
tattcatgct tggacggact                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
actatgtacc gcttgttgga                                                   20

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
ttccgtttat gctttccagc                                                   20

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct

<400> SEQUENCE: 14
tccttggagt ttagagcgag                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic Construct

<400> SEQUENCE: 15
tgcaagtgta caaatccagc                                                   20

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
gaacggtgat ccctttccta                                                   20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
```

```
gagatgagta gacgagtggg                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
atggtcactg actcgcatta                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
tgtcatatgc taacgtccgt                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
tggctacttt cttagcggaa                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
ttataatcat cctccccggc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
ccaaatagga tgtgtgctcg                                              20

<210> SEQ ID NO 23
<211> LENGTH: 128
<212> TYPE: DNA
<213> ORGANISM: Artificial Sequence
<220> FEATURE:
<223> OTHER INFORMATION: Synthetic Construct

<400> SEQUENCE: 23
ccgggatcct acctgacgct ttttatcgca actctctact gtttctccat acccgttttt   60
tgggctaaca ggaggaatta catatgtcta gagtttaaac cggaccgtgt acattataag  120
agctcccg                                                          128
```

<210> SEQ ID NO 24
<211> LENGTH: 411
<212> TYPE: DNA
<213> ORGANISM: Artificial Sequence
<220> FEATURE:
<223> OTHER INFORMATION: Synthetic Construct

<400> SEQUENCE: 24

```
gaggaattac atatgtcagg cttaccgccc ggatgggaag aaaaacaaga tgagcgcggt    60
cgctcttact acgtcgatca caattcccgt acaacaactt ggacgaagcc cactgtggag   120
ctcggagcgg ctgcaggagg aagcggaggc gcgctgaagg gcgagatcaa gcagaggctg   180
aagctgaagg acggcggcca ctacgacgct gaggtcaaga ccacctacaa ggccaagaag   240
cccgtgcaac tgcccggcgc ctacaacgtc aacatcaagt ggacatcac ctcccacaac    300 gaggactaca ccatcgtgga acagtacgaa cgcgccgagg ccgccactc caccggcggc    360 atggacgagc tgtacaagca ccaccaccac caccactaat tataaaaaaa a           411
```

<210> SEQ ID NO 25
<211> LENGTH: 480
<212> TYPE: DNA
<213> ORGANISM: Artificial Sequence
<220> FEATURE:
<223> OTHER INFORMATION: Synthetic Construct

<400> SEQUENCE: 25

```
gtccatatgt caccccttcc gccaggttgg gaagagcgtc aagacatcct gggtcgtact    60
tattacgtta accacgagtc acgtcgcacc cagtggaagc gtccaacacc ggagctcatc   120
ggtcatatgg gattttttgcc gaaggggtgg gaggtccgtc atgcgcccaa tggtcgtcca   180
tttttcatcg accacaacac aaagactacg acgtgggagg acccacgcct tgagctctac   240
tggcatatgg ggcctcttcc ccccggatgg gaggaacgca ctcacactga tggacgcatt   300 tttttatca atcacaacat taagcgcacg caatgggagg acccacgctt ggagctctgg   360
aaccatatgc cgggattacc gagcggatgg gaagaacgca agatgccaa agggcgtacc   420 tactatgtga accataacaa tcgcactacg acatggacgc gccccattat ggagctctac   480
```

<210> SEQ ID NO 26
<211> LENGTH: 763
<212> TYPE: DNA
<213> ORGANISM: Artificial Sequence
<220> FEATURE:
<223> OTHER INFORMATION: Synthetic Construct

<400> SEQUENCE: 26

```
gagtcactca tatgacgatg gacaaatcag agctggtaca gaaggcaaaa ctggctgaac    60
aagctgagcg ttacgacgac atggcggctg caatgaaggc ggttacggaa caagggcacg   120
agctgagtaa tgaggaacgc aacttattaa gtgttgcgta caaaaatgta gtcggcgcac   180
gtcgtagtag ttggcgcgtt atcagcagta ttgagcagaa accgagcgc aacgagaaga    240 agcaacaaat gggtaaagaa taccgtgaaa agatcgaagc cgaactgcag gatatttgta   300
atgatgtgct tgaattgctg gataagtact tgatccccaa cgctacacaa cccgaatcga   360 aagttttta ccttaaaatg aagggcgact attttcgcta tcttagcgag gtggctagtg     420
gtgataacaa gcaaaccacc gtgtcaaact cgcaacaagc ataccaggaa gcattcgaga   480
ttagcaagaa ggagatgcag cccacgcacc ctatccgttt gggccttgcc ctgaattcct   540
cagttttcta ctacgaaatc ttgaactctc cagagaaagc gtgctcgctg gccaaaacgg   600
```

| cttttgacga ggctatcgca gaattggaca cactgaatga ggaaagctat aaagattcga | 660 |
| cacttattat gcagttatta cgtgataatc ttacactgtg gaccagcgag aaccaaggcg | 720 |
| acgaagggga cgctggagaa ggagagaacg agctcagtca gtc | 763 |

<210> SEQ ID NO 27
<211> LENGTH: 769
<212> TYPE: DNA
<213> ORGANISM: Artificial Sequence
<220> FEATURE:
<223> OTHER INFORMATION: Synthetic Construct

<400> SEQUENCE: 27

| gagtcactca tatggaacgc gcgtctttaa ttcagaaagc caagttagct gagcaggcgg | 60 |
| agcgttacga agacatggca gcgtttatga aggcgccgt cgagaaaggg gaagaattat | 120 |
| cgtgtgaaga gcgcaatttg ttgtcagtgg catacaaaaa tgtcgtgggt ggtcagcgtg | 180 |
| cagcgtggcg tgtgctgagc agtatcgaac aaaagtcaaa tgaggaaggt tccgaagaaa | 240 |
| aaggccccga agttcgcgag tatcgtgaga aggttgagac tgagctgcaa ggggtttgcg | 300 |
| acaccgtgct tggactgctg gactcccact tgattaaaga agcgggtgat gccgaatccc | 360 |
| gtgtcttcta cttaaaaatg aaggggggact attaccgtta tttagccgag gtagcaacgg | 420 |
| gcgacgacaa aaagcgtatt atcgactcag ctcgttctgc ctatcaggaa gcgatggata | 480 |
| tttcaaagaa agagatgcca cccacaaatc caattcgtct tggattggcg ttaaatttct | 540 |
| ccgtgtttca ctacgagatc gcgaattcac cggaggaagc gatttctctg gcaaagacaa | 600 |
| catttgacga ggctatggct gaccttcaca cactttcgga ggactcgtat aaagattcca | 660 |
| ccttgattat gcaacttctg cgcgacaatt tgacgctttg gaccgccgat aacgcaggtg | 720 |
| aggagggtgg cgaagcgcct caagagcccc aatccgagct cagtcagtc | 769 |

<210> SEQ ID NO 28
<211> LENGTH: 588
<212> TYPE: DNA
<213> ORGANISM: Artificial Sequence
<220> FEATURE:
<223> OTHER INFORMATION: Synthetic Construct

<400> SEQUENCE: 28

| gcactgaccg aattcattaa agaggagaaa ggttccatgg catccgtgag caagggcgag | 60 |
| gaggataaca tggccatcat caaggagttc atgcgcttca aggtgcacat ggagggctcc | 120 |
| gtgaacggcc acgagttcga gatcgagggc gagggcgagg ccgcccccta cgagggcacc | 180 |
| cagaccgcca agctgaaggt gaccaagggt ggccccctgc ccttcgcctg gacatcctg | 240 |
| tcccctcagt tcatgtacgg ctccaaggcc tacgtgaagc accccgccga catccccgac | 300 |
| tacttgaagc tgtccttccc cgagggcttc aagtgggagc gcgtgatgaa cttcgaggac | 360 |
| ggcggcgtgg tgaccgtgac ccaggactcc tccctgcagg acggcgagtt catctacaag | 420 |
| gtgaagctgc gcggcaccaa cttcccctcc gacggccccg taatgcagaa gaagaccatg | 480 |
| ggctgggagg cctcctccga gcggatgtac cccgaggacg gtggctctgg ctctgggtcg | 540 |
| actggtggta ccggcgccaa atctgacaag ctttaacagc tgaaaaaa | 588 |

<210> SEQ ID NO 29
<211> LENGTH: 58
<212> TYPE: DNA
<213> ORGANISM: Artificial Sequence
<220> FEATURE:

<223> OTHER INFORMATION: Synthetic Construct

<400> SEQUENCE: 29
gcattgcgaa ttcattaaag aggagaaagg aaccatgtcc cctatactag gttattgg    58

<210> SEQ ID NO 30
<211> LENGTH: 81
<212> TYPE: DNA
<213> ORGANISM: Artificial Sequence
<220> FEATURE:
<223> OTHER INFORMATION: Synthetic Construct

<400> SEQUENCE: 30
gtacagccta ggttaatgat ggtggtggtg gtgaagcttg tcagatttgg cgccggtacc    60
gggcccctgg aacagaactt c    81

<210> SEQ ID NO 31
<211> LENGTH: 33
<212> TYPE: DNA
<213> ORGANISM: Artificial Sequence
<220> FEATURE:
<223> OTHER INFORMATION: Synthetic Construct

<400> SEQUENCE: 31
gactgtcata tgtcccctat actaggttat tgg    33

<210> SEQ ID NO 32
<211> LENGTH: 33
<212> TYPE: DNA
<213> ORGANISM: Artificial Sequence
<220> FEATURE:
<223> OTHER INFORMATION: Synthetic Construct

<400> SEQUENCE: 32
cagtcagagc tcttaatgat ggtggtggtg gtg    33

<210> SEQ ID NO 33
<211> LENGTH: 34
<212> TYPE: DNA
<213> ORGANISM: Artificial Sequence
<220> FEATURE:
<223> OTHER INFORMATION: Synthetic Construct

<400> SEQUENCE: 33
agtcagttat aacagctctt ggctgttttg gcgg    34

<210> SEQ ID NO 34
<211> LENGTH: 26
<212> TYPE: DNA
<213> ORGANISM: Artificial Sequence
<220> FEATURE:
<223> OTHER INFORMATION: Synthetic Construct

<400> SEQUENCE: 34
tgaactcgag gagtttgtag aaacgc    26

<210> SEQ ID NO 35
<211> LENGTH: 35
<212> TYPE: DNA
<213> ORGANISM: Artificial Sequence
<220> FEATURE:
<223> OTHER INFORMATION: Synthetic Construct

<400> SEQUENCE: 35
gcagcacgcg taccatgtag cttaatcagc tgtta    35

```
<210> SEQ ID NO 36
<211> LENGTH: 35
<212> TYPE: DNA
<213> ORGANISM: Artificial Sequence
<220> FEATURE:
<223> OTHER INFORMATION: Synthetic Construct

<400> SEQUENCE: 36
taacagctga ttaagctaca tggtacgcgt gctgc                               35

<210> SEQ ID NO 37
<211> LENGTH: 29
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(6)
<223> OTHER INFORMATION: n is a, c, g, or t

<400> SEQUENCE: 37
nnnnnnagtc tgggtcgact ggtggtacc                                     29

<210> SEQ ID NO 38
<211> LENGTH: 44
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(9)
<223> OTHER INFORMATION: n is a, c, g, or t

<400> SEQUENCE: 38
nnnnnnnnna gcgtaccatg tagcttaatc agctgttaaa gctt                    44

<210> SEQ ID NO 39
<211> LENGTH: 30
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(7)
<223> OTHER INFORMATION: n is a, c, g, or t

<400> SEQUENCE: 39
nnnnnnntct ctgggtcgac tggtggtacc                                    30

<210> SEQ ID NO 40
<211> LENGTH: 43
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(8)
<223> OTHER INFORMATION: n is a, c, g, or t

<400> SEQUENCE: 40
nnnnnnnntc cgtaccatgt agcttaatca gctgttaaag ctt                     43

<210> SEQ ID NO 41
```

```
<211> LENGTH: 31
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(8)
<223> OTHER INFORMATION: n is a, c, g, or t

<400> SEQUENCE: 41
nnnnnnnnga tctgggtcga ctggtggtac c                              31

<210> SEQ ID NO 42
<211> LENGTH: 42
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(7)
<223> OTHER INFORMATION: n is a, c, g, or t

<400> SEQUENCE: 42
nnnnnnngac gtaccatgta gcttaatcag ctgttaaagc tt                  42

<210> SEQ ID NO 43
<211> LENGTH: 32
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(9)
<223> OTHER INFORMATION: n is a, c, g, or t

<400> SEQUENCE: 43
nnnnnnnnnc ttctgggtcg actggtggta cc                             32

<210> SEQ ID NO 44
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(6)
<223> OTHER INFORMATION: n is a, c, g, or t

<400> SEQUENCE: 44
nnnnnnctcg taccatgtag cttaatcagc tgttaaagct t                   41

<210> SEQ ID NO 45
<211> LENGTH: 69
<212> TYPE: DNA
<213> ORGANISM: Artificial Sequence
<220> FEATURE:
<223> OTHER INFORMATION: Synthetic Construct

<400> SEQUENCE: 45
atggaatgcg ttgactctga acgtcgtccg cacttcccgc agttctagta ctctgcgtct    60
ggcaccgcg                                                           69

<210> SEQ ID NO 46
<211> LENGTH: 93
```

<212> TYPE: DNA
<213> ORGANISM: Artificial Sequence
<220> FEATURE:
<223> OTHER INFORMATION: Synthetic Construct

<400> SEQUENCE: 46
ggtatgtacg acgcgaaaga cgacttcccg ctgcgtaaaa ccgcgtagga accgaacctg    60
aaactgcgtt ctcgtctgaa acagaaagtt gcg                                93

<210> SEQ ID NO 47
<211> LENGTH: 93
<212> TYPE: DNA
<213> ORGANISM: Artificial Sequence
<220> FEATURE:
<223> OTHER INFORMATION: Synthetic Construct

<400> SEQUENCE: 47
ctgccgtctg acccgccgga cacttcccg ctgcgtaaaa ccgtttagga accgaacctg     60
aaactgcgtt acaaaccgaa aaatctctg gaa                                 93

<210> SEQ ID NO 48
<211> LENGTH: 93
<212> TYPE: DNA
<213> ORGANISM: Artificial Sequence
<220> FEATURE:
<223> OTHER INFORMATION: Synthetic Construct

<400> SEQUENCE: 48
ccgggtctgc cgaacggtct gctgtctggt gacgaagact tctcttagat cgcggacatg    60
gacttctctg cgctgctgtc tcagatctct tct                                93

<210> SEQ ID NO 49
<211> LENGTH: 57
<212> TYPE: DNA
<213> ORGANISM: Artificial Sequence
<220> FEATURE:
<223> OTHER INFORMATION: Synthetic Construct

<400> SEQUENCE: 49
gttggtccga agcgccgtc tggtggtaaa aaagcgaccc aggcgtagca ggaatac        57

<210> SEQ ID NO 50
<211> LENGTH: 93
<212> TYPE: DNA
<213> ORGANISM: Artificial Sequence
<220> FEATURE:
<223> OTHER INFORMATION: Synthetic Construct

<400> SEQUENCE: 50
gacaccaaca ccaaaggtaa caaacgttct cgtacccgta ccgactagta ctctgcgggt    60
cagtctgttg aaatcctgga cggtgttgaa ctg                                93

<210> SEQ ID NO 51
<211> LENGTH: 93
<212> TYPE: DNA
<213> ORGANISM: Artificial Sequence
<220> FEATURE:
<223> OTHER INFORMATION: Synthetic Construct

<400> SEQUENCE: 51
cgtgacggtc tgaaaaaaga acgtctgctg acgaccgtc acgactaggg tctggactct     60
atgaaagacg aagaatacga acagatggtt aaa                                93

<210> SEQ ID NO 52
<211> LENGTH: 93
<212> TYPE: DNA
<213> ORGANISM: Artificial Sequence
<220> FEATURE:
<223> OTHER INFORMATION: Synthetic Construct

<400> SEQUENCE: 52
gacttcggtg cggcgcgtga actggaagac gacgaacagt tcgtttagct gtacggcacc    60
gaagaatacc tgcacccgga catgtacgaa cgt                                 93

<210> SEQ ID NO 53
<211> LENGTH: 93
<212> TYPE: DNA
<213> ORGANISM: Artificial Sequence
<220> FEATURE:
<223> OTHER INFORMATION: Synthetic Construct

<400> SEQUENCE: 53
ctggaataca acaacatcga aggtatgatc ctgctgtctg aactgtagcg tcgtcgtatc    60
cgttctatca acaaactgat ccgtatcggt cgt                                 93

<210> SEQ ID NO 54
<211> LENGTH: 93
<212> TYPE: DNA
<213> ORGANISM: Artificial Sequence
<220> FEATURE:
<223> OTHER INFORMATION: Synthetic Construct

<400> SEQUENCE: 54
acctctccgt cttacatcga caaactggtt cagggtatct ctttctagca gccgacctgc    60
ccggaccaca tgctgctgaa ctctcagctg ctg                                 93

<210> SEQ ID NO 55
<211> LENGTH: 72
<212> TYPE: DNA
<213> ORGANISM: Artificial Sequence
<220> FEATURE:
<223> OTHER INFORMATION: Synthetic Construct

<400> SEQUENCE: 55
atgtctggtc gtccgcgtac cacctagttc gcggaatctt gcaaaccggt tcagcagccg    60
tctgcgttcg gt                                                        72

<210> SEQ ID NO 56
<211> LENGTH: 54
<212> TYPE: DNA
<213> ORGANISM: Artificial Sequence
<220> FEATURE:
<223> OTHER INFORMATION: Synthetic Construct

<400> SEQUENCE: 56
atggcgtagg gtgttgcggt ttctgacggt gttatcaaag ttttcaacga catg          54

<210> SEQ ID NO 57
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid

```
<220> FEATURE:
<221> NAME/KEY: misc_feature
<222> LOCATION: (8)..(8)
<223> OTHER INFORMATION: Xaa can be any naturally occurring amino acid

<400> SEQUENCE: 57

Arg Ser Xaa Ser Pro Thr Pro Xaa Pro
1               5

<210> SEQ ID NO 58
<211> LENGTH: 10
<212> TYPE: PRT
<213> ORGANISM: Artificial Sequence
<220> FEATURE:
<223> OTHER INFORMATION: Synthetic Construct

<400> SEQUENCE: 58

Ile Pro Gly Thr Pro Pro Pro Asn Tyr Asp
1               5                   10

<210> SEQ ID NO 59
<211> LENGTH: 33
<212> TYPE: PRT
<213> ORGANISM: Artificial Sequence
<220> FEATURE:
<223> OTHER INFORMATION: Synthetic Construct

<400> SEQUENCE: 59

Ala Gly Pro Ala Asp Ala Pro Ala Gly Ala Val Val Gly Gly Gly Ser
1               5                   10                  15

Pro Ser Pro Arg Gly Arg Pro Gly Pro Val Pro Ala Pro Gly Leu Leu
            20                  25                  30

Ala

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

Trp Phe Tyr Ser Pro Phe Leu Glu
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 61

Arg Ser Xaa Thr Pro Thr Pro Xaa Pro
1               5

<210> SEQ ID NO 62
<211> LENGTH: 8
<212> TYPE: PRT
```

```
<213> ORGANISM: Artificial Sequence
<220> FEATURE:
<223> OTHER INFORMATION: Synthetic Construct

<400> SEQUENCE: 62

Asp Tyr Lys Asp Asp Asp Asp Lys
1               5

<210> SEQ ID NO 63
<211> LENGTH: 23
<212> TYPE: PRT
<213> ORGANISM: Artificial Sequence
<220> FEATURE:
<223> OTHER INFORMATION: Synthetic Construct

<400> SEQUENCE: 63

Met Glu Cys Val Asp Ser Glu Arg Arg Pro His Phe Pro Gln Phe Ser
1               5                   10                  15

Tyr Ser Ala Ser Gly Thr Ala
            20

<210> SEQ ID NO 64
<211> LENGTH: 31
<212> TYPE: PRT
<213> ORGANISM: Artificial Sequence
<220> FEATURE:
<223> OTHER INFORMATION: Synthetic Construct

<400> SEQUENCE: 64

Gly Met Tyr Asp Ala Lys Asp Asp Phe Pro Leu Arg Lys Thr Ala Ser
1               5                   10                  15

Glu Pro Asn Leu Lys Leu Arg Ser Arg Leu Lys Gln Lys Val Ala
            20                  25                  30

<210> SEQ ID NO 65
<211> LENGTH: 31
<212> TYPE: PRT
<213> ORGANISM: Artificial Sequence
<220> FEATURE:
<223> OTHER INFORMATION: Synthetic Construct

<400> SEQUENCE: 65

Leu Pro Ser Asp Pro Pro Glu His Phe Pro Leu Arg Lys Thr Val Ser
1               5                   10                  15

Glu Pro Asn Leu Lys Leu Arg Tyr Lys Pro Lys Lys Ser Leu Glu
            20                  25                  30

<210> SEQ ID NO 66
<211> LENGTH: 31
<212> TYPE: PRT
<213> ORGANISM: Artificial Sequence
<220> FEATURE:
<223> OTHER INFORMATION: Synthetic Construct

<400> SEQUENCE: 66

Pro Gly Leu Pro Asn Gly Leu Leu Ser Gly Asp Glu Asp Phe Ser Ser
1               5                   10                  15

Ile Ala Asp Met Asp Phe Ser Ala Leu Leu Ser Gln Ile Ser Ser
            20                  25                  30

<210> SEQ ID NO 67
<211> LENGTH: 19
<212> TYPE: PRT
<213> ORGANISM: Artificial Sequence
<220> FEATURE:
```

```
<223> OTHER INFORMATION: Synthetic Construct

<400> SEQUENCE: 67

Val Gly Pro Lys Ala Pro Ser Gly Gly Lys Lys Ala Thr Gln Ala Ser
1               5                   10                  15

Gln Glu Tyr

<210> SEQ ID NO 68
<211> LENGTH: 31
<212> TYPE: PRT
<213> ORGANISM: Artificial Sequence
<220> FEATURE:
<223> OTHER INFORMATION: Synthetic Construct

<400> SEQUENCE: 68

Asp Thr Asn Thr Lys Gly Asn Lys Arg Ser Arg Thr Arg Thr Asp Ser
1               5                   10                  15

Tyr Ser Ala Gly Gln Ser Val Glu Ile Leu Asp Gly Val Glu Leu
                20                  25                  30

<210> SEQ ID NO 69
<211> LENGTH: 31
<212> TYPE: PRT
<213> ORGANISM: Artificial Sequence
<220> FEATURE:
<223> OTHER INFORMATION: Synthetic Construct

<400> SEQUENCE: 69

Arg Asp Gly Leu Lys Lys Glu Arg Leu Leu Asp Asp Arg His Asp Ser
1               5                   10                  15

Gly Leu Asp Ser Met Lys Asp Glu Glu Tyr Glu Gln Met Val Lys
                20                  25                  30

<210> SEQ ID NO 70
<211> LENGTH: 31
<212> TYPE: PRT
<213> ORGANISM: Artificial Sequence
<220> FEATURE:
<223> OTHER INFORMATION: Synthetic Construct

<400> SEQUENCE: 70

Asp Phe Gly Ala Ala Arg Glu Leu Glu Asp Asp Glu Gln Phe Val Ser
1               5                   10                  15

Leu Tyr Gly Thr Glu Glu Tyr Leu His Pro Asp Met Tyr Glu Arg
                20                  25                  30

<210> SEQ ID NO 71
<211> LENGTH: 31
<212> TYPE: PRT
<213> ORGANISM: Artificial Sequence
<220> FEATURE:
<223> OTHER INFORMATION: Synthetic Construct

<400> SEQUENCE: 71

Leu Glu Tyr Asn Asn Ile Glu Gly Met Ile Leu Leu Ser Glu Leu Ser
1               5                   10                  15

Arg Arg Arg Ile Arg Ser Ile Asn Lys Leu Ile Arg Ile Gly Arg
                20                  25                  30

<210> SEQ ID NO 72
<211> LENGTH: 31
<212> TYPE: PRT
<213> ORGANISM: Artificial Sequence
<220> FEATURE:
```

```
<223> OTHER INFORMATION: Synthetic Construct

<400> SEQUENCE: 72

Thr Ser Pro Ser Tyr Ile Asp Lys Leu Val Gln Gly Ile Ser Phe Ser
1               5                   10                  15

Gln Pro Thr Cys Pro Asp His Met Leu Leu Asn Ser Gln Leu Leu
                20                  25                  30

<210> SEQ ID NO 73
<211> LENGTH: 24
<212> TYPE: PRT
<213> ORGANISM: Artificial Sequence
<220> FEATURE:
<223> OTHER INFORMATION: Synthetic Construct

<400> SEQUENCE: 73

Met Ser Gly Arg Pro Arg Thr Thr Ser Phe Ala Glu Ser Cys Lys Pro
1               5                   10                  15

Val Gln Gln Pro Ser Ala Phe Gly
                20

<210> SEQ ID NO 74
<211> LENGTH: 18
<212> TYPE: PRT
<213> ORGANISM: Artificial Sequence
<220> FEATURE:
<223> OTHER INFORMATION: Synthetic Construct

<400> SEQUENCE: 74

Met Ala Ser Gly Val Ala Val Ser Asp Gly Val Ile Lys Val Phe Asn
1               5                   10                  15

Asp Met
```